(12) United States Patent
Harris et al.

(10) Patent No.: US 10,047,401 B2
(45) Date of Patent: Aug. 14, 2018

(54) EXPRESSION PROTEIN-CODING AND NONCODING GENES AS PROGNOSTIC CLASSIFIERS IN EARLY STAGE LUNG CANCER

(71) Applicant: The United States of America, as represented by the Secretary, Department of Health & Human Services, Washington, DC (US)

(72) Inventors: Curtis C. Harris, Garrett Park, MD (US); Aaron Joseph Schetter, Germantown, MD (US); Hirokazu Okayama, Rockville, MD (US); Ichiro Akagi, Aizu-Wakamatsu (JP)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 14/423,069

(22) PCT Filed: Aug. 20, 2013

(86) PCT No.: PCT/US2013/055746
§ 371 (c)(1),
(2) Date: Feb. 20, 2015

(87) PCT Pub. No.: WO2014/031609
PCT Pub. Date: Feb. 27, 2014

(65) Prior Publication Data
US 2015/0337385 A1 Nov. 26, 2015

Related U.S. Application Data

(60) Provisional application No. 61/691,118, filed on Aug. 20, 2012.

(51) Int. Cl.
*C12Q 1/68* (2018.01)
*C12Q 1/6886* (2018.01)
*A61B 6/03* (2006.01)
*A61N 5/10* (2006.01)

(52) U.S. Cl.
CPC ............ *C12Q 1/6886* (2013.01); *A61B 6/032* (2013.01); *A61N 5/10* (2013.01); *C12Q 2600/118* (2013.01); *C12Q 2600/158* (2013.01); *C12Q 2600/178* (2013.01)

(58) Field of Classification Search
CPC .................................................. C12Q 1/6886
See application file for complete search history.

(56) References Cited

U.S. PATENT DOCUMENTS

2006/0094021 A1 5/2006 Costa et al.

2011/0152357 A1 6/2011 Croce

FOREIGN PATENT DOCUMENTS

JP 2011-516046 5/2011
WO WO-2009/121070 10/2009

OTHER PUBLICATIONS

Wada et al., "Surgical treatment of small cell carcinoma of the lung: advantage of preoperative chemotherapy" Lung Cancer 13:45-56, 1995.*
Affymetrix: "GeneChip Human Genome Arrays", 2004, pp. 1-4, XP002714318, Retrieved from the Internet: URL:<http://www.osa.sunysb.edu/udmf/ArraySheets/human_datasheet.pdf [retrieved on Oct. 8, 2013] the whole document figure Fig. 1.
J. Subramanian et al: "Gene Expression-Based Prognostic Signatures in Lung Cancer: Ready for Clinical Use?", JNCI Journal of the National Cancer Institute, vol. 102, No. 7, Apr. 7, 2010(Apr. 7, 2010), pp. 464-474, XP055073612, ISSN: 0027-8874, DOI: 10.1093/jnci/djq025.
Bao-Zhu Yuan et al: "DLC-1 operates as a tumor suppressor gene in human non-small cell lung carcinomas", Oncogene, vol. 23, No. 7, Feb. 19, 2004 (Feb. 19, 2004), pp. 1405-1411, XP055082980, ISSN: 0950-9232, DOI: 10.1038/sj.onc.1207291 the whole document.
M. Saito et al: "The Association of MicroRNA Expression with Prognosis and Progression in Early-Stage, Non-Small Cell Lung denocarcinoma: A Retrospective Analysis of Three Cohorts", Clinical Cancer Research, vol. 17, No. 7, Apr. 1, 2011 (Apr. 1, 2011), pp. 1875-1882, XP055082883, ISSN: 1078-0432, DOI: 10.1158/1078-0432.CCR-10-2961.
I. Akagi et al: "Combination of Protein Coding and Noncoding Gene Expression as a Robust Prognostic Classifier in Stage I Lung Adenocarcinoma", Cancer Research, vol. 73, No. 13, Jul. 1, 2013 (Jul. 1, 2013), pp. 3821-3832, XP055082817, ISSN: 0008-5472, DOI: 10.1158/0008-5472.CAN-13-031 the whole document.
Office Action in corresponding Japanese Patent Application No. 2015-528575 dated Jun. 13, 2017 (including English transslation).
Oncogene, 2004, vol. 23, pp. 1405-1411.
Journal of Clinical Oncology, 2007, vol. 25, No. 35, pp. 5562-5569.
2011-516046, 2010, vol. 5, No. 8, e12222.
Clinical Cancer Research, 2011, vol. 17, No. 7, pp. 1875-1882.
Wakelee H, et al., Oncologist., 2007, vol. 12, pp. 331-337.
Silver DP, et al., Cancer Discov., 2012, vol. 2, pp. 679-684.
Subramanian, J. et al., J. Natl. Cancer Inst., 2010, vol. 102, pp. 464-474.
Shedden, K., et al., Nat Med, 2008, vol. 14, pp. 822-827.
Schetter AJ, et al., Cancer J., 2012, vol. 18, pp. 244-252.
Rousseaux, S., et al., Sci Transl Med, 2013, vol. 5 pp. 186ra66.
Roselli M, et al., Int J Cancer., 2006, vol. 119, pp. 955-960.
Okayama, H., et al., 2011, Cancer Res, 2011, GSE31210.
Freedman DA, et al., Mol Cell Biol., 1998, vol. 18, pp. 7288-7293.
Saha T, et al., J Biol Chem., 2010, vol. 285, pp. 19092-19105.
Brodie KM, et al., J Biol Chem., 2012, vol. 287, pp. 7701-7716.
Zhang X, et al., Cancer Res., 2012, vol. 72, pp. 4707-4713.
Hanahan D, et al., Cell., 2011, vol. 144, pp. 646-674.
Durkin ME, et al., Oncogene, 2004, vol. 23, pp. 1405-1411.

(Continued)

*Primary Examiner* — Prema Mertz
(74) *Attorney, Agent, or Firm* — Bryan D. Zerhusen; Locke Lord LLP

(57) ABSTRACT

The invention provides novel biomarkers (four genes BRCA1, HIF1A, DLC1, and XPO1 alone or in combination of miR-21) for early stage lung cancer.

2 Claims, 28 Drawing Sheets

(56) References Cited

OTHER PUBLICATIONS

Saito M, et al., Clin Cancer Res., 2011. vol. 17, pp. 1875-1882.
Lee, E.S., et al., Clin Cancer Res., 2008, vol. 14, pp. 7397-7404.
Botling, J.et al., Clin Cancer Res., 2013, vol. 19, pp. 194-204.
Aebersold DM, et al.,Cancer Res., 2001, vol. 61, pp. 2911-2916.
Wilkerson, M. D., et al., Clin Cancer Res, 2010, vol. 16, pp. 4864-4875.
Tang, H.,et al., Clin Cancer Res, 2013, vol. 19, pp. 1577-1586.
Zhong H, et al., Cancer Res., 1999, vol. 59, pp. 5830-5835.
Wilkerson, M. D., et al., PLoS One, 2012, vol. 7, pp. e36530.
Wan, Y.W. et al., PLoS One, 2010, vol. 5, pp. e12222.
Volinia S, et al., Proc Natl Acad Sci U S A, 2006, vol. 103, pp. 2257-2261.
Rosell R, et al., PLoS One., 2007, vol. 2, p. e1129.
Raponi, M. et al., Cancer Res. 2006, vol. 66, pp. 7466-7472.
Castanotto D, et al., Proc Natl Acad Sci U S A, 2009, vol. 106, pp. 21655-21659.
Cai X, et al., Proc Natl Acad Sci U S A, 2008, vol. 105, pp. 16958-16963.
Bussing I, et al., EMBO J., 2010, vol. 29, pp. 1830-1839.
Birner P, et al., Cancer Res., 2000, vol. 60, pp. 4693-4696.
Bhattacharjee, A., et al., Proc Natl Acad Sci U S A, 2001, vol. 98, pp. 13790-13795.
Akagi, I., et al., Cancer Res, 2013, vol. 73, pp. 3821-3832.
Castro M, et al., J Transl Med., 2010, vol. 8, p. 86.
Lossos, et al, N. Engl. J. Med., 2004, vol. 350, pp. 1828-1837.
Larsen, J. E. et al., Carcinogenesis, 2007, vol. 28, pp. 760-766.
Kennedy RD, et al, J Natl Cancer Inst., 2004, vol. 96, pp. 1659-1668.
Kato H, et al., N Engl J Med., 2004, vol. 350, pp. 1713-2.
Hatley ME, et al., Cancer Cell, vol. 2010, No1 18, pp. 282-293.
Giatromanolaki A, et al., Br J Cancer, 2001, vol. 85, pp. 881-890.
Chen, H.Y. et al., N. Engl. J. Med., 2007, vol. 356, pp. 11-20.
Bianchi, F. et al., J. Clin. Invest., 2007, vol. 117, pp. 3436-3444.
Zhu, C. Q., et al., J Clin Oncol, 2010, vol. 28, pp. 4417-4424.
Winton T, et al., N Engl J Med. 2005, vol. 352, pp. 2589-2597.

\* cited by examiner

Cox regression analysis of the four-gene signature and miR-21 expression from Japan and US/Norway cohorts (AJCC 7th edition)

| Variable | | Univariate analysis | | | Multivariate analysis | | |
|---|---|---|---|---|---|---|---|
| | | HR | 95%CI | P | HR | 95%CI | P |
| Japan cohort (Stage I-II, n=199) | | | | | | | |
| 4 gene classifier (qRT-PCR) | High / Low | 3.56 | 1.94  6.55 | 0.000 | 2.29 | 1.12  4.71 | 0.024 |
| miR-21 (Nanostring) | High / Low | 2.77 | 1.54  4.98 | 0.001 | 1.41 | 0.70  2.81 | 0.333 |
| AJCC 7th Stage | II / I | 3.19 | 1.87  5.45 | 0.000 | 2.14 | 1.20  3.83 | 0.010 |
| Age | Continuous | 1.03 | 0.99  1.07 | 0.132 | | | |
| Gender | Male /Female | 1.27 | 0.74  2.16 | 0.382 | | | |
| Packyears | ≥20 /<20 | 1.62 | 0.94  2.79 | 0.084 | | | |
| US/Norway cohort (Stage I-II, n=89) | | | | | | | |
| 4 gene classifier (qRT-PCR) | High / Low | 1.87 | 1.00  3.50 | 0.048 | 1.84 | 0.95  3.56 | 0.071 |
| miR-21 (Nanostring) | High / Low | 3.31 | 1.68  6.50 | 0.001 | 3.28 | 1.61  6.68 | 0.001 |
| AJCC 7th Stage | II / I | 1.60 | 0.85  3.03 | 0.147 | 1.46 | 0.77  2.76 | 0.248 |
| Age | Continuous | 1.01 | 0.98  1.04 | 0.451 | | | |
| Gender | Male /Female | 1.02 | 0.55  1.90 | 0.943 | | | |
| Packyears | ≥20 /<20 | 0.95 | 0.47  1.90 | 0.881 | | | |
| Japan cohort (Stage I, n=136) | | | | | | | |
| 4 gene classifier (qRT-PCR) | High / Low | 4.76 | 1.79  12.64 | 0.002 | 4.16 | 1.40  12.34 | 0.010 |
| miR-21 (Nanostring) | High / Low | 3.89 | 1.56  9.69 | 0.004 | 1.73 | 0.60  4.96 | 0.309 |
| AJCC 7th Stage | IB/ IA | 3.25 | 1.50  7.01 | 0.003 | 3.25 | 1.44  7.33 | 0.005 |
| Age | Continuous | 1.00 | 0.95  1.06 | 0.919 | | | |
| Gender | Male /Female | 0.98 | 0.45  2.14 | 0.967 | | | |
| Packyears | ≥20 /<20 | 1.54 | 0.69  3.47 | 0.294 | | | |
| US/Norway cohort (Stage I, n=47) | | | | | | | |
| 4 gene classifier (qRT-PCR) | High / Low | 3.97 | 1.51  10.43 | 0.005 | 4.22 | 1.54  11.54 | 0.005 |
| miR-21 (Nanostring) | High / Low | 4.11 | 1.49  11.36 | 0.006 | 4.77 | 1.54  14.80 | 0.007 |
| AJCC 7th Stage | IB/ IA | 0.71 | 0.27  1.84 | 0.478 | 1.57 | 0.53  4.70 | 0.417 |
| Age | Continuous | 1.01 | 0.97  1.06 | 0.578 | | | |
| Gender | Male /Female | 0.97 | 0.43  2.20 | 0.944 | | | |
| Packyears | ≥20 /<20 | 1.07 | 0.40  2.89 | 0.889 | | | |

All modles were adjusted for cohort membership
Multivariate models included all variable that were significant in univariate models in at least one cohort

FIG. 11

| | GEO Access# | Oncomine Name | Comments2 |
|---|---|---|---|
| GEO | GSE40407 | | Excluded: Do not contain any primary ADC samples (normal epithelium, blood, fluid, metastasis, other cancer types, etc) |
| GEO | GSE22047 | | |
| GEO | GSE35640 | | |
| GEO | GSE20189 | | |
| GEO | GSE39345 | | |
| GEO | GSE19027 | | |
| GEO | GSE12472 | | |
| GEO | GSE27489 | | |
| GEO | GSE12771 | | |
| GEO | GSE13255 | | |
| GEO | GSE27554 | | |
| GEO | GSE12815 | | |
| GEO | GSE12428 | | |
| GEO | GSE4115 | | |
| GEO | GSE43346 | | |
| GEO | GSE15240 | | |
| GEO | GSE20853 | | |
| GEO | GSE4716 | Tomida Lung | |
| GEO | GSE31799 | | |
| GEO | GSE32863 | | |
| GEO | GSE10245 | | |
| GEO | GSE19804 | | |
| GEO | GSE1987 | | |
| GEO | GSE29016 | | |
| GEO | GSE12667 | | |
| GEO | GSE32665 | | |
| GEO | GSE18842 | | |
| GEO | GSE33072 | | |
| GEO | GSE1037 | | |
| GEO | GSE18805 | | |
| GEO | GSE6253 | | |
| GEO | GSE40275 | | |
| GEO | GSE7880 | | Excluded: Insufficient sample number, clinical information or lack of 4 gene-expression data |
| GEO | GSE28571 | | |
| GEO | GSE7339 | | |
| GEO | GSE12236 | | |
| GEO | GSE24933 | | |
| GEO | GSE27262 | | |
| GEO | GSE20875 | | |
| GEO | GSE25326 | | |
| GEO | GSE27716 | | |
| GEO | GSE10445 | Broet Lung | |
| GEO | GSE10072 | Landi Lung | |
| GEO | GSE7670 | Su Lung | |
| GEO | GSE31546 | | |
| GEO | GSE31547 | | |
| GEO | GSE31552 | | |
| GEO | GSE11117 | | |
| GEO | GSE29013 | | |
| GEO | GSE14814 | Zhu Lung | |
| GEO | GSE19188 | Hou Lung | |
| GEO | GSE4882 | Chen Lung 3 | |

FIG. 20 A

| Source | Dataset | | Status |
|---|---|---|---|
| GEO | GSE5843 | | Excluded: Not clinical sample (Cell lines, Xenografts, etc) |
| GEO | GSE22863 | | |
| GEO | GSE45626 | | |
| GEO | GSE31625 | | |
| GEO | GSE6135 | | |
| GEO | GSE9994 | | |
| GEO | GSE22874 | | |
| GEO | GSE32036 | | |
| GEO | GSE4824 | | |
| GEO | GSE32989 | | |
| GEO | GSE4342 | | |
| GEO | GSE14315 | | |
| GEO | GSE47206 | | |
| GEO | GSE14925 | | |
| GEO | GSE35913 | | |
| GEO | GSE20549 | | |
| GEO | GSE5816 | | |
| GEO | GSE43567 | | |
| GEO | GSE36176 | | |
| GEO | GSE8500 | | |
| GEO | GSE32497 | | Excluded: Superseries containing subseries, see subseries |
| GEO | GSE22862 | | |
| GEO | GSE35603 | | |
| GEO | GSE33198 | | |
| GEO | GSE31800 | | |
| GEO | GSE36471 | | |
| GEO | GSE33356 | | |
| GEO | GSE28582 | | |
| GEO | GSE32867 | | |
| GEO | GSE31908 | | |
| GEO | GSE27719 | | |
| GEO | GSE3141 | Bild Lung | |
| GEO | GSE8694 | Lee Lung | Included |
| GEO | GSE37745 | | |
| GEO | GSE11969 | | |
| GEO | GSE30219 | | |
| GEO | GSE42127 | | |
| GEO | GSE26939 | | |
| GEO | GSE31210 | | |
| GEO | GSE13213 | | |
| ONCOMINE | | Bhattacharjee Lung | |
| ONCOMINE | | DirectorsChallenge Lung | Excluded: Insufficient sample number, clinical information or lack of 4 gene-expression data |
| ONCOMINE | | Garber Lung | |
| ONCOMINE | | Beer Lung | |
| ONCOMINE | | TCGA Lung | |
| ONCOMINE | | Raponi Lung | Excluded: Do not contain any primary ADC samples |
| ONCOMINE | | Larsen Lung | |

FIG. 20 B

EXPRESSION PROTEIN-CODING AND NONCODING GENES AS PROGNOSTIC CLASSIFIERS IN EARLY STAGE LUNG CANCER

RELATED APPLICATIONS

This application is a national stage entry of International Application No. PCT/US2013/055746 having an international filing date of Aug. 20, 2013, which claims priority to US Provisional Application No. 61/691,118, filed on Aug. 20, 2012, the entireties of which are incorporated by reference herein.

STATEMENT OF RIGHTS TO INVENTIONS MADE UNDER FEDERALLY SPONSORED RESEARCH

This work was supported by the National Cancer Institute Intramural Research Program. The Government has certain rights in this invention.

SEQUENCE LISTING

The instant application contains a Sequence Listing which has been submitted electronically in ASCii format and is hereby incorporated by reference in its entirety. Said ASCii copy is named 89945(47992)_sl.txt and is 92,515 bytes in size.

BACKGROUND OF THE INVENTION

Surgery with curative intent is the standard of care for stage I non-small cell lung cancer (NSCLC) patients (National Comprehensive Cancer Network, NCCN, Guidelines, http://www.nccn.org). However, even after successful surgery and with histologically negative lymph nodes, 20-30% of stage I NSCLC patients will recur. While adjuvant chemotherapy can improve survival in patients with stage II or IIIA disease, its benefit in stage I patients is controversial.

Therefore, there remains a need in the art for the development of biomarkers that can identify stage I lung cancer patients at high risk of recurrence who may benefit from adjuvant therapy.

SUMMARY OF THE INVENTION

As described below, this invention provides novel biomarkers for early stage lung adenocarcinoma. The present invention provides, in part, a molecular classifier that may be clinically useful at stratifying early stage lung cancer in diverse patient populations to reliably identify patients at high risk of disease progression and may be useful to aid in choosing appropriate therapeutic pathways for these patients.

In aspects, the invention provides methods for determining the prognosis of a subject with lung cancer. In embodiments, the methods involve detecting the levels of BRCA1, HIF1A, DLC1, and XPO1 in a sample obtained from the subject. In embodiments, the methods involve comparing the levels of BRCA1, HIF1A, DLC1, and XPO1 to a reference. In embodiments, the methods involve identifying the subject as having an adverse prognosis when the levels of BRCA1, HIF1A, and XPO1 are increased relative to the reference or when the level of DLC1 is decreased relative to the reference.

In embodiments, the reference is the levels of BRCA1, HIF1A, DLC1, and XPO1 in a healthy control. In some related embodiments, the subject is identified as having an adverse prognosis when the levels of BRCA1, HIF1A, and XPO1 are increased relative to the reference and when the level of DLC1 is decreased relative to the reference. In some related embodiments, the subject is identified as having an adverse prognosis when the subject has a higher classifier score of (0.104×BRCA1)+(0.133×HIF1A)+(−0.246×DLC1)+(0.378×XPO1) relative to the reference.

In aspects, the invention provides methods for determining the prognosis of a subject with lung cancer. In embodiments, the methods involve detecting the levels of BRCA1, HIF1A, DLC1, XPO1, and miR-21 in a sample obtained from the subject. In embodiments, the methods involve comparing the levels of BRCA1, HIF1A, DLC1, XPO1, and miR-21 to a reference. In embodiments, the methods involve identifying the subject as having an adverse prognosis when the levels of BRCA1, HIF1A, XPO1, and miR-21 are increased relative to the reference or when the level of DLC1 is decreased relative to the reference.

In embodiments, the reference is the levels of BRCA1, HIF1A, DLC1, XPO1, and miR-21 in a healthy control. In some related embodiments, the subject is identified as having an adverse prognosis when the levels of BRCA1, HIF1A, XPO1, and miR-21 are increased relative to the reference and when the level of DLC1 is decreased relative to the reference. In some related embodiments, the subject is identified as having an adverse prognosis when the subject has a higher classifier score of (0.104×BRCA1)+(0.133×HIF1A)+(−0.246×DLC1)+(0.378×XPO1) relative to the reference and when the subject has a higher miR-21 level relative to the reference.

In aspects, the invention provides methods for diagnosing a subject at risk of developing lung cancer. In embodiments, the methods involve detecting the levels of BRCA1, HIF1A, DLC1, and XPO1 in a sample obtained from the subject. In embodiments, the methods involve comparing the levels of BRCA1, HIF1A, DLC1, and XPO1 to a reference. In embodiments, the methods involve identifying the subject as at risk for developing lung cancer when the levels of BRCA1, HIF1A, and XPO1 are increased relative to the reference or when the level of DLC1 is decreased relative to the reference.

In embodiments, the reference is the level of BRCA1, HIF1A, DLC1, and XPO1 in a healthy control. In some related embodiments, the subject is identified as at risk for developing lung cancer when the levels of BRCA1, HIF1A, and XPO1 are increased relative to the reference and when the level of DLC1 is decreased relative to the reference. In some related embodiments, the subject is identified as at risk for developing lung cancer when the subject has a higher classifier score of (0.104×BRCA1)+(0.133×HIF1A)+(−0.246×DLC1)+(0.378×XPO1) relative to the reference.

In aspects, the invention provides methods for diagnosing a subject is at risk of developing lung cancer. In embodiments, the methods involve detecting the levels of BRCA1, HIF1A, DLC1, XPO1, and miR-21 in a sample obtained from the subject. In embodiments, the methods involve comparing the levels of BRCA1, HIF1A, DLC1, XPO1, and miR-21 to a reference. In embodiments, the methods involve identifying the subject as at risk for developing lung cancer when the levels of BRCA1, HIF1A, XPO1, and miR-21 are increased relative to the reference or when the level of DLC1 is decreased relative to the reference.

In embodiments, the reference is the level of BRCA1, HIF1A, DLC1, XPO1, and miR-21 in a healthy control. In some related embodiments, the subject is identified as at risk for developing lung cancer when the levels of BRCA1, HIF1A, XPO1, and miR-21 are increased relative to the reference and when the level of DLC1 is decreased relative to the reference. In some related embodiments, the subject is identified as at risk for developing lung cancer when the subject has a higher classifier score of (0.104×BRCA1)+ (0.133×HIF1A)+(−0.246×DLC1)+(0.378×XPO1) relative to the reference and when the subject has a higher miR-21 level relative to the reference.

In aspects, the invention provides methods for diagnosing a risk of lung cancer recurrence in a subject. In embodiments, the methods involve detecting the levels of BRCA1, HIF1A, DLC1, and XPO1 in a sample obtained from the subject. In embodiments, the methods involve comparing the levels of BRCA1, HIF1A, DLC1, and XPO1 to a reference. In embodiments, the methods involve identifying the subject as at risk for recurrence of lung cancer when the levels of BRCA1, HIF1A, and XPO1 are increased relative to the reference or when the level of DLC1 is decreased relative to the reference.

In embodiments, the reference is the level of BRCA1, HIF1A, DLC1, and XPO1 in a healthy control. In some related embodiments, the subject is identified as at risk for recurrence of lung cancer when the levels of BRCA1, HIF1A, and XPO1 are increased relative to the reference and when the level of DLC1 is decreased relative to the reference. In some related embodiments, the subject is identified as at risk for recurrence of lung cancer when the subject has a higher classifier score of (0.104×BRCA1)+(0.133× HIF1A)+(−0.246×DLC1)+(0.378×XPO1) relative to the reference.

In aspects, the invention provides methods for diagnosing a risk of lung cancer recurrence in a subject. In embodiments, the methods involve detecting the levels of BRCA1, HIF1A, DLC1, XPO1, and miR-21 in a sample obtained from the subject. In embodiments, the methods involve comparing the levels of BRCA1, HIF1A, DLC1, XPO1, and miR-21 to a reference. In embodiments, the methods involve identifying the subject as at risk for recurrence of lung cancer when the levels of BRCA1, HIF1A, XPO1, and miR-21 are increased relative to the reference or when the level of DLC1 is decreased relative to the reference.

In embodiments, the reference is the level of BRCA1, HIF1A, DLC1, XPO1, and miR-21 in a healthy control. In some related embodiments, the subject is identified as at risk for recurrence of lung cancer when the levels of BRCA1, HIF1A, XPO1, and miR-21 are increased relative to the reference and when the level of DLC1 is decreased relative to the reference. In some related embodiments, the subject is identified as at risk for recurrence of lung cancer when the subject has a higher classifier score of (0.104×BRCA1)+ (0.133×HIF1A)+(−0.246×DLC1)+(0.378×XPO1) relative to the reference and when the subject has a higher miR-21 level relative to the reference.

In aspects, the invention provides methods for selecting an appropriate therapy for a subject. In embodiments, the methods involve detecting the levels of BRCA1, HIF1A, DLC1, and XPO1 in a sample obtained from the subject, wherein the sample is a tissue sample obtained from the lung. In embodiments, the methods involve comparing the levels of BRCA1, HIF1A, DLC1, and XPO1 to a reference. In embodiments, an increase in the levels of BRCA1, HIF1A, and XPO1 or a decrease in DLC1 relative to the reference indicates that lung cancer therapy is appropriate for the subject.

In some related embodiments, the reference is the level of BRCA1, HIF1A, DLC1, and XPO1 in a healthy control. In some related embodiments, lung cancer therapy is identified as appropriate for the subject when the subject has a higher classifier score of (0.104×BRCA1)+(0.133×HIF1A)+(− 0.246×DLC1)+(0.378×XPO1) relative to the reference.

In aspects, the invention provides methods for selecting an appropriate therapy for a subject. In embodiments, the methods involve detecting the levels of BRCA1, HIF1A, DLC1, XPO1, and miR-21 in a sample obtained from the subject, wherein the sample is a tissue sample obtained from the lung. In embodiments, the methods involve comparing the levels of BRCA1, HIF1A, DLC1, XPO1, and miR-21 to a reference. In embodiments, an increase in the levels of BRCA1, HIF1A, XPO1, and miR-21 or a decrease in DLC1 relative to the reference indicates that lung cancer therapy is appropriate for the subject.

In some related embodiments, the reference is the level of BRCA1, HIF1A, DLC1, and XPO1, and miR-21 in a healthy control. In some related embodiments, lung cancer therapy is identified as appropriate for the subject when the subject has a higher classifier score of (0.104×BRCA1)+(0.133× HIF1A)+(−0.246×DLC1)+(0.378×XPO1) relative to the reference and when the subject has a higher miR-21 level relative to the reference.

In aspect, the invention provides methods of predicting clinical outcome for a subject diagnosed with lung cancer, comprising (a) detecting the levels of BRCA1, HIF1A, DLC1, XPO1, and miR-21 in a sample obtained from the subject; (b) comparing the levels of BRCA1, HIF1A, DLC1, XPO1, and miR-21 to a reference; and (c) wherein the level of BRCA1, HIF1A, XPO1, and miR-21 that are increased relative to the reference or wherein the level of DLC1 that is decreased relative to the reference is negatively correlated with an increased likelihood of a positive clinical outcome.

In some related embodiments, said clinical outcome is expressed in terms of Recurrence-Free interval (RFI), an increase in the time of Overall Survival (OS), an increase in the time of Disease-Free Survival (DFS), an increase in the duration of Distant Recurrence-Free Interval (DRFI), or long term survival.

In other related embodiments, the method further comprises the classification of the subject into a risk group.

In any of the above aspects and embodiments, the sample can be a tissue sample obtained from the lung.

In any one of the above aspects and embodiments, the lung cancer is early stage.

In any of the above aspects and embodiments, the subject is assigned to closer follow-up when identified as having an adverse prognosis, at risk of developing lung cancer, at risk of recurrence, or appropriate for lung cancer therapy. In embodiments, the subject is assigned to more frequent screenings when identified as having an adverse prognosis, at risk of developing lung cancer, at risk of recurrence, or appropriate for lung cancer therapy. In some embodiments, the subject is assigned to more frequent CT scans when identified as having an adverse prognosis, at risk of developing lung cancer, at risk of recurrence, or appropriate for lung cancer therapy.

In any of the above aspects and embodiments, the subject is selected for a clinical trial when identified as having an adverse prognosis, at risk of developing lung cancer, at risk of recurrence, or appropriate for lung cancer therapy.

In any of the above aspects and embodiments, the subject is administered adjuvant radiotherapy when identified as having an adverse prognosis, at risk of developing lung cancer, at risk of recurrence, or appropriate for lung cancer therapy.

In any of the above aspects and embodiments, the subject is administered adjuvant chemotherapy when identified as having an adverse prognosis, at risk of developing lung cancer, at risk of recurrence, or appropriate for lung cancer therapy. In embodiments, the adjuvant chemotherapy is Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etoposide, Everolimus, Exemestane, Filgrastim, Floxuridine, Fludarabine, Fluorouracil, Fluoxymesterone, Flutamide, Gefitinib, Gemcitabine, Gemtuzumab ozogamicin, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trastuzumab, Tretinoin, Valrubicin, VEGF inhibitors and traps, Vinblastine, Vincristine, Vindesine, Vinorelbine, Vorinostat, or combination thereof.

In any of the above aspects and embodiments, the lung cancer is non-small cell lung cancer. In related embodiments, the lung cancer is stage 1A or stage 1B.

In any of the above aspects and embodiments, the subject is a mammal (e.g., human).

In any of the above aspects and embodiments, detecting the levels of BRCA1, HIF1A, DLC1, XPO1, and/or miR-21 involves measuring the RNA levels of BRCA1, HIF1A, DLC1, XPO1, and/or miR-21.

In any of the above aspects and embodiments, the levels of BRCA1, HIF1A, DLC1, XPO1, and/or miR-21 are detected by microarray, RT-PCR, qRT-PCR, nanostring assay, chromatography, mass spectrometry, spectroscopy, immunoassay, or in situ hybridization. In related embodiments, the level of miR-21 is detected by microRNA analysis.

In any of the above aspects and embodiments, the method further comprises the step of creating a report summarizing the method.

In aspects, the invention provides kits for aiding the diagnosis of lung cancer. In embodiments, the kits contain at least one reagent capable of detecting or capturing BRCA1, HIF1A, DLC1, XPO1, or a combination thereof. In related embodiments, the reagent is an antibody, a mass spectrometry probe, or a microarray. In yet another related embodiment, the kits contain directions for using the reagent to analyze the level of BRCA1, HIF1A, DLC1, XPO1, or a combination thereof.

In aspects, the invention provides kits for aiding the diagnosis of lung cancer. In embodiments, the kits contain at least one reagent capable of detecting or capturing BRCA1, HIF1A, DLC1, XPO1, miR-21, or a combination thereof. In related embodiments, the reagent is an antibody, a mass spectrometry probe, or a microarray. In yet another related embodiment, the kits contain directions for using the reagent to analyze the level of BRCA1, HIF1A, DLC1, XPO1, miR-21, or a combination thereof.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

Definitions

To facilitate an understanding of the present invention, a number of terms and phrases are defined below.

As used herein, the singular forms "a", "an", and "the" include plural forms unless the context clearly dictates otherwise. Thus, for example, reference to "a biomarker" includes reference to more than one biomarker.

Unless specifically stated or obvious from context, as used herein, the term "or" is understood to be inclusive.

The term "including" is used herein to mean, and is used interchangeably with, the phrase "including but not limited to."

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "agent" is meant any small molecule chemical compound, antibody, nucleic acid molecule, or polypeptide, or fragments thereof.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "BRCA1" is meant a polynucleotide encoding a breast cancer type 1 susceptibility protein. An exemplary BRCA1 nucleic acid molecule is provided at NCBI Accession No. NM_007294.

An exemplary BRCA1 nucleotide sequence SEQ ID NO. 1 (NM-007294) is provided below:

```
  1 gtaccttgat ttcgtattct gagaggctgc tgcttagcgg tagcccttg gtttccgtgg
 61 caacggaaaa gcgcgggaat tacagataaa ttaaaactgc gactgcgcgg cgtgagctcg
121 ctgagacttc ctggacgggg gacaggctgt ggggtttctc agataactgg gcccctgcgc
```

-continued

```
 181 tcaggaggcc ttcaccctct gctctgggta aagttcattg gaacagaaag aaatggattt
 241 atctgctctt cgcgttgaag aagtacaaaa tgtcattaat gctatgcaga aaatcttaga
 301 gtgtcccatc tgtctggagt tgatcaagga acctgtctcc acaaagtgtg accacatatt
 361 ttgcaaattt tgcatgctga aacttctcaa ccagaagaaa gggccttcac agtgtccttt
 421 atgtaagaat gatataacca aaaggagcct acaagaaagt acgagattta gtcaacttgt
 481 tgaagagcta ttgaaaatca tttgtgcttt tcagcttgac acaggtttgg agtatgcaaa
 541 cagctataat tttgcaaaaa aggaaaataa ctctcctgaa catctaaaag atgaagtttc
 601 tatcatccaa agtatgggct acagaaaccg tgccaaaaga cttctacaga gtgaacccga
 661 aaatccttcc ttgcaggaaa ccagtctcag tgtccaactc tctaaccttg gaactgtgag
 721 aactctgagg acaaagcagc ggatacaacc tcaaaagacg tctgtctaca ttgaattggg
 781 atctgattct tctgaagata ccgttaataa ggcaacttat tgcagtgtgg gagatcaaga
 841 attgttacaa atcacccctc aaggaaccag ggatgaaatc agtttggatt ctgcaaaaaa
 901 ggctgcttgt gaattttctg agacggatgt aacaaatact gaacatcatc aacccagtaa
 961 taatgatttg aacaccactg agaagcgtgc agctgagagg catccagaaa agtatcaggg
1021 tagttctgtt tcaaacttgc atgtggagcc atgtggcaca aatactcatg ccagctcatt
1081 acagcatgag aacagcagtt tattactcac taaagacaga atgaatgtag aaaaggctga
1141 attctgtaat aaaagcaaac agcctggctt agcaaggagc caacataaca gatgggctgg
1201 aagtaaggaa acatgtaatg ataggcggac tcccagcaca gaaaaaaagg tagatctgaa
1261 tgctgatccc ctgtgtgaga gaaaagaatg gaataagcag aaactgccat gctcagagaa
1321 tcctagagat actgaagatg ttccttggat aacactaaat agcagcattc agaaagttaa
1381 tgagtggttt tccagaagtg atgaactgtt aggttctgat gactcacatg atggggagtc
1441 tgaatcaaat gccaaagtag ctgatgtatt ggacgttcta aatgaggtag atgaatattc
1501 tggttcttca gagaaaatag acttactggc cagtgatcct catgaggctt taatatgtaa
1561 aagtgaaaga gttcactcca atcagtagat gagtaatatt gaagacaaaa tatttgggaa
1621 aacctatcgg aagaaggcaa gcctccccaa cttaagccat gtaactgaaa atctaattat
1681 aggagcattt gttactgagc cacagataat acaagagcgt cccctcacaa ataaattaaa
1741 gcgtaaaagg agacctacat caggccttca tcctgaggat tttatcaaga agcagattt
1801 ggcagttcaa aagactcctg aaatgataaa tcagggaact aaccaaacgg agcagaatgg
1861 tcaagtgatg aatattacta atagtggtca tgagaataaa acaaaaggtg attctattca
1921 gaatgagaaa aatcctaacc aatagaatc actcgaaaaa gaatctgctt caaaacgaa
1981 agctgaacct ataagcagca gtataagcaa tatggaactc gaattaaata tccacaattc
2041 aaaagcacct aaaaagaata ggctgaggag gaagtcttct accaggcata ttcatgcgct
2101 tgaactagta gtcagtagaa atctaagccc acctaattgt actgaattgc aaattgatag
2161 ttgttctagc agtgaagaga taaagaaaaa aagtacaac caaatgccag tcaggcacag
2221 cagaaaccta caactcatgg aaggtaaaga acctgcaact ggagccaaga agagtaacaa
2281 gccaaatgaa cagacaagta aaagacatga cagcgatact ttcccagagc tgaagttaac
2341 aaatgcacct ggttctttta ctaagtgttc aaataccagt gaacttaaag aatttgtcaa
2401 tcctagcctt ccaagagaag aaaaagaaga gaaactagaa acagttaaag tgtctaataa
2461 tgctgaagac cccaaagatc tcatgttaag tggagaaagg gttttgcaaa ctgaaagatc
2521 tgtagagagt agcagtattt cattggtacc tggtactgat tatggcactc aggaaagtat
```

-continued

```
2581 ctcgttactg gaagttagca ctctagggaa ggcaaaaaca gaaccaaata aatgtgtgag 2641 tcagtgtgca gcatttgaaa accccaaggg actaattcat ggttgttcca agataatag 2701 aaatgacaca gaaggcttta agtatccatt gggacatgaa gttaaccaca gtcgggaaac 2761 aagcatagaa atggaagaaa gtgaacttga tgctcagtat ttgcagaata cattcaaggt 2821 ttcaaagcgc cagtcatttg ctccgttttc aaatccagga aatgcagaag aggaatgtgc 2881 aacattctct gcccactctg ggtccttaaa gaaacaaagt ccaaaagtca cttttgaatg 2941 tgaacaaaag gaagaaaatc aaggaaagaa tgagtctaat atcaagcctg tacagacagt 3001 taatatcact gcaggctttc ctgtggttgg tcagaaagat aagccagttg ataatgccaa 3061 atgtagtatc aaaggaggct ctaggttttg tctatcatct cagttcagag gcaacgaaac 3121 tggactcatt actccaaata acatggact tttacaaaac ccatatcgta taccaccact 3181 ttttcccatc aagtcatttg ttaaaactaa atgtaagaaa atctgctag aggaaaactt 3241 tgaggaacat tcaatgtcac ctgaaagaga atgggaaat gagaacattc caagtacagt 3301 gagcacaatt agccgtaata acattagaga aaatgttttt aaagaagcca gctcaagcaa 3361 tattaatgaa gtaggttcca gtactaatga agtgggctcc agtattaatg aaataggttc 3421 cagtgatgaa acattcaag cagaactagg tagaaacaga gggccaaaat tgaatgctat 3481 gcttagatta ggggttttgc aacctgaggt ctataaacaa agtcttcctg gaagtaattg 3541 taagcatcct gaaataaaaa agcaagaata tgaagaagta gttcagactg ttaatacaga 3601 tttctctcca tatctgattt cagataactt agaacagcct atgggaagta gtcatgcatc 3661 tcaggtttgt tctgagacac ctgatgacct gttagatgat ggtgaaataa aggaagatac 3721 tagttttgct gaaaatgaca ttaaggaaag ttctgctgtt tttagcaaaa gcgtccagaa 3781 aggagagctt agcaggagtc ctagccctt cacccataca catttggctc agggttaccg 3841 aagagggcc aagaaattag agtcctcaga agagaactta tctagtgagg atgaagagct 3901 tcctgcttc caacacttgt tatttggtaa agtaaacaat ataccttctc agtctactag 3961 gcatagcacc gttgctaccg agtgtctgtc taagaacaca gaggagaatt tattatcatt 4021 gaagaatagc ttaaatgact gcagtaacca ggtaatattg gcaaaggcat ctcaggaaca 4081 tcaccttagt gaggaaacaa aatgttctgc tagcttgttt tcttcacagt gcagtgaatt 4141 ggaagacttg actgcaaata caaacaccca ggatcctttc ttgattggtt cttccaaaca 4201 aatgaggcat cagtctgaaa gccagggagt tggtctgagt gacaaggaat tggtttcaga 4261 tgatgaagaa agaggaacgg gcttggaaga aaataatcaa gaagagcaaa gcatggattc 4321 aaacttaggt gaagcagcat ctgggtgtga gagtgaaaca agcgtctctg aagactgctc 4381 agggctatcc tctcagagtg acatttttaac cactcagcag agggatacca tgcaacataa 4441 cctgataaag ctccagcagg aaatggctga actagaagct gtgttagaac agcatgggag 4501 ccagccttct aacagctacc cttccatcat aagtgactct tctgcccttg aggacctgcg 4561 aaatccagaa caaagcacat cagaaaaagc agtattaact tcacagaaaa gtagtgaata 4621 ccctataagc cagaatccag aaggcctttc tgctgacaag tttgaggtgt ctgcagatag 4681 ttctaccagt aaaaataaag aaccaggagt ggaaaggtca tccccttcta aatgcccatc 4741 attagatgat aggtggtaca tgcacagttg ctctgggagt cttcagaata gaaactaccc 4801 atctcaagag gagctcatta aggttgttga tgtggaggag caacagctgg aagagtctgg 4861 gccacacgat ttgacggaaa catcttactt gccaaggcaa gatctagagg gaaccccta 4921 cctggaatct ggaatcagcc tcttctctga tgaccctgaa tctgatcctt ctgaagacag 4981 agcccagag tcagctcgtg ttggcaacat accatcttca acctctgcat tgaaagttcc
```

-continued

```
5041 ccaattgaaa gttgcagaat ctgcccagag tccagctgct gctcatacta ctgatactgc
5101 tgggtataat gcaatggaag aaagtgtgag cagggagaag ccagaattga cagcttcaac
5161 agaaagggtc aacaaaagaa tgtccatggt ggtgtctggc ctgaccccag aagaatttat
5221 gctcgtgtac aagtttgcca gaaaacacca catcacttta actaatctaa ttactgaaga
5281 gactactcat gttgttatga aaacagatgc tgagtttgtg tgtgaacgga cactgaaata
5341 ttttctagga attgcgggag gaaaatgggt agttagctat ttctgggtga cccagtctat
5401 taaagaaaga aaaatgctga atgagcatga ttttgaagtc agaggagatg tggtcaatgg
5461 aagaaaccac caaggtccaa agcgagcaag agaatcccag gacagaaaga tcttcagggg
5521 gctagaaatc tgttgctatg ggcccttcac caacatgccc acagatcaac tggaatggat
5581 ggtacagctg tgtggtgctt ctgtggtgaa ggagctttca tcattcaccc ttggcacagg
5641 tgtccaccca attgtggttg tgcagccaga tgcctggaca gaggacaatg cttccatgc
5701 aattgggcag atgtgtgagg cacctgtggt gacccgagag tgggtgttgg acagtgtagc
5761 actctaccag tgccaggagc tggacaccta cctgatacc cagatccccc acagccacta
5821 ctgactgcag ccagccacag gtacagagcc acaggacccc aagaatgagc ttacaaagtg
5881 gccttccag gccctgggag ctcctctcac tcttcagtcc ttctactgtc ctggctacta
5941 aatattttat gtacatcagc ctgaaaagga cttctggcta tgcaagggtc ccttaaagat
6001 tttctgcttg aagtctccct tggaaatctg ccatgagcac aaaattatgg taattttca
6061 cctgagaaga ttttaaaacc atttaaacgc caccaattga gcaagatgct gattcattat
6121 ttatcagccc tattctttct attcaggctg ttgttggctt agggctggaa gcacagagtg
6181 gcttggcctc aagagaatag ctggtttccc taagtttact tctctaaaac cctgtgttca
6241 caaaggcaga gagtcagacc cttcaatgga aggagagtgc ttgggatcga ttatgtgact
6301 taaagtcaga atagtccttg ggcagttctc aaatgttgga gtggaacatt ggggaggaaa
6361 ttctgaggca ggtattagaa atgaaaagga aacttgaaac ctgggcatgg tggctcacgc
6421 ctgtaatccc agcactttgg gaggccaagg tgggcagatc actggaggtc aggagttcga
6481 aaccagcctg gccaacatgg tgaaacccca tctctactaa aaatacagaa attagccggt
6541 catggtggtg acacctgta atcccagcta ctcaggtggc taaggcagga gaatcacttc
6601 agcccgggag gtggaggttg cagtgagcca agatcatacc acggcactcc agcctgggtg
6661 acagtgagac tgtggctcaa aaaaaaaaaa aaaaaagga aatgaaact agaagagatt
6721 tctaaaagtc tgagatatat ttgctagatt tctaaagaat gtgttctaaa acagcagaag
6781 attttcaaga accggtttcc aaagacagtc ttctaattcc tcattagtaa taagtaaaat
6841 gtttattgtt gtagctctgg tatataatcc attcctctta aaatataaga cctctggcat
6901 gaatatttca tatctataaa atgacagatc ccaccaggaa ggaagctgtt gctttctttg
6961 aggtgatttt tttcctttgc tccctgttgc tgaaaccata cagcttcata ataattttg
7021 cttgctgaag gaagaaaaag tgttttcat aaacccatta tccaggactg tttatagctg
7081 ttggaaggac taggtcttcc ctagccccc cagtgtgcaa gggcagtgaa gacttgattg
7141 tacaaaatac gttttgtaaa tgttgtgctg ttaacactgc aaataaactt ggtagcaaac
7201 acttccaaaa aaaaaaaaa aaaa
```

By "BRCA1 polypeptide" or "BRCA1" is meant a polypeptide or fragment thereof having at least 85% amino acid identity to NCBI Accession No. AAC37594.

An exemplary BRCA1 polypeptide sequence SEQ ID NO. 2 (AAC37594) is provided below:

```
   1 mdlsalrvee vqnvinamqk ilecpiclel ikepvstkcd hifckfcmlk llnqkkgpsq 61 cplcknditk rslqestrfs qlveellkii cafqldtgle yansynfakk ennspehlkd 121 evsiigsmgy rnrakrllqs epenpslget slsvqlsnlg tvrtlrtkqr iqpqktsvyi 181 elgsdssedt vnkatycsvg dgellgitpq gtrdeislds akkaacefse tdvtntehhq 241 psnndlntte kraaerhpek yqgssysnlh vepcgtntha sslghenssl lltkdrmnve 301 kaefcnkskq pglarsqhnr wagsketcnd rrtpstekkv dlnadplcer kewnkqklpc 361 senprdtedv pwitlnssiq kvnewfsrsd ellgsddshd gesesnakva dvldvinevd 421 eysgssekid llasdpheal ickservhsk svesniedki fgktyrkkas lpnlshvten 481 liigafvtep qiigerpltn klkrkrrpts glhpedfikk adlavqktpe minggtngte 541 qngqvmnitn sghenktkgd signeknpnp ieslekesaf ktkaepissss isnmelelni 601 hnskapkknr lrrksstrhi halelvvsrn lsppnctelq idscssseei kkkkynqmpv 661 rhsrnlqlme gkepatgakk snkpnegtsk rhdsdtfpel kltnapgsft kcsntselke 721 fvnpslpree keekletvkv snnaedpkdl mlsgervlqt ersvesssis lvpgtdygtq 781 esisllevst lgkaktepnk cvsqcaafen pkglihgcsk dnrndtegfk yplghevnhs 841 retsiemees eldagylqnt fkvskrqsfa pfsnpgnaee ecatfsahsg slkkqspkvt 901 fecegkeenq gknesnikpv qtvnitagfp vvgqkdkpvd nakcsikggs rfclssqfrg 961 netglitpnk hgllqnpyri pplfpiksfv ktkckknlle enfeehsmsp eremgnenip 1021 stvstisrnn irenvfkeas ssninevgss tnevgssine igssdeniqa elgrnrgpkl 1081 namlrlgvlq pevykgslpg snckhpeikk qeyeevvqtv ntdfspylis dnlegpmgss 1141 hasqvcsetp ddllddgeik edtsfaendi kessavfsks vqkgelsrsp spfththlaq 1201 gyrrgakkle sseenlssed eelpcfghll fgkvnnipsq strhstvate clsknteenl 1261 lslknslndc snqvilakas gehhlseetk csaslfssqc seledltant ntqdpfligs 1321 skqmrhqses qgvglsdkel vsddeergtg leennqeeqs mdsnlgeaas gcesetsyse 1381 dcsglssqsd ilttqqrdtm qhnliklqqe maeleavleq hgsgpsnsyp siisdssale 1441 dlrnpeqsts ekavltsqks seypisqnpe glsadkfevs adsstsknke pgversspsk 1501 cpslddrwym hscsgslqnr nypsqeelik vvdveeqqle esgphdltet sylprqdleg 1561 tpylesgisl fsddpesdps edrapesary gnipsstsal kvpqlkvaes aqspaaahtt 1621 dtagynamee sysrekpelt astervnkrm smvvsgltpe efmlvykfar khhitltnli 1681 teetthvvmk tdaefvcert lkyflgiagg kwvvsyfwvt qsikerkmln ehdfevrgdv 1741 vngrnhqgpk raresqdrki frgleiccyg pftnmptdql ewmvqlcgas vvkelssftl 1801 gtgvhpivvv qpdawtedng fhaigqmcea pvvtrewvld svalyqcgel dtylipqiph 1861 shy
```

A "biomarker" or "marker" as used herein generally refers to a molecule (e.g., polypeptide or polynucleotide) that is differentially present in a sample taken from a subject of one phenotypic status (e.g., having a disease, disorder, or condition) as compared with another phenotypic status (e.g., not having the disease, disorder, or condition). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. As such, biomarkers can find use as markers for, for example, disease (diagnostics), therapeutic effectiveness of a drug (theranostics), and of drug toxicity.

As used herein, the terms "closer follow-up," "increased follow-up," and the like refer to increasing the frequency or scope of evaluating a subject for a disease, disorder, or condition, e.g., non-small cell lung cancer (NSCLC). Increasing the frequency and scope of evaluation can refer to increasing the frequency of patient examinations for monitoring the status/progression of the disease, disorder, or condition status or progression. Increasing the frequency and scope of evaluation can also refer to performing more extensive diagnostic tests on a patient. For example, a chest radiograph is a standard tool used for diagnosing lung cancer. Additional diagnostic tests include CT imaging and bronchoscopy or CT-guided biopsy to obtain a tumor for histopathology. Closer follow-up may be necessary when a subject is identified as having an increased risk for developing a disease, disorder, or condition. Closer follow-up may also be necessary when a subject is identified at being at risk for recurrence.

By "detect" refers to identifying the presence, absence, level, or concentration of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

As used herein, the terms "determining", "assessing", "assaying", "measuring" and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "disease" is meant any condition or disorder that damages or interferes with the normal function of a cell, tissue, or organ. An exemplary disease is cancer.

By "DLC1" is meant a polynucleotide encoding a deleted in liver cancer 1 protein. An exemplary DLC1 nucleic acid molecule is provided at NCBI Accession No. BC049842.

An exemplary DLC1 nucleotide sequence SEQ ID NO. 3 (BC049842) is provided below:

```
   1 tgggcctggt tgtggaggcc ccttttgcaa aacctcagtc tgaatttagt agacagaagt
  61 cactaggaat gccttgacag gatcctgcct tagctaaggc tccctccagc tgcagagggt
 121 gttttttgtta gactcacaca ctgcgtgaaa ctgctcagaa tagagccatg atctcaacca
 181 cgaaatggga acttagattt tggagaaact aacggggacg gacttctttc ctagcctgag
 241 tgttgagcag tgtcatgcct tggcgtttca gctcctcgtt gtctaggtgg tgaaatgaca
 301 gaactcattc gcttctttga ttggtgattt tgaaataatc tttcatcaag ttccatctcc
 361 tttaccctca tatggaatat atctctctgt ctgttgttaa actacgatga catgtctgta
 421 gctatcagaa agagaagctg ggaagaacat gtgacccact ggatgggaca gcctttaat
 481 tctgatgatc gtaacacagc atgtcatcat ggactagtag ctgacagctt gcaggcaagt
 541 atggaaaaag atgcaactct aaatgtggac cgcaaagaga agtgtgtttc actacctgac
 601 tgctgtcatg gatcagagct gagagatttt cctgggaggc caatgggtca tctttcaaag
 661 gatgtggacg aaaatgacag ccatgaaggt gaagatcagt ttctttctct ggaagccagc
 721 acagaaacac tagtgcatgt ttctgatgag gataacaatg ctgatttatg ccttacagat
 781 gataaacagg ttttaaatac ccaagggcag aaaacatcag gccaacatat gatccaagga
 841 gcaggctcct tagaaaaggc actgcccatc atacaaagta accaagtttc ttctaactcc
 901 tggggaatag ctggtgaaac tgaattagca ctggtaaaag aaagtgggga gagaaaagtt
 961 actgactcta taagtaaaag cctggagctt tgcaatgaaa taagcttaag tgaaataaaa
1021 gatgcaccca aagtaaatgc agtggatact ttgaacgtga aagatattgc acctgagaaa
1081 caattgctta actctgctgt aattgctcag caacgaagga aacctgaccc ccctaaagat
1141 gaaaatgaaa gaagcacctg caatgtagta caagatgagt tcttggatac tccttgcaca
1201 aacagaggac tgccattatt aaaaacagat tttggaagct gccttctgca gcctccttcc
1261 tgccccaatg gaatgtcagc tgaaaatggc ctggagaaga gtggtttttc acaacatcaa
1321 aacaaaagtc caccaaaggt caaggcagaa gatggcatgc agtgtttaca attaaaggag
1381 accctggcca cccaggaacc cacagataac caagtcagac ttcgtaagag aaaggaaata
1441 agagaagatc gagatagggc gcggctggac tccatggtgc tgctgattat gaaactggac
1501 cagcttgatc aggacataga aaatgccctc agcaccagct cctctccatc aggcacacca
1561 acaaacctgc ggcggcacgt tcctgatctg gaatcaggat ctgaaagtgg agcagatacc
```

-continued

```
1621 atttcagtaa atcagacacg agtaaatttg tcttctgaca ctgagtccac ggacctccca 1681 tcttccactc cagtagccaa ttctggaacc aaacccaaga ctacggctat tcaaggtatt 1741 tcagagaagg aaaaggctgg taagttgaca ttttggttct gttttctcgc caatctattt 1801 tagaataaat ttcaccttaa aataggcatt ttattaaata tataaaatgt atacatctca 1861 tgaatatatg ggaaaatgtt gtttaaattc tgtaaaagaa atttgttttg ctcaatatgt 1921 aagaaaaata tacgtggttt tctgacataa tgacattgtg ttagaataag atatgtgttt 1981 cttggggtct tccttgtaac tgcaaccaca atttttcttt cttaagcaaa agaattaaat 2041 gttgatcaag gttctgggga atgaatttgg aaattagttg ttaataatta ccaaggttta 2101 tttttactct taatgactta gtagccacag aaaaagatgt aattgatgct taaagctgat 2161 gccatactat caaaaatata gtgatgaagc aatgtgaata attgtattga agaaaaaaat 2221 tatagtattt ttctgtgttc tgtgctttaa ttataattat ttaacagtat tatgggaaat 2281 ggacaaggac tgatgagaaa tgaaaatatg aaaaattaga catggattgg tagatctatg 2341 tgtttttaaa aaatcatact atcttatgtg ttctgtgtaa taaaaacgaa aacagattaa 2401 aggtatatta tctaacttga aaaaaaaaaa aaaaaaaaa aaaaaaaaa a
```

By "DLC1 polypeptide" or "DLC1" is meant a polypeptide or fragment thereof having at least 85% amino acid identity to NCBI Accession No. AAH49842.

An exemplary DLC1 polypeptide sequence SEQ ID NO. 4 (AAH49842) is provided below:

```
  1 msvairkrsw eehvthwmgq pfnsddrnta chhglvadsl gasmekdatl nvdrkekcvs 61 lpdcchgsel rdfpgrpmgh lskdvdends hegedgflsl eastetivhv sdednnadlc 121 ltddkqvint qgqktsgqhm iqgagsleka lpiiqsnqvs snswgiaget elalvkesge 181 rkvtdsisks lelcneisls eikdapkvna vdtlnvkdia pekqllnsav iaqqrrkpdp 241 pkdenerstc nvvqdefldt pctnrglpll ktdfgscllq ppscpngmsa englekssgfs 301 qhqnksppkv kaedgmqclq lketlatqep tdnqvrlrkr keiredrdra rldsmvllim 361 kldqldqdie nalstsssps gtptnlrrhv pdlesgsesg adtisvnqtr vnlssdtest 421 dlpsstpvan sgtkpkttai qgisekekag kltfwfcfla nlf
```

By "drug" is meant a chemical compound, composition, agent (e.g., a pharmaceutical agent) capable of inducing a pharmacological effect in a subject. A drug when properly administered to a patient as a pharmaceutical agent has a desired therapeutic effect.

By "HIF1A" is meant a polynucleotide encoding a hypoxia-inducible factor 1 protein. Exemplary HIF1A nucleic acid molecules are provided at NCBI Accession Nos. NM_001530, NM_181054, and NM_001243084.

An exemplary HIF1A nucleotide sequence SEQ ID NO. 5 (NM_001530) is provided below:

```
  1 gcgcgcgccg gcctgggcag gcgagcgggc gcgctcccgc cccctctccc ctcccgcgc 61 gcccgagcgc gcctccgccc ttgcccgccc cctgacgctg cctcagctcc tcagtgcaca 121 gtgctgcctc gtctgagggg acaggaggat caccctcttc gtcgcttcgg ccagtgtgtc 181 gggctgggcc ctgacaagcc acctgaggag aggctcggag ccgggccgg accccggcga 241 ttgccgcccg cttctctcta gtctcacgag gggtttcccg cctcgcaccc ccacctctgg 301 acttgccttt ccttctcttc tccgcgtgtg gagggagcca gcgcttaggc cggagcgagc
```

-continued

```
 361 ctgggggccg cccgccgtga agacatcgcg gggaccgatt caccatggag ggcgccggcg
 421 gcgcgaacga caagaaaaag ataagttctg aacgtcgaaa agaaaagtct cgagatgcag
 481 ccagatctcg gcgaagtaaa gaatctgaag tttttatga gcttgctcat cagttgccac
 541 ttccacataa tgtgagttcg catcttgata aggcctctgt gatgaggctt accatcagct
 601 atttgcgtgt gaggaaactt ctggatgctg gtgatttgga tattgaagat gacatgaaag
 661 cacagatgaa ttgcttttat ttgaaagcct tggatggttt tgttatggtt ctcacagatg
 721 atggtgacat gatttacatt tctgataatg tgaacaaata catgggatta actcagtttg
 781 aactaactgg acacagtgtg tttgatttta ctcatccatg tgaccatgag gaatgagag
 841 aaatgcttac acacagaaat ggccttgtga aaagggtaa agaacaaaac acacagcgaa
 901 gctttttct cagaatgaag tgtaccctaa ctagccgagg aagaactatg aacataaagt
 961 ctgcaacatg gaaggtattg cactgcacag gccacattca cgtatatgat accaacagta
1021 accaacctca gtgtgggtat aagaaaccac ctatgacctg cttggtgctg atttgtgaac
1081 ccattcctca cccatcaaat attgaaattc ctttagatag caagactttc ctcagtcgac
1141 acagcctgga tatgaaattt tcttattgtg atgaaagaat taccgaattg atgggatatg
1201 agccagaaga acttttaggc cgctcaattt atgaatatta tcatgctttg gactctgatc
1261 atctgaccaa aactcatcat gatatgttta ctaaaggaca agtcaccaca ggacagtaca
1321 ggatgcttgc caaaagaggt ggatatgtct gggttgaaac tcaagcaact gtcatatata
1381 acaccaagaa ttctcaacca cagtgcattg tatgtgtgaa ttacgttgtg agtggtatta
1441 ttcagcacga cttgattttc tcccttcaac aaacagaatg tgtccttaaa ccggttgaat
1501 cttcagatat gaaaatgact cagctattca ccaaagttga atcagaagat acaagtagcc
1561 tctttgacaa acttaagaag gaacctgatg ctttaacttt gctggcccca gccgctggag
1621 acacaatcat atctttagat tttggcagca acgacacaga aactgatgac cagcaacttg
1681 aggaagtacc attatataat gatgtaatgc tcccctcacc caacgaaaaa ttacagaata
1741 taaatttggc aatgtctcca ttacccaccg ctgaaacgcc aaagccactt cgaagtagtg
1801 ctgaccctgc actcaatcaa gaagttgcat taaaattaga accaaatcca gagtcactgg
1861 aactttcttt taccatgccc cagattcagg atcagacacc tagtccttcc gatggaagca
1921 ctagacaaag ttcacctgag cctaatagtc ccagtgaata ttgttttat gtggatagtg
1981 atatggtcaa tgaattcaag ttggaattgg tagaaaaact ttttgctgaa gacacagaag
2041 caaagaaccc attttctact caggacacag atttagactt ggagatgtta gctccctata
2101 tcccaatgga tgatgacttc cagttacgtt ccttcgatca gttgtcacca ttagaaagca
2161 gttccgcaag ccctgaaagc gcaagtcctc aaagcacagt tacagtattc cagcagactc
2221 aaatacaaga acctactgct aatgccacca ctaccactgc caccactgat gaattaaaaa
2281 cagtgacaaa agaccgtatg gaagacatta aatattgat tgcatctcca tctcctaccc
2341 acatacataa agaaactact agtgccacat catcaccata tagagatact caaagtcgga
2401 cagcctcacc aaacagagca ggaaaaggag tcatagaaca gacagaaaaa tctcatccaa
2461 gaagccctaa cgtgttatct gtcgctttga gtcaaagaac tacagttcct gaggaagaac
2521 taaatccaaa gatactagct ttgcagaatg ctcagaaaa gcgaaaaatg gaacatgatg
2581 gttcactttt tcaagcagta ggaattggaa cattattaca gcagccagac gatcatgcag
2641 ctactacatc actttcttgg aaacgtgtaa aaggatgcaa atctagtgaa cagaatggaa
2701 tggagcaaaa gacaattatt ttaatacct ctgatttagc atgtagactg ctggggcaat
```

-continued

```
2761 caatggatga aagtggatta ccacagctga ccagttatga ttgtgaagtt aatgctccta 2821 tacaaggcag cagaaaccta ctgcagggtg aagaattact cagagctttg gatcaagtta 2881 actgagcttt ttcttaattt cattccttt tttggacact ggtggctcat tacctaaagc 2941 agtctattta tattttctac atctaatttt agaagcctgg ctacaatact gcacaaactt 3001 ggttagttca attttgatcc cctttctact taatttacat taatgctctt ttttagtatg 3061 ttctttaatg ctggatcaca gacagctcat tttctcagtt ttttggtatt taaaccattg 3121 cattgcagta gcatcatttt aaaaaatgca cctttttatt tatttatttt tggctaggga 3181 gtttatccct ttttcgaatt attttttaaga agatgccaat ataattttg taagaaggca 3241 gtaacctttc atcatgatca taggcagttg aaaaattttt acaccttttt tttcacattt 3301 tacataaata ataatgcttt gccagcagta cgtggtagcc acaattgcac aatatatttt 3361 cttaaaaaat accagcagtt actcatggaa tatattctgc gtttataaaa ctagttttta 3421 agaagaaatt tttttggcc tatgaaattg ttaaacctgg aacatgacat tgttaatcat 3481 ataataatga ttcttaaatg ctgtatggtt tattatttaa atgggtaaag ccatttacat 3541 aatatagaaa gatatgcata tatctagaag gtatgtggca tttatttgga taaaattctc 3601 aattcagaga aatcatctga tgtttctata gtcactttgc cagctcaaaa gaaaacaata 3661 ccctatgtag ttgtggaagt ttatgctaat attgtgtaac tgatattaaa cctaaatgtt 3721 ctgcctaccc tgttggtata aagatatttt gagcagactg taaacaagaa aaaaaaaatc 3781 atgcattctt agcaaaattg cctagtatgt taatttgctc aaaatacaat gtttgatttt 3841 atgcactttg tcgctattaa catccttttt ttcatgtaga tttcaataat tgagtaattt 3901 tagaagcatt atttaggaa tatatagttg tcacagtaaa tatcttgttt tttctatgta 3961 cattgtacaa atttttcatt ccttttgctc tttgtggttg gatctaacac taactgtatt 4021 gttttgttac atcaaataaa catcttctgt ggaccaggca aaaaaaaaa aaaaaaaaa 4081 aa
```

An exemplary HIF1A nucleotide sequence SEQ ID NO. 6 (NM_181054) is provided below

```
  1 gcgcgcgccg gcctgggcag gcgagcgggc gcgctcccgc ccctctccc ctcccgcgc 61 gcccgagcgc gcctccgccc ttgcccgccc cctgacgctg cctcagctcc tcagtgcaca 121 gtgctgcctc gtctgagggg acaggaggat caccctcttc gtcgcttcgg ccagtgtgtc 181 gggctgggcc ctgacaagcc acctgaggag aggctcggag ccgggcccgg accccggcga 241 ttgccgcccg cttctctcta gtctcacgag gggtttcccg cctcgcaccc ccacctctgg 301 acttgccttt ccttctcttc tccgcgtgtg gagggagcca gcgcttaggc cggagcgagc 361 ctggggccg cccgccgtga agacatcgcg gggaccgatt caccatggag ggcgccggcg 421 gcgcgaacga caagaaaaag ataagttctg aacgtcgaaa agaaaagtct cgagatgcag 481 ccagatctcg gcgaagtaaa gaatctgaag tttttatga gcttgctcat cagttgccac 541 ttccacataa tgtgagttcg catcttgata aggcctctgt gatgaggctt accatcagct 601 atttgcgtgt gaggaaactt ctggatgctg gtgatttgga tattgaagat gacatgaaag 661 cacagatgaa ttgcttttat ttgaaagcct tggatggttt tgttatggtt ctcacagatg 721 atggtgacat gatttacatt tctgataatg tgaacaaata catgggatta actcagtttg 781 aactaactgg acacagtgtg tttgattta ctcatccatg tgaccatgag gaatgagag 841 aaatgcttac acacagaaat ggccttgtga aaaagggtaa agaacaaaac acacagcgaa
```

```
 901 gcttttttct cagaatgaag tgtaccctaa ctagccgagg aagaactatg aacataaagt
 961 ctgcaacatg gaaggtattg cactgcacag gccacattca cgtatatgat accaacagta
1021 accaacctca gtgtgggtat aagaaaccac ctatgacctg cttggtgctg atttgtgaac
1081 ccattcctca cccatcaaat attgaaattc ctttagatag caagactttc ctcagtcgac
1141 acagcctgga tatgaaattt tcttattgtg atgaagaat taccgaattg atgggatatg
1201 agccagaaga acttttaggc cgctcaattt atgaatatta tcatgctttg gactctgatc
1261 atctgaccaa aactcatcat gatatgttta ctaaaggaca agtcaccaca ggacagtaca
1321 ggatgcttgc caaagaggt ggatatgtct gggttgaaac tcaagcaact gtcatatata
1381 acaccaagaa ttctcaacca cagtgcattg tatgtgtgaa ttacgttgtg agtggtatta
1441 ttcagcacga cttgattttc tcccttcaac aaacagaatg tgtccttaaa ccggttgaat
1501 cttcagatat gaaatgact cagctattca ccaaagttga atcagaagat acaagtagcc
1561 tctttgacaa acttaagaag gaacctgatg ctttaacttt gctggcccca gccgctggag
1621 acacaatcat atctttagat tttggcagca acgacacaga aactgatgac cagcaacttg
1681 aggaagtacc attatataat gatgtaatgc tcccctcacc caacgaaaaa ttacagaata
1741 taaatttggc aatgtctcca ttacccaccg ctgaaacgcc aaagccactt cgaagtagtg
1801 ctgaccctgc actcaatcaa gaagttgcat taaaattaga accaaatcca gagtcactgg
1861 aactttcttt taccatgccc cagattcagg atcagacacc tagtccttcc gatggaagca
1921 ctagacaaag ttcacctgag cctaatagtc ccagtgaata ttgttttat gtggatagtg
1981 atatggtcaa tgaattcaag ttggaattgg tagaaaaact ttttgctgaa gacacagaag
2041 caaagaaccc attttctact caggacacag atttagactt ggagatgtta gctccctata
2101 tcccaatgga tgatgacttc cagttacgtt ccttcgatca gttgtcacca ttagaaagca
2161 gttccgcaag ccctgaaagc gcaagtcctc aaagcacagt tacagtattc cagcagactc
2221 aaatacaaga acctactgct aatgccacca ctaccactgc caccactgat gaattaaaaa
2281 cagtgacaaa agaccgtatg gaagacatta aaatattgat tgcatctcca tctcctaccc
2341 acatacataa agaaactact agtgccacat catcaccata tagagatact caaagtcgga
2401 cagcctcacc aaacagagca ggaaaaggag tcatagaaca gacagaaaaa tctcatccaa
2461 gaagccctaa cgtgttatct gtcgctttga gtcaaagaac tacagttcct gaggaagaac
2521 taaatccaaa gatactagct ttgcagaatg ctcagagaaa gcgaaaaatg gaacatgatg
2581 gttcactttt tcaagcagta ggaattattt agcatgtaga ctgctggggc aatcaatgga
2641 tgaaagtgga ttaccacagc tgaccagtta tgattgtgaa gttaatgctc ctatacaagg
2701 cagcagaaac ctactgcagg gtgaagaatt actcagagct ttggatcaag ttaactgagc
2761 ttttctaa tttcattcct ttttttggac actggtggct cattacctaa agcagtctat
2821 ttatattttc tacatctaat tttagaagcc tggctacaat actgcacaaa cttggttagt
2881 tcaattttga tccccttct acttaattta cattaatgct ctttttagt atgttcttta
2941 atgctggatc acagacagct cattttctca gttttttggt atttaaacca ttgcattgca
3001 gtagcatcat tttaaaaaat gcaccttttt atttatttat ttttggctag ggagtttatc
3061 ccttttttcga attattttta agaagatgcc aatataattt tgtaagaag gcagtaacct
3121 ttcatcatga tcataggcag ttgaaaaatt tttacacctt tttttttcaca ttttacataa
3181 ataataatgc tttgccagca gtacgtggta gccacaattg cacaatatat tttcttaaaa
3241 aataccagca gttactcatg gaatatattc tgcgtttata aaactagttt ttaagaagaa
```

-continued

```
3301 attttttttg gcctatgaaa ttgttaaacc tggaacatga cattgttaat catataataa 3361 tgattcttaa atgctgtatg gtttattatt taaatgggta aagccattta cataatatag 3421 aaagatatgc atatatctag aaggtatgtg gcatttattt ggataaaatt ctcaattcag 3481 agaaatcatc tgatgtttct atagtcactt tgccagctca aaagaaaaca atacccctatg 3541 tagttgtgga agtttatgct aatattgtgt aactgatatt aaacctaaat gttctgccta 3601 ccctgttggt ataaagatat tttgagcaga ctgtaaacaa gaaaaaaaaa atcatgcatt 3661 cttagcaaaa ttgcctagta tgttaatttg ctcaaaatac aatgtttgat tttatgcact 3721 ttgtcgctat taacatcctt tttttcatgt agatttcaat aattgagtaa ttttagaagc 3781 attattttag gaatatatag ttgtcacagt aaatatcttg tttttctat gtacattgta 3841 caaattttc attcctttg ctctttgtgg ttggatctaa cactaactgt attgttttgt 3901 tacatcaaat aaacatcttc tgtggaccag gcaaaaaaaa aaaaaaaaa aaaaa
```

An exemplary HIF1A nucleotide sequence SEQ ID NO. 7 (NM_001243084) is provided below:

```
   1 atttgaaaac ttggcaacct tggattggat ggattcatat ttcttagtat agaagttctt 61 gatataactg aaaaattaag ttaaacactt aataagtggt ggttactcag cacttttaga 121 tgctgtttat aatagatgac cttttctaac taatttacag ttttttgaaa gataactgag 181 aggttgaggg acgagatttt tcttcaagca attttttttt tcattttaaa tgagctccca 241 atgtcggagt ttggaaaaca aatttgtctt tttaaaagaa ggtctaggaa actcaaaacc 301 tgaagaattg gaagaaatca gaatagaaaa tggtaggata agttctgaac gtcgaaaaga 361 aaagtctcga gatgcagcca gatctcggcg aagtaaagaa tctgaagttt tttatgagct 421 tgctcatcag ttgccacttc cacataatgt gagttcgcat cttgataagg cctctgtgat 481 gaggcttacc atcagctatt gcgtgtgag gaaacttctg gatgctggtg atttggatat 541 tgaagatgac atgaaagcac agatgaattg cttttatttg aaagccttgg atggttttgt 601 tatggttctc acagatgatg gtgacatgat ttacatttct gataatgtga acaaatacat 661 gggattaact cagtttgaac taactggaca cagtgtgttt gattttactc atccatgtga 721 ccatgaggaa atgagagaaa tgcttacaca cagaaatggc cttgtgaaaa agggtaaaga 781 acaaaacaca cagcgaagct tttttctcag aatgaagtgt accctaacta gccgaggaag 841 aactatgaac ataaagtctg caacatggaa ggtattgcac tgcacaggcc acattcacgt 901 atatgatacc aacagtaacc aacctcagtg tgggtataag aaaccaccta tgacctgctt 961 ggtgctgatt tgtgaaccca ttcctcaccc atcaaatatt gaaattcctt tagatagcaa 1021 gactttcctc agtcgacaca gcctggatat gaaattttct tattgtgatg aaagaattac 1081 cgaattgatg ggatatgagc cagaagaact tttaggccgc tcaatttatg aatattatca 1141 tgctttggac tctgatcatc tgaccaaaac tcatcatgat atgtttacta aaggacaagt 1201 caccacagga cagtacagga tgcttgccaa aagaggtgga tatgtctggg ttgaaactca 1261 agcaactgtc atatataaca ccaagaattc tcaaccacag tgcattgtat gtgtgaatta 1321 cgttgtgagt ggtattattc agcacgactt gattttctcc cttcaacaaa cagaatgtgt 1381 ccttaaaccg gttgaatctt cagatatgaa aatgactcag ctattcacca agttgaatc 1441 agaagataca agtagcctct ttgacaaact taagaaggaa cctgatgctt taactttgct 1501 ggccccagcc gctggagaca caatcatatc tttagatttt ggcagcaacg acacagaaac 1561 tgatgaccag caacttgagg aagtaccatt atataatgat gtaatgctcc cctcacccaa
```

-continued

```
1621 cgaaaaatta cagaatataa atttggcaat gtctccatta cccaccgctg aaacgccaaa 1681 gccacttcga agtagtgctg accctgcact caatcaagaa gttgcattaa aattagaacc 1741 aaatccagag tcactggaac tttcttttac catgccccag attcaggatc agacacctag 1801 tccttccgat ggaagcacta gacaaagttc acctgagcct aatagtccca gtgaatattg 1861 tttttatgtg gatagtgata tggtcaatga attcaagttg gaattggtag aaaaactttt 1921 tgctgaagac acagaagcaa agaacccatt ttctactcag gacacagatt tagacttgga 1981 gatgttagct ccctatatcc caatggatga tgacttccag ttacgttcct tcgatcagtt 2041 gtcaccatta gaaagcagtt ccgcaagccc tgaaagcgca agtcctcaaa gcacagttac 2101 agtattccag cagactcaaa tacaagaacc tactgctaat gccaccacta ccactgccac 2161 cactgatgaa ttaaaaacag tgacaaaaga ccgtatggaa gacattaaaa tattgattgc 2221 atctccatct cctacccaca tacataaaga aactactagt gccacatcat caccatatag 2281 agatactcaa agtcggacag cctcaccaaa cagagcagga aaaggagtca tagaacagac 2341 agaaaaatct catccaagaa gccctaacgt gttatctgtc gctttgagtc aaagaactac 2401 agttcctgag gaagaactaa atccaaagat actagctttg cagaatgctc agagaaagcg 2461 aaaaatggaa catgatggtt cactttttca agcagtagga attggaacat tattacagca 2521 gccagacgat catgcagcta ctacatcact ttcttggaaa cgtgtaaaag gatgcaaatc 2581 tagtgaacag aatggaatgg agcaaaagac aattatttta ataccctctg atttagcatg 2641 tagactgctg gggcaatcaa tggatgaaag tggattacca cagctgacca gttatgattg 2701 tgaagttaat gctcctatac aaggcagcag aaacctactg cagggtgaag aattactcag 2761 agctttggat caagttaact gagctttttc ttaatttcat tccttttttt ggacactggt 2821 ggctcattac ctaaagcagt ctatttatat tttctacatc taattttaga agcctggcta 2881 caatactgca caaacttggt tagttcaatt ttgatcccct ttctacttaa tttacattaa 2941 tgctcttttt tagtatgttc tttaatgctg gatcacagac agctcatttt ctcagttttt 3001 tggtatttaa accattgcat tgcagtagca tcattttaaa aaatgcacct ttttatttat 3061 ttatttttgg ctagggagtt tatcccttt tcgaattatt tttaagaaga tgccaatata 3121 attttgtaa gaaggcagta acctttcatc atgatcatag gcagttgaaa aattttttaca 3181 ccttttttt cacatttac ataaataata atgctttgcc agcagtacgt ggtagccaca 3241 attgcacaat atattttctt aaaaaatacc agcagttact catggaatat attctgcgtt 3301 tataaaacta gttttaagaa gaaattttt tttggcctat gaaattgtta aacctggaac 3361 atgacattgt taatcatata ataatgattc ttaaatgctg tatggtttat tatttaaatg 3421 ggtaaagcca tttacataat atagaaagat atgcatatat ctagaaggta tgtggcattt 3481 atttggataa aattctcaat tcagagaaat catctgatgt ttctatagtc actttgccag 3541 ctcaaaagaa aacaataccc tatgtagttg tggaagttta tgctaatatt gtgtaactga 3601 tattaaacct aaatgttctg cctaccctgt tggtataaag atattttgag cagactgtaa 3661 acaagaaaaa aaaatcatg cattcttagc aaaattgcct agtatgttaa tttgctcaaa 3721 atacaatgtt tgattttatg cactttgtcg ctattaacat cctttttttc atgtagattt 3781 caataattga gtaattttag aagcattatt ttaggaatat atagttgtca cagtaaatat 3841 cttgtttttt ctatgtacat tgtacaaatt tttcattcct tttgctcttt gtggttggat 3901 ctaacactaa ctgtattgtt ttgttacatc aaataaacat cttctgtgga ccaggcaaaa 3961 aaaaaaaaaa aaaaaaaaa
```

By "HIF1A polypeptide" or "HIF1A" is meant a polypeptide or fragment thereof having at least 85% amino acid identity to NCBI Accession Nos. AAF20149, AAF20140, or AAF20139.

An exemplary HIF1A polypeptide sequence SEQ ID NO. 8 (AAF20149) is provided below:

```
  1 megaggandk kkisserrke ksrdaarsrr skesevfyel ahqlplphnv sshldkasvm
 61 rltisylrvr klldagdldi eddmkaqmnc fylkaldgfv mvltddgdmi yisdnvnkym
121 gltqfeltgh svfdfthpcd heemremlth rnglvkkgke qntqrsfflr mkctltsrgr
181 tmniksatwk vlhctgihiv ydtnsnqpqc gykkppmtcl vlicepiphp snieipldsk
241 tflsrhsldm kfsycderit elmgyepeel lgrsiyeyyh aldsdhltkt hhdmftkgqv
301 ttgqyrmlak rggyvwvetq atviyntkns qpqcivcvny vvsgiighdl ifslqqtecv
361 lkpvessdmk mtqlftkves edtsslfdkl kkepdaltll apaagdtiis ldfgsndtet
421 ddqqleevpl yndvmlpspn eklqninlam splptaetpk plrssadpal nqevalklep
481 npeslelsft mpqiqdqtps psdgstrqss pepnspseyc fyvdsdmvne fklelveklf
541 aedteaknpf stqdtdldle mlapyipmdd dfqlrsfdql splesssasp esaspgstvt
601 vfqqtgigep tanattttat tdelktvtkd rmedikilia spspthihke ttsatsspyr
661 dtqsrtaspn ragkgvieqt ekshprspnv lsvalsqrtt vpeeelnpki lalgnagrkr
721 kmehdgslfq avgigtllqg pddhaattsl swkrvkgcks seqngmegkt iiilipsdlac
781 rllggsmdes glpqltsydc evnapiqgsr nllqgeellr aldqvn
```

An exemplary HIF1A polypeptide sequence SEQ ID NO. 9 (AAF20140) is provided below:

```
  1 megaggandk kkisserrke ksrdaarsrr skesevfyel ahqlplphnv sshldkasvm
 61 rltisylrvr klldagdldi eddmkaqmnc fylkaldgfv mvltddgdmi yisdnvnkym
121 gltqfeltgh svfdfthpcd heemremlth rnglvkkgke qntqrsfflr mkctltsrgr
181 tmniksatwk vlhctgihiv ydtnsnqpqc gykkppmtcl vlicepiphp snieipldsk
241 tflsrhsldm kfsycderit elmgyepeel lgrsiyeyyh aldsdhltkt hhdmftkgqv
301 ttgqyrmlak rggyvwvetq atviyntkns qpqcivcvny vvsgiighdl ifslqqtecv
361 lkpvessdmk mtqlftkves edtsslfdkl kkepdaltll apaagdtiis ldfgsndtet
421 ddqqleevpl yndvmlpspn eklqninlam splptaetpk plrssadpal nqevalklep
481 npeslelsft mpqiqdqtps psdgstrqss pepnspseyc fyvdsdmvne fklelveklf
541 aedteaknpf stqdtdldle mlapyipmdd dfqlrsfdql splesssasp esaspgstvt
601 vfqqtgigep tanattttat tdelktvtkd rmedikilia spspthihke ttsatsspyr
661 dtqsrtaspn ragkgvieqt ekshprspnv lsvalsqrtt vpeeelnpki lalgnagrkr
721 kmehdgslfq avgigtllqg pddhaattsl swkrvkgcks seqngmegkt iiilipsdlac
781 rllggsmdes glpqltsydc evnapiqgsr nllqgeellr aldqvn
```

An exemplary HIF1A polypeptide sequence SEQ ID NO. 10 (AAF20139) is provided below:

```
  1 megaggandk kkisserrke ksrdaarsrr skesevfyel ahqlplphnv sshldkasvm
 61 rltisylrvr klldagdldi eddmkaqmnc fylkaldgfv mvltddgdmi yisdnvnkym
121 gltqfeltgh svfdfthpcd heemremlth rnglvkkgke qntqrsfflr mkctltsrgr
```

```
181 tmniksatwk vlhctghihv ydtnsnqpqc gykkppmtcl vlicepiphp snieipldsk 241 tflsrhsldm kfsycderit elmgyepeel lgrsiyeyyh aldsdhltkt hhdmftkgqv 301 ttgqyrmlak rggyvwvetq atviyntkns qpqcivcvny vvsgiighdl ifslqqtecv 361 lkpvessdmk mtqlftkves edtsslfdkl kkepdaltll apaagdtiis ldfgsndtet 421 ddqqleevpl yndvmlpspn eklqninlam splptaetpk plrssadpal nqevalklep 481 npeslelsft mpqiqdqtps psdgstrqss pepnspseyc fyvdsdmvne fklelveklf 541 aedteaknpf stqdtdldle mlapyipmdd dfqlrsfdql splesssasp esaspgstvt 601 vfqqtgigep tanattttat tdelktvtkd rmedikilia spspthihke ttsatsspyr 661 dtqsrtaspn ragkgvieqt ekshprspnv lsvalsqrtt vpeeelnpki lalgnagrkr 721 kmehdgslfq avgigtllqg pddhaattsl swkrvkgcks seqngmegkt iilipsdlac 781 rllggsmdes glpqltsydc evnapiqgsr nllqgeellr aldqvn
```

By "increases" is meant a positive alteration of at least 10%, 25%, 50%, 75%, 100%, 200%, 300%, 400%, 500%, 1000%, or more.

By "miR-21" is meant a microRNA that is encoded by the MIR21 gene. An exemplary miR-21 nucleic acid molecule is provided at NCBI Accession No. NR_029493.1.

An exemplary miR-21 sequence SEQ ID NO. 11 (NR-029493.1) is provided below:

```
 1 tgtcgggtag cttatcagac tgatgttgact gttgaatct catggcaaca ccagtcgatg 61 ggctgtctga ca
```

By "native" is meant endogenous, or originating in a sample.

By "periodic" is meant at regular intervals. Periodic patient monitoring includes, for example, a schedule of tests that are administered daily, bi-weekly, bi-monthly, monthly, bi-annually, or annually.

The term "prediction" is used herein to refer to the likelihood that a patient will have a particular clinical outcome, whether positive or negative. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen. The prediction may include prognostic factors.

The term "positive clinical outcome" means an improvement in any measure of patient status, including those measures ordinarily used in the art, such as an increase in the duration of Recurrence-Free interval (RFI), an increase in the time of Overall Survival (OS), an increase in the time of Disease-Free Survival (DFS), an increase in the duration of Distant Recurrence-Free Interval (DRFI), and the like. An increase in the likelihood of positive clinical outcome corresponds to a decrease in the likelihood of cancer recurrence.

The term "long-term" survival is used herein to refer to survival for at least 3 years, more preferably for at least 5 years.

The term "Recurrence-Free Interval (RFI)" is used herein to refer to time in years to first lung cancer recurrence.

The term "Overall Survival (OS)" is used herein to refer to time in years from treatment or surgery to death from any cause.

The term "Disease-Free Survival (DFS)" is used herein to refer to time in years to lung cancer recurrence or death from any cause.

The term "Distant Recurrence-Free Interval (DRFI)" is used herein to refer to the time (in years) from treatment or surgery to the first anatomically distant cancer recurrence.

As used herein, the terms "prevent," "preventing," "prevention," "prophylactic treatment," and the like, refer to reducing the probability of developing a disease or condition in a subject, who does not have, but is at risk of or susceptible to developing a disease or condition, e.g., NSCLC.

By "reduces" is meant a negative alteration of at least 10%, 25%, 50%, 75%, or 100%.

By "reference" is meant a standard of comparison. For example, the BRCA1, HIF1A, DLC1, XPO1, and/or miR-21 levels present in a patient sample may be compared to the level of the compound(s) in a corresponding healthy cell or tissue or in a diseased cell or tissue (e.g., a cell or tissue derived from a subject having NSCLC).

As used herein, the term "sample" includes a biologic sample such as any tissue, cell, fluid, or other material derived from an organism.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," "treating," "treatment," and the like refer to reducing or ameliorating a disease or condition, e.g., NSCLC, and/or symptoms associated therewith. It will be appreciated that, although not precluded, treating a disease or condition does not require that the disease, condition, or symptoms associated therewith be completely eliminated.

By "XPO1" or "CRM1" is meant a polynucleotide encoding an exportin-1 protein. An exemplary XPO1 nucleic acid molecule is provided at NCBI Accession No. Y08614.

An exemplary XPO1 nucleotide sequence SEQ ID NO. 12 (Y08614) is provided below:

```
   1 aggaaggaag gagcagttgg ttcaatctct ggtaatctat gccagcaatt atgacaatgt
  61 tagcagacca tgcagctcgt cagctgcttg atttcagcca aaaactggat atcaacttat
 121 tagataatgt ggtgaattgc ttataccatg gagaaggagc ccagcaaaga atggctcaag
 181 aagtactgac acatttaaag gagcatcctg atgcttggac aagagtcgac acaattttgg
 241 aattttctca gaatatgaat acgaaatact atggactaca aattttggaa atgtgataa
 301 aaacaaggtg gaagattctt ccaaggaacc agtgcgaagg aataaaaaaa tacgttgttg
 361 gcctcattat caagacgtca tctgacccaa cttgtgtaga gaaagaaaag gtgtatatcg
 421 gaaaattaaa tatgatcctt gttcagatac tgaaacaaga atggcccaaa cattggccaa
 481 cttttatcag tgatattgtt ggagcaagta ggaccagcga aagtctctgt caaaataata
 541 tggtgattct aaaactcttg agtgaagaag tatttgattt ctctagtgga cagataaccc
 601 aagtcaaatc taagcattta aaagacagca tgtgcaatga attctcacag atatttcaac
 661 tgtgtcagtt tgtaatggaa aattctcaaa atgctccact tgtacatgca accttggaaa
 721 cattgctcag atttctgaac tggattcccc tgggatatat ttttgagacc aaattaatca
 781 gcacattgat ttataagttc ctgaatgttc caatgtttcg aaatgtctct ctgaagtgcc
 841 tcactgagat tgctggtgtg agtgtaagcc aatatgaaga acaatttgta acactattta
 901 ctctgacaat gatgcaacta agcagatgc ttcctttaaa taccaatatt cgacttgcgt
 961 actcaaatgg aaaagatgat gaacagaact tcattcaaaa tctcagtttg tttctctgca
1021 cctttcttaa ggaacatgat caacttatag aaaaaagatt aaatctcagg gaaactctta
1081 tggaggccct tcattatatg ttgttggtat ctgaagtaga agaaactgaa atctttaaaa
1141 tttgtcttga atactggaat catttggctg ctgaactcta tagagagagt ccattctcta
1201 catctgcctc tccgttgctt tctggaagtc aacattttga tgttcctccc aggagacagc
1261 tatatttgcc catgttattc aaggtccgtt tattaatggt tagtcgaatg gctaaaccag
1321 aggaagtatt ggttgtagag aatgatcaag gagaagttgt gagagaattc atgaaggata
1381 cagattccat aaatttgtat aagaatatga gggaaacatt ggtttatctt actcatctgg
1441 attatgtaga tacagaaaga ataatgacag agaagcttca caatcaagtg aatggtacag
1501 agtggtcatg gaaaaatttg aatacattgt gttgggcaat aggctccatt agtggagcaa
1561 tgcatgaaga ggacgaaaaa cgatttcttg ttactgttat aaaggatcta ttaggattat
1621 gtgaacagaa aagaggcaaa gataataaag ctattattgc atcaaatatc atgtacatag
1681 taggtcaata cccacgtttt ttgagagctc actggaaatt tctgaagact gtagttaaca
1741 agctgttcga attcatgcat gagacccatg atggagtcca ggatatggct tgtgatactt
1801 tcattaaaat agcccaaaaa tgccgcaggc atttcgttca ggttcaggtt ggagaagtga
1861 tgccatttat tgatgaaatt ttgaacaaca ttaacactat tatttgtgat cttcagcctc
1921 aacaggttca tacgttttat gaagctgtgg ggtacatgat tggtgcacaa acagatcaaa
1981 cagtacaaga gcacttgata gaaaagtaca tgttactccc taatcaagtg tgggatagta
2041 taatccagca ggcaaccaaa aatgtggata tactgaaaga tcctgaaaca gtcaagcagc
2101 ttggtagcat tttgaaaaca aatgtgagag cctgcaaagc tgttggacac ccctttgtaa
2161 ttcagcttgg aagaatttat ttagatatgc ttaatgtata caagtgcctc agtgaaaata
2221 tttctgcagc tatccaagct aatggtgaaa tggttacaaa gcaaccattg attagaagta
2281 tgcgaactgt aaaaagggaa actttaaagt taatatctgg ttgggtgagc cgatccaatg
```

-continued

```
2341 atccacagat ggtcgctgaa aatttgttc ccctctgtt ggatgcagtt ctcattgatt 2401 atcagagaaa tgtcccagct gctagagaac cagaagtgct tagtactatg gccataattg 2461 tcaacaagtt aggggacat ataacagctg aaatacctca aatatttgat gctgttttg 2521 aatgcacatt gaatatgata ataaggact ttgaagaata tcctgaacat agaacgaact 2581 ttttcttact acttcaggct gtcaattctc attgtttccc agcattcctt gctattccac 2641 ctacacagtt taaacttgtt ttggattcca tcatttgggc tttcaaacat actatgagga 2701 atgtcgcaga tacgggctta cagatacttt ttacactctt acaaaatgtt gcacaagaag 2761 aagctgcagc tcagagtttt tatcaaactt attttgtga tattctccag catatctttt 2821 ctgttgtgac agacacttca catactgctg gtttaacaat gcatgcatca attcttgcat 2881 atatgtttaa tttggttgaa gaaggaaaaa taagtacatc attaaatcct ggaaatccag 2941 ttaacaacca aatctttctt caggaatatg tggctaatct ccttaagtcg gccttccctc 3001 acctacaaga tgctcaagta aagctctttg tgacagggct tttcagctta aatcaagata 3061 ttcctgcttt caaggaacat ttaagagatt tcctagttca aataaaggaa tttgcaggtg 3121 aagacacttc tgatttgttt ttggaagaga gagaaatagc cctacggcag gctgatgaag 3181 agaaacataa acgtcaaatg tctgtccctg gcatctttaa tccacatgag attccagaag 3241 aaatgtgtga ttaaaatcca aattcatgct gtttttttc tctgcaactc cgttagcaga 3301 ggaaaacagc atgtgggtat ttgtcgacca aaatgatgcc aatttgtaaa ttaaaatgtc 3361 acctagtggc cctttttctt atgtgttttt ttgtataaga aattttctgt gaaatatcct 3421 tccattgttt aagcttttgt tttggtcatc tttatttagt ttgcatgaag ttgaaaatta 3481 aggcattttt aaaaatttta cttcatgccc attttgtgg ctgggctggg gggaggaggc 3541 aaattcaatt tgaacatata cttgtaattc taatgcaaaa ttatacaatt tttcctgtaa 3601 acaataccaa tttttaatta gggagcattt tccttctagt ctatttcagc ctagaagaaa 3661 agataatgag taaaacaaat tgcgttgttt aaaggattat agtgctgcat tgtctgaagt 3721 tagcacctct tggactgaat cgtttgtcta gactacatgt attacaaagt ctctttggca 3781 agattgcagc aagatcatgt gcatatcatc ccattgtaaa gcgacttcaa aaatatggga 3841 acacagttag ttatttttac acagttcttt ttgttttgt gtgtgtgtgc tgtcgcttgt 3901 cgacaacagc tttttgtttt cctcaatgag gagtgttgct catttgtgag ccttcattaa 3961 ctcgaagtga aatggttaaa aatatttatc ctgttagaat aggctgcatc ttttaacaa 4021 ctcattaaaa aacaaaacaa ctctggcttt tgagatgact tatactaatt tacattgttt 4081 accaagctgt agtgctttaa gaacactact taaaaagcaa aataaacttg gtttacattt 4141 aaaaaaa
```

By "XPO1 polypeptide," "XPO1," "CRM1 polypeptide," or "CRM1" is meant a polypeptide or fragment thereof having at least 85% amino acid identity to NCBI Accession No. AAH32847.

An exemplary HIF1A polypeptide sequence SEQ ID NO. 13 (AAH32847) is provided below:

```
  1 mpaimtmlad haarcilldf sqkldinlld nvvnclyhge gaqqrmagev thlkehpdaw 61 trvdtilefs qnmntkyygl qilenviktr wkilprnqce gikkyvvgli iktssdptcv 121 ekekvyigkl nmilvgilkg ewpkhwptfi sdivgasrts eslcqnnmvi lkllseevfd 181 fssgqitqvk skhlkdsmcn efsgifqlcq fvmensgnap lvhatletll rflnwiplgy 241 ifetklistl iykflnvpmf rnvslkclte iagvsysqye eqfvtlftlt mmqlkgmlpl
```

-continued

```
301 ntnirlaysn gkddeqnfiq nlslflctfl kehdqliekr lnlretlmea lhymllvsev 361 eeteifkicl eywnhlaael yrespfstsa spllsgsqhf dvpprrglyl pmlfkvrllm 421 vsrmakpeev lvvendqgev vrefmkdtds inlyknmret lvylthldyv dterimtekl 481 hnqvngtews wknlnticwa igsisgamhe edekrflvtv ikdllglceq krgkdnkaii 541 asnimyivgq yprflrahwk flktvvnklf efmhethdgv qdmacdtfik iaqkcrrhfv 601 qvqvgevmpf ideilnnint iicdlqpqqv htfyeavgym igaqtdqtvg ehliekymll 661 pnqvwdsiiq qatknvdilk dpetvkqlgs ilktnvrack avghpfviql griyldmlnv 721 ykclsenisa aigangemvt kqplirsmrt vkretlklis gwvsrsndpq mvaenfvppl 781 ldavlidyqr nvpaarepev lstmaiivnk lgghitaeip qifdavfect lnminkdfee 841 ypehrtnffl llgavnshcf paflaipptq fklvldsiiw afkhtmrnva dtglgilftl 901 lqnvageeaa aqsfyqtyfc dilqhifsvv tdtshtaglt mhasilaymf nlveegkist 961 slnpgnpvnn giflgeyvan llksafphlq daqvklfvtg lfslnqdipa fkehlrdflv 1021 qikefagedt sdlfleerei alrqadeekh krqmsvpgif npheipeemc d
```

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compounds, compositions, or methods provided herein can be combined with one or more of any of the other compositions and methods provided herein.

DESCRIPTION OF THE DRAWINGS

FIG. 11 includes a table showing the Cox regression analysis of the four gene signature and miR-21 expression for the Japan and US/Norway cohorts (AJCC 7th edition). In this table, miR-21 was measured with qRT-PCR in the Japan cohort and with Nanostring human microRNA assays in the US/Norway cohorts.

FIG. 20 (A & B) is a Table showing a list of retrieved datasets and whether they were included or excluded based on selection criteria.

DETAILED DESCRIPTION OF THE INVENTION

Figure 1:
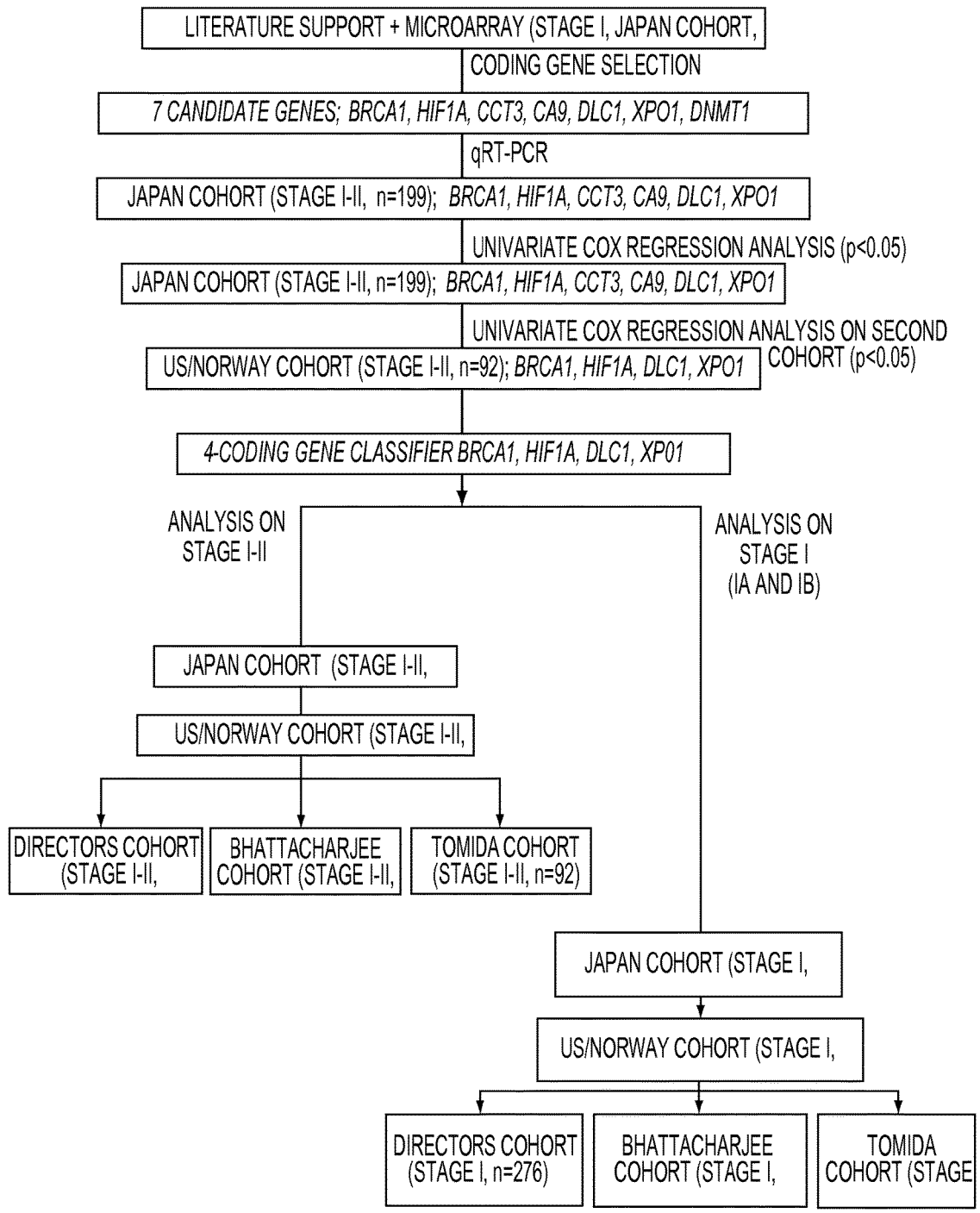
FIG. 1 includes a schematic of the study for the identification of the four coding gene signature.

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2.sup.nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4.sup.th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

This invention is based, at least in part, on the discovery that BRCA1, HIF1A, DLC1, XPO1, and miR-21 are biomarkers for early stage lung cancer. Accordingly, the invention provides methods and kits that are useful in the diagnosis, treatment, and prevention of early stage lung cancer. The invention further provides methods and kits for evaluating therapies for treating a patient identified as having early stage lung cancer.

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and reverse transcription polymerase chain reaction (RT-PCR) (Weis et al., Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Protein coding and non-coding gene expression profiling by means of microarrays and quantitative reverse transcriptase polymerase chain reaction (qRT-PCR), have been used to develop prognostic classifiers for patients with various types of cancer (Ramaswamy, S. et al., *Nat. Genet.* 33:49-54 (2003); Ludwig, J. A. et al., *Nat. Rev. Cancer* 5:845-56 (2005); Lossos, I. S. et al., *N. Engl. J. Med.* 350:1828-37 (2004); Beer, D. G. et al., *Nat. Med.* 8:816-24 (2002); Tsao, M. S. et al., *N. Engl. J. Med.* 353:133-44 (2005); and Endoh, H. et al., *J. Clin. Oncol.* 22:811-9 (2004)), including stage I lung cancer (Lu, Y. et al., *PLoS Med.* 3:e467 (2006); Bianchi, F. et al. *J. Clin. Invest.* 117:3436-44 (2007); Lee, E. S. et al., *Clin. Cancer Res.* 14:7397-404 (2008); Raponi, M. et al., *Cancer Res.* 66:7466-72 (2006); Chen, H. Y. et al., *N. Engl. J. Med.* 356:11-20 (2007); Tomida, S. et al., *J. Clin. Oncol.* 27:2793-9 (2009); Wan, Y. W. et al., *PLoS One* 5:e12222 (2010); and Saito, M. et al., *Clin. Cancer Res.* 17:1875-82 (2011). In many cases, the associations reported in single cohorts have failed to validate in additional patient populations. See Subramanian, J. et al., *J. Natl. Cancer Inst.* 102:464-74 (2010).

In order to establish a robust and broadly useful prognostic biomarker for stage I lung cancer patients, a prognostic coding gene expression classifier for stage I lung cancer was developed. The gene classifier was developed using genes selected based on a combination of microarray data and support from the literature, and its performance was tested in multiple, independent patient cohorts. This strategy incorporated the mining of publicly-available gene expression datasets with clinical information and is illustrated in FIG. 1. In addition, the coding gene-classifier was refined by combining it with previously acquired data from expression analysis of a non-protein coding microRNA, miR-21. Saito, M. et al., *Clin. Cancer Res.* 17:1875-82 (2011). Use of the gene classifier in combination with miR-21 resulted in improved associations with cancer-specific mortality in stage I, lung adenocarcinoma. Therefore, the gene classifier, optionally in combination with miR-21, will have diagnostic value for the treatment of lung cancer.

Diagnostics and Diagnostic Assays

Lung cancer is a disease characterized by uncontrolled cell growth in lung tissues, and it is the most common type of cancer in both men and women in the United States. According to the American Cancer Society, almost 220,000 people are diagnosed with lung cancer each year.

There are two main types of lung cancer—small cell lung cancer (SCLC) and non-small cell lung cancer (NSCLC). NSCLC makes up 80-85% of lung cancer cases in the United States, and the types of NSCLC are named for the kinds of cells found in the cancer and how the cells look under a microscope. There are three major types of NSCLC: (i) squamous cell carcinoma, which begins in squamous cells that are thin, flat cells that look like fish scales; (ii) large cell carcinoma, which begins in several types of large lung cells; and (iii) adenocarcinoma, which begins in the cells that line the alveoli of the lung.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC (stage 1A in which tumors are localized and less than 3 cm; or stage 1B in which tumors are localized and greater than 3 cm) can be potentially cured by surgical resection to remove the tumor, but the current diagnostic modalities are not able to predict which patients will recur after surgery. Moreover, even with successful surgery, lung cancer can recur locally or at distant sites in roughly one third of patients.

Although the use of adjuvant therapies (e.g., radiation and chemotherapy) to treat early stage lung cancer is controversial, individuals at high risk of recurrence will benefit from the use of additional therapies. Accordingly, it is desirable to identify early stage lung cancer patients at high risk for recurrence in order to more closely monitor and administer adjuvant therapy to these individuals. To this effect, the present invention provides novel gene classifiers that can identify individuals having early stage lung cancer that will benefit from adjuvant therapy (i.e., non-surgical therapies such as radiation and chemotherapy).

Accordingly, the present invention features methods for determining the prognosis of a subject with lung cancer. In embodiments, the methods involve detecting the levels of BRCA1, HIF1A, DLC1, and XPO1 in a sample obtained from the subject. The methods further involve comparing the levels of BRCA1, HIF1A, DLC1, and XPO1 to a reference and identifying the subject as having an adverse prognosis when the levels of BRCA1, HIF1A, and XPO1 are increased relative to the reference or when the level of DLC1 is decreased relative to the reference. In related embodiments, the reference is the levels of BRCA1, HIF1A, DLC1, and XPO1 in a healthy control. In some related embodiments, the subject is identified as having an adverse prognosis when the levels of BRCA1, HIF1A, and XPO1 are increased relative to the reference and when the level of DLC1 is decreased relative to the reference. In yet other related embodiments, the subject is identified as having an adverse prognosis when the subject has a higher classifier score of (0.104×BRCA1)+(0.133×HIF1A)+(−0.246×DLC1)+ (0.378×XPO1) relative to the reference.

In embodiments, the methods involve detecting the levels of BRCA1, HIF1A, DLC1, XPO1, and miR-21 in a sample obtained from the subject. The methods further involve comparing the levels of BRCA1, HIF1A, DLC1, XPO1, and miR-21 to a reference and identifying the subject as having an adverse prognosis when the levels of BRCA1, HIF1A, XPO1, and miR-21 are increased relative to the reference or when the level of DLC1 is decreased relative to the reference. In related embodiments, the reference is the levels of BRCA1, HIF1A, DLC1, XPO1, and miR-21 in a healthy control. In some related embodiments, the subject is identified as having an adverse prognosis when the levels of BRCA1, HIF1A, XPO1, and miR-21 are increased relative to the reference and when the level of DLC1 is decreased relative to the reference. In yet other related embodiments, the subject is identified as having an adverse prognosis when the subject has a higher classifier score of (0.104×BRCA1)+(0.133×HIF1A)+(−0.246×DLC1)+(0.378×XPO1) relative to the reference and when the subject has a higher miR-21 level relative to the reference.

In aspects, the invention features methods for diagnosing a subject at risk of developing lung cancer. In embodiments, the methods involve detecting the levels of BRCA1, HIF1A, DLC1, and XPO1 in a sample obtained from the subject. The methods further involve comparing the levels of BRCA1, HIF1A, DLC1, and XPO1 to a reference and identifying the subject as at risk for developing lung cancer when the levels of BRCA1, HIF1A, and XPO1 are increased relative to the reference or when the level of DLC1 is decreased relative to the reference. In related embodiments, the reference is the levels of BRCA1, HIF1A, DLC1, and XPO1 in a healthy control. In some related embodiments, the subject is identified as at risk for developing lung cancer when the levels of BRCA1, HIF1A, and XPO1 are increased relative to the reference and when the level of DLC1 is decreased relative to the reference. In yet other related embodiments, the subject is identified as at risk for developing lung cancer when the subject has a higher classifier score of (0.104×BRCA1)+(0.133×HIF1A)+(−0.246×DLC1)+(0.378×XPO1) relative to the reference.

In embodiments, the methods involve detecting the levels of BRCA1, HIF1A, DLC1, XPO1, and miR-21 in a sample obtained from the subject. The methods further involve comparing the levels of BRCA1, HIF1A, DLC1, XPO1, and miR-21 to a reference and identifying the subject as at risk for developing lung cancer when the levels of BRCA1, HIF1A, XPO1, and miR-21 are increased relative to the reference or when the level of DLC1 is decreased relative to the reference. In related embodiments, the reference is the levels of BRCA1, HIF1A, DLC1, XPO1, and miR-21 in a healthy control. In some related embodiments, the subject is identified as at risk for developing lung cancer when the levels of BRCA1, HIF1A, XPO1, and miR-21 are increased relative to the reference and when the level of DLC1 is decreased relative to the reference. In yet other related embodiments, the subject is identified as at risk for developing lung cancer when the subject has a higher classifier score of (0.104×BRCA1)+(0.133×HIF1A)+(−0.246×DLC1)+(0.378×XPO1) relative to the reference and when the subject has a higher miR-21 level relative to the reference.

In aspects, the invention features methods for diagnosing a risk of lung cancer recurrence in a subject. In embodiments, the methods involve detecting the levels of BRCA1, HIF1A, DLC1, and XPO1 in a sample obtained from the subject. The methods further involve comparing the levels of BRCA1, HIF1A, DLC1, and XPO1 to a reference and identifying the subject as at risk for recurrence of lung cancer when the levels of BRCA1, HIF1A, and XPO1 are increased relative to the reference or when the level of DLC1 is decreased relative to the reference. In related embodiments, the reference is the levels of BRCA1, HIF1A, DLC1, and XPO1 in a healthy control. In some related embodiments, the subject is identified as at risk for recurrence of lung cancer when the levels of BRCA1, HIF1A, and XPO1 are increased relative to the reference and when the level of DLC1 is decreased relative to the reference. In yet other related embodiments, the subject is identified as at risk for recurrence of lung cancer when the subject has a higher classifier score of (0.104×BRCA1)+(0.133×HIF1A)+(−0.246×DLC1)+(0.378×XPO1) relative to the reference.

In embodiments, the methods involve detecting the levels of BRCA1, HIF1A, DLC1, XPO1, and miR-21 in a sample obtained from the subject. The methods further involve comparing the levels of BRCA1, HIF1A, DLC1, XPO1, and miR-21 to a reference and identifying the as at risk for recurrence of lung cancer when the levels of BRCA1, HIF1A, XPO1, and miR-21 are increased relative to the reference or when the level of DLC1 is decreased relative to the reference. In related embodiments, the reference is the levels of BRCA1, HIF1A, DLC1, XPO1, and miR-21 in a healthy control. In some related embodiments, the subject is identified as at risk for recurrence of lung cancer when the levels of BRCA1, HIF1A, XPO1, and miR-21 are increased relative to the reference and when the level of DLC1 is decreased relative to the reference. In yet other related embodiments, the subject is identified as at risk for recurrence of lung cancer when the subject has a higher classifier score of (0.104×BRCA1)+(0.133×HIF1A)+(−0.246×DLC1)+(0.378×XPO1) relative to the reference and when the subject has a higher miR-21 level relative to the reference.

In aspects, the invention features methods for selecting an appropriate therapy for a subject. In embodiments, the methods involve detecting the levels of BRCA1, HIF1A, DLC1, and XPO1 in a sample obtained from the subject. The methods further involve comparing the levels of BRCA1, HIF1A, DLC1, and XPO1 to a reference, wherein an increase in the levels of BRCA1, HIF1A, and XPO1 or a decrease in DLC1 relative to the reference indicates that lung cancer therapy is appropriate for the subject. In related embodiments, the reference is the levels of BRCA1, HIF1A, DLC1, and XPO1 in a healthy control. In some related embodiments, lung cancer therapy is identified as appropriate for the subject when the subject has a higher classifier score of (0.104×BRCA1)+(0.133×HIF1A)+(−0.246×DLC1)+(0.378×XPO1) relative to the reference.

In embodiments, the methods involve detecting the levels of BRCA1, HIF1A, DLC1, XPO1, and miR-21 in a sample obtained from the subject. The methods further involve comparing the levels of BRCA1, HIF1A, DLC1, XPO1, and miR-21 to a reference, wherein an increase in the levels of BRCA1, HIF1A, XPO1, and miR-21 or a decrease in DLC1 relative to the reference indicates that lung cancer therapy is appropriate for the subject. In related embodiments, the reference is the levels of BRCA1, HIF1A, DLC1, XPO1, and miR-21 in a healthy control. In some related embodiments, lung cancer therapy is identified as appropriate for the subject when the subject has a higher classifier score of (0.104×BRCA1)+(0.133×HIF1A)+(−0.246×DLC1)+(0.378×XPO1) relative to the reference and when the subject has a higher miR-21 level relative to the reference.

In any of the above aspects and embodiments, the sample may be a biological sample from the subject. The biological sample can be a tissue sample (e.g., cell sample, biopsy sample, and the like) or a bodily fluid, including, but not limited to, blood, blood serum, plasma, cerebrospinal fluid, saliva, and urine. Samples can optionally be treated to enrich for the biomarker(s) using enrichment and separation methods well known in the art. In embodiments, the sample is a tissue sample obtained from the lung.

In any of the above aspects and embodiments, the subject is assigned to closer follow-up when identified as having an adverse prognosis, at risk of developing lung cancer, at risk of recurrence lung cancer, or appropriate for lung cancer therapy. In embodiments, the subject is assigned to more frequent screenings when identified as having an adverse prognosis, at risk of developing lung cancer, at risk of recurrence, or appropriate for lung cancer therapy. In some embodiments, the subject is assigned to more frequent CT scans when identified as having an adverse prognosis, at risk of developing lung cancer, at risk of recurrence, or appropriate for lung cancer therapy.

In any of the above aspects and embodiments, the subject is selected for a clinical trial when identified as having an adverse prognosis, at risk of developing lung cancer, at risk of recurrence, or appropriate for lung cancer therapy.

In any of the above aspects and embodiments, the subject can be administered adjuvant chemotherapy when identified as having an adverse prognosis, at risk of developing lung cancer, at risk of recurrence lung cancer, or appropriate for lung cancer therapy. The adjuvant chemotherapy can be any chemotherapeutic agent well known in the art. See, e.g., *Anticancer Drugs: Design, Delivery and Pharmacology* (*Cancer Etiology, Diagnosis and Treatments*) (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); *Chemotherapy and Biotherapy Guidelines and Recommendations for Practice* (eds. Polovich, M. et al.) (Oncology Nursing Society, 2009); *Physicians' Cancer Chemotherapy Drug Manual* 2012 (eds. Chu, E. & DeVita, Jr., V. T.) (Jones & Bartlett Learning, 2011); *DeVita, Hellman, and Rosenberg's Cancer: Principles and Practice of Oncology* (eds. DeVita, Jr., V. T. et al.) (Lippincott Williams & Wilkins, 2011); and *Clinical Radiation Oncology* (eds. Gunderson, L. L. & Tepper, J. E.) (Saunders) (2011), the contents of which are hereby incorporated by references in their entirety. Exemplary chemotherapeutic agents include, but are not limited to, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etoposide, Everolimus, Exemestane, Filgrastim, Floxuridine, Fludarabine, Fluorouracil, Fluoxymesterone, Flutamide, Gefitinib, Gemcitabine, Gemtuzumab ozogamicin, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trastuzumab, Tretinoin, Valrubicin, VEGF inhibitors and traps, Vinblastine, Vincristine, Vindesine, Vinorelbine, and Vorinostat.

In any of the above aspects and embodiments, the subject can be administered adjuvant radiotherapy when identified as having an adverse prognosis, at risk of developing lung cancer, at risk of recurrence lung cancer, or appropriate for lung cancer therapy.

In any of the above aspects and embodiments, the lung cancer is non-small cell lung cancer (NSCLC). In embodiments, the lung cancer is stage 1A or stage 1B NSCLC.

In any of the above aspects and embodiments, the subject is a mammal (e.g., human).

In any of the above aspects and embodiments, the level of BRCA1, HIF1A, XPO1, and/or miR-21 is increased 1.5, 2, 2.5, 3, 3.5, 4, 5, 6, 7, 8, 9, 10, 11, 12, 13, 14, 15-fold or more relative to the reference. In any of the above aspects and embodiments, the level of DLC1 is decreased 1.5, 2, 2.5, 3, 3.5, 4, 5, 6, 7, 8, 9, 10, 11, 12, 13, 14, 15-fold or more relative to the reference.

In any of the above aspects and embodiments, the BRCA1, HIF1A, DLC1, XPO1, and/or miR-21 profile may be obtained from a subject sample and compared to a reference profile obtained from a reference population, so that it is possible to classify the subject as belonging to or not belonging to the reference population. The correlation may take into account the presence or absence of the markers in a test sample and the frequency of detection of the same markers in a control. The correlation may take into account both of such factors to facilitate determination of the status.

Detection of BRCA1, HIF1A, DLC1, XPO1, and miR-21

Any suitable method can be used to detect BRCA1, HIF1A, DLC1, XPO1, and/or miR-21. Successful practice of the invention can be achieved with one or a combination of methods that can detect and, in embodiments, quantify the markers.

Detection of the markers can be conducted in the same or different samples, the same or separate assays, and may be conducted in the same or different reaction mixtures. Where the markers are assayed in different samples, the samples are usually obtained from the subject during the same procedure (e.g., blood draw, urine collection, tissue extraction, and the like) or with only a relative short time intervening so as to avoid an incorrect result due to passage of time. Where the markers are detected in separate assays, the samples assayed are can be derived from the same or different samples obtained from the subject to be tested.

BRCA1, HIF1A, DLC1, XPO1, and/or miR-21 can be detected using one or more methods well known in the art, including, without limit, mass spectrometry, chromatography, spectroscopy (e.g., NMR), elemental analysis, conventional chemical methods, immunoassays, microarray, RT-PCR (e.g., qRT-PCR), nanostring assay, in situ hybridization, and the like.

In embodiments, the markers are detected using mass spectrometry. Mass spectrometry-based methods exploit the differences in mass of biomarkers to facilitate detection. Mass spectrometry can be combined with other assays, e.g., resolving the analyte in a sample by one or two passes through liquid or gas chromatography followed by mass spectrometry analysis. Methods for preparing a biological sample for analysis by mass spectrometry are well known in the art. Suitable mass spectrometers for use include, without limit, electrospray ionization mass spectrometry (ESI-MS), ESIMS/MS, ESI-MS/(MS)n (n is an integer greater than zero), matrix-assisted laser desorption ionization time-of-flight mass spectrometry (MALDI-TOF-MS), electron impact ionization mass spectrometry (EI-MS), chemical ionization mass spectrometry (CI-MS), surface-enhanced laser desorption/ionization time-of-flight mass spectrometry (SELDI-TOF-MS), desorption/ionization on silicon (DIOS), secondary ion mass spectrometry (SIMS), quadrupole time of-flight (Q-TOF), atmospheric pressure chemical ionization mass spectrometry (APCI-MS), APCI-MS/MS, APCI(MS) 11, atmospheric pressure photoionization mass spectrometry (APPI-MS), APPI-MS/MS, APPI-(MS), quadrupole, fourier transform mass spectrometry (FTMS), ion trap, and hybrids of these methods, e.g., electrospray ionization quadrupole time-of-flight mass spectrometry (UPLC-ESI-QTOFMS) and two-dimensional gas chromatography electron impact ionization mass spectrometry (GC×GC-EI-MS).

The methods may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454 and 20050035286; U.S. Pat. No. 5,800,979; and the references disclosed therein.

Samples are collected on a collection layer. They may then be analyzed by a spectroscopic method based on matrix-assisted laser desorption/ionization (MALDI), electrospray ionization (ESI), and the like.

Other techniques for improving the mass accuracy and sensitivity of the MALDI-TOF MS can be used to analyze the analytes obtained on the collection membrane. These include the use of delayed ion extraction, energy reflectors and ion-trap modules. In addition, post source decay and MS--MS analysis are useful to provide further structural analysis. With ESI, the sample is in the liquid phase and the analysis can be by ion-trap, TOF, single quadrupole or multi-quadrupole mass spectrometers. The use of such devices (other than a single quadrupole) allows MS--MS or MS$^n$ analysis to be performed. Tandem mass spectrometry allows multiple reactions to be monitored at the same time.

Capillary infusion may be employed to introduce the marker to a desired MS implementation, for instance, because it can efficiently introduce small quantities of a sample into a mass spectrometer without destroying the vacuum. Capillary columns are routinely used to interface the ionization source of a MS with other separation techniques including gas chromatography (GC) and liquid chromatography (LC). GC and LC can serve to separate a solution into its different components prior to mass analysis. Such techniques are readily combined with MS, for instance. One variation of the technique is that high performance liquid chromatography (HPLC) can now be directly coupled to mass spectrometer for integrated sample separation/and mass spectrometer analysis.

Quadrupole mass analyzers may also be employed as needed to practice the invention. Fourier-transform ion cyclotron resonance (FTMS) can also be used for some invention embodiments. It offers high resolution and the ability of tandem MS experiments. FTMS is based on the principle of a charged particle orbiting in the presence of a magnetic field. Coupled to ESI and MALDI, FTMS offers high accuracy with errors as low as 0.001%.

In embodiments, the diagnostic methods of the invention may further comprise identifying significant peaks from combined spectra. The methods may also further comprise searching for outlier spectra. In other embodiments, the methods of the invention further comprise determining distant dependent K-nearest neighbors.

In embodiments, an ion mobility spectrometer can be used to detect and characterize the biomarker(s). The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a biomarker or other substances in a sample. One advantage of ion mobility spectrometry is that it can operate at atmospheric pressure.

In embodiments, the procedure is electrospray ionization quadrupole mass spectrometry with time of flight (TOF) analysis, known as UPLC-ESI-QTOFMS.

In embodiments, detection of the markers involves chemical methods well known in the art. In embodiments, the chemical method is chemical extraction. In embodiments, the chemical method is chemical derivitization.

In embodiments, detection of the markers involves use of chromatography methods that are well known in the art. Such chromatography methods include, without limit, column chromatography, ion exchange chromatography, hydrophobic (reverse phase) liquid chromatography, or other chromatography, such as thinlayer, gas, or liquid chromatography (e.g., high-performance liquid chromatography), or any combination thereof.

In embodiments, detection of the markers involves use of spectroscopy methods that are well known in the art. Such chromatography methods include, without limit, NMR, IR, and the like.

In embodiments, detection of the markers involves elemental analysis methods that are well known in the art. Such elemental analysis methods include, without limit, combustion analysis, gravimetry, atomic spectroscopy, and the like.

In embodiments, detection of the markers involves use of immunoassays. In embodiments, the immunoassays involve the use of antibodies. Suitable immunoassays include, without limit, ELISA, flow chamber adhesion, colorimetric assays (e.g., antibody based colorimetric assays), biochip (e.g., antibody based biochip), and the like.

In embodiments, detection of the markers involves use of microarrays or quantitative RT-PCR. See, e.g., U.S. Patent Publication No. 2011/0152357 A1, which is herein incorporated by reference in its entirety.

In embodiments, detection of the markers involves microRNA analysis.

Analytes (e.g., markers) can be detected by a variety of detection methods selected from, for example, a gas phase ion spectrometry method, an optical method, an electrochemical method, atomic force microscopy and a radio frequency method. In one embodiment, mass spectrometry, e.g., SELDI, is used. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltammetry and amperometry methods. Radio frequency methods include multipolar resonance spectroscopy.

In certain embodiments, the present invention features a single assay capable of measuring all of the protein coding genes of interest and miR-21 on the same platform. Examples include multiplex qPCR assays, microarray based technologies and the use of any DNA hybridization techniques that can simultaneously measure multiple genes at the same time.

Other variations of the assays described herein to provide for different assay formats for detection of the markers will be readily apparent to the one of ordinary skill in the art upon reading the present disclosure.

Reports

The methods of this invention, when practiced for commercial diagnostic purposes generally produce a report or summary of the normalized expression levels of one or more of the selected genes. The methods of this invention will produce a report comprising a prediction of the clinical outcome of a subject diagnosed with lung cancer. The methods and reports of this invention can further include storing the report in a database. Alternatively, the method can further create a record in a database for the subject and populate the record with data. In one embodiment the report is a paper report, in another embodiment the report is an auditory report, in another embodiment the report is an electronic record. It is contemplated that the report is provided to a physician and/or the patient. The receiving of the report can further include establishing a network connection to a server computer that includes the data and report and requesting the data and report from the server computer.

The methods provided by the present invention may also be automated in whole or in part.

Diagnostic Kits

The invention provides kits for diagnosing or for selecting a treatment for early stage lung cancer patients.

In embodiments, the kits include one or more reagents capable of detecting and/or capturing BRCA1, HIF1A, DLC1, XPO1, and/or miR-21. In related embodiments, the reagent is an antibody, a mass spectrometry probe, or a microarray.

In embodiments, the kits include an adsorbent that retains BRCA1, HIF1A, DLC1, XPO1, and/or miR-21. In related embodiments, the kits further contain directions for contacting a test sample with the adsorbent and detecting BRCA1, HIF1A, DLC1, XPO1, and/or miR-21 retained by the adsorbent.

In embodiments, the reagents and/or adsorbents are provided on a solid support (e.g., chip, microtiter plate, bead, resin, and the like).

In embodiments, the kits include washing solution(s) or instructions for making a washing solution, in which the combination of the reagent/adsorbent and the washing solution allows capture of the biomarkers on the reagent/adsorbent.

In embodiments, the kits include BRCA1, HIF1A, DLC1, XPO1, and/or miR-21, which can be used as standard(s) for calibration as may be desired.

In embodiments, the kit contains a container(s) that houses the components of the kit (e.g., reagent, adsorbent, solid support, and the like). Such containers can be boxes, ampoules, bottles, vials, tubes, bags, pouches, blister-packs, or other suitable container forms known in the art. Such containers can be made of plastic, glass, laminated paper, metal foil, and the like.

In embodiments, the kits further contain directions for using the kit in any of the methods described herein (e.g., diagnosing, monitoring, characterizing, and selecting a treatment for early stage lung cancer, and the like). In embodiments, the instructions include at least one of the following: description of the reagents, supports, and/or adsorbents; warnings; indications; counter-indications; animal study data; clinical study data; and/or references. The instructions may be printed directly on the container (when present), or as a label applied to the container, or as a separate sheet, pamphlet, card, or folder supplied in or with the container.

Types of Biological Samples

The level of BRCA1, HIF1A, DLC1, XPO1, and/or miR-21 is measured in different types of samples. In embodiments, the level of the markers is measured in a biologic sample. Suitable biologic samples include, without limit, a tissue sample (e.g., from a biopsy) and biological fluids (e.g., blood, blood serum, plasma, cerebrospinal fluid, saliva, urine, or any other biological fluid useful in the methods of the invention). In embodiments, the sample is a lung tissue sample derived from the patient.

EXAMPLES

It should be appreciated that the invention should not be construed to be limited to the examples that are now described; rather, the invention should be construed to include any and all applications provided herein and all equivalent variations within the skill of the ordinary artisan.

Protein coding and non-coding gene expression have been used to develop prognostic classifiers for patients with various types of cancer including stage I lung cancer. In many examples, the associations reported in single cohorts have failed to provide clinically useful information in additional patient populations (Subramanian J, Simon R. Gene expression-based prognostic signatures in lung cancer: ready for clinical use? J Natl Cancer Inst. 2010; 102:464-74). The present invention is based, at least in part, on the development of a clinically useful, prognostic classifier in early stage lung cancer to improve decisions about therapy and post-operative surveillance. Analysis focused on 42 genes with a known mechanistic role in lung cancer and/or an association with cancer prognosis to maximize the potential of developing biologically relevant classifier. 291 primary tumors from three geographically and ethnically diverse populations were analyzed by quantitative RT-PCR to identify genes with robust associations with prognosis. Sample sizes were of sufficient power to achieve this task. A Cox-regression based classifier was then produced using linear gene expression values of the four protein coding genes and all data, methodologies and scripts are publically available to allow readers to reproduce the results. Stratified analyses of TNM stage IA and stage IB were performed to identify high risk patients who would benefit from adjuvant chemotherapy. The robustness of the prognostic classifier was tested by evaluating three large, publically available lung adenocarcinoma microarray datasets. All statistical models were evaluated with both univariate and multivariate models adjusting for clinically relevant risk factors such as age, smoking and stage. Finally, this coding gene classifier was combined with the expression of miR-21, a microRNA that has been shown to be associated with relapse free survival and cancer-specific mortality in early stage lung cancer (Saito M, Schetter A J, Mollerup S, Kohno T, Skaug V, Bowman E D, et al. The Association of MicroRNA Expression with Prognosis and Progression in Early-Stage, Non-Small Cell Lung Adenocarcinoma: A Retrospective Analysis of Three Cohorts. Clin Cancer Res. 2011; 17:1875-82), to determine if this combination improved associations with prognosis in stage I, lung adenocarcinoma.

Example 1: XPO1, BRCA1, HIF1A, CA9, DLC1, and CCT3 Expression are Associated with Relapse-Free Survival of Stage I-II Lung Cancer in the Japan Cohort The strategy used for developing the coding gene classifier is shown in FIG. 1. 42 genes were selected based on literature support for a role in lung cancer (see Table 2, below).

TABLE 2

Univariate Cox regression analysis in the Japan cohort using microarray data
(AJCC TNF 6th, Stage I, n = 148)

| Gene Symbol | Affymetrix Probe ID* | HR (95% CI) | | P | References |
|---|---|---|---|---|---|
| DNMT1 | 201697_s_at | High vs. Low | 5.14 (2.11-12.5) | <0.001 | 1 |
| XPO1 | 208775_at | High vs. Low | 4.14 (1.79-9.59) | 0.001 | 2 |
| BRCA1 | 204531_s_at | High vs. Low | 4.12 (1.78-9.53) | 0.001 | 3 |
| HIF1A | 200969_at | High vs. Low | 3.03 (1.40-6.57) | 0.005 | 4, 5, 6 |
| CA9 | 205199_at | High vs. Low | 2.95 (1.37-6.39) | 0.006 | 7, 8 |
| DLC1 | 210762_s_at | High vs. Low | 0.34 (0.16-0.74) | 0.007 | 2 |
| CCT3 | 200910_at | High vs. Low | 2.91 (1.35-6.30) | 0.007 | 5 |
| SCLY | 221575_at | High vs. Low | 2.49 (1.18-5.29) | 0.017 | 2 |
| MMD | 203414_at | High vs. Low | 2.21 (1.06-4.58) | 0.034 | 9 |
| STK24 | 208855_s_at | High vs. Low | 2.16 (1.04-4.49) | 0.038 | 2 |
| IFI44 | 214453_s_at | High vs. Low | 2.15 (1.03-4.46) | 0.040 | 10 |
| RND3 | 212724_at | High vs. Low | 1.87 (0.91-3.82) | 0.088 | 11 |
| CCDC99 | 221685_s_at | High vs. Low | 1.83 (0.89-3.75) | 0.098 | 2 |
| PDPK1 | 224986_s_at | High vs. Low | 0.56 (0.27-1.14) | 0.107 | 2 |
| MAFK | 226206_at | High vs. Low | 0.56 (0.27-1.14) | 0.108 | 5 |
| ZAK | 225665_at | High vs. Low | 0.56 (0.27-1.15) | 0.115 | 2 |
| STAT1 | 200887_s_at | High vs. Low | 1.75 (0.86-3.59) | 0.125 | 9 |
| ERBB3 | 226213_at | High vs. Low | 1.67 (0.82-3.43) | 0.159 | 9, 11 |
| PKLR | 220078_at | High vs. Low | 0.61 (0.30-1.25) | 0.180 | 2 |
| LMF1 | 219136_s_at | High vs. Low | 0.63 (0.31-1.28) | 0.202 | 2 |
| GSTA1 | 203924_at | High vs. Low | 1.57 (0.78-3.18) | 0.209 | 10 |
| STX1A | 204729_s_at | High vs. Low | 1.56 (0.77-3.15) | 0.219 | 4, 5 |
| REG1A | 209752_at | High vs. Low | 1.48 (0.73-3.00) | 0.275 | 12 |
| CXCR7 | 212977_at | High vs. Low | 1.47 (0.73-2.99) | 0.282 | 13 |
| WNT3 | 299103_at | High vs. Low | 1.41 (0.70-2.86) | 0.336 | 11 |
| FAM164A | 205308_at | High vs. Low | 0.73 (0.36-1.47) | 0.381 | 2 |
| CCL19 | 210072_at | High vs. Low | 0.75 (0.37-1.50) | 0.413 | 10 |
| MDM2 | 229711_s_at | High vs. Low | 0.75 (0.37-1.51) | 0.418 | 14 |
| HLA-DPB1 | 201137_s_at | High vs. Low | 0.75 (0.37-1.51) | 0.420 | 5 |
| RNF5 | 209111_at | High vs. Low | 0.75 (0.37-1.52) | 0.428 | 5 |
| LCK | 204891_s_at | High vs. Low | 0.77 (0.38-1.55) | 0.461 | 9, 11 |
| TERT | 207199_at | High vs. Low | 0.81 (0.40-1.63) | 0.557 | 15 |
| CALB1 | 205626_s_at | High vs. Low | 1.22 (0.61-2.45) | 0.568 | 10 |
| SMPD1 | 209420_s_at | High vs. Low | 1.17 (0.58-2.34) | 0.663 | 2 |
| RB1 | 203132_at | High vs. Low | 0.86 (0.43-1.72) | 0.670 | 16 |
| MMP7 | 204259_at | High vs. Low | 1.15 (0.57-2.31) | 0.692 | 10 |
| ATP6V0D1 | 212041_at | High vs. Low | 1.15 (0.57-2.30) | 0.701 | 2 |
| CCR7 | 206337_at | High vs. Low | 0.87 (0.44-1.75) | 0.703 | 4 |
| CDKN2A | 209644_x_at | High vs. Low | 0.89 (0.44-1.78) | 0.732 | 16 |
| SLC1A7 | 243623_at | High vs. Low | 0.90 (0.45-1.80) | 0.766 | 10 |
| CCND1 | 208712_at | High vs. Low | 0.96 (0.48-1.91) | 0.900 | 16 |
| DUSP6 | 208891_at | High vs. Low | 0.97 (0.49-1.94) | 0.934 | 9 |

*If more than one probe was present for a particular gene, the probe with highest intensity was selected.
Cases were dichotomized based on the median expression value for each probe.

Figure 2:
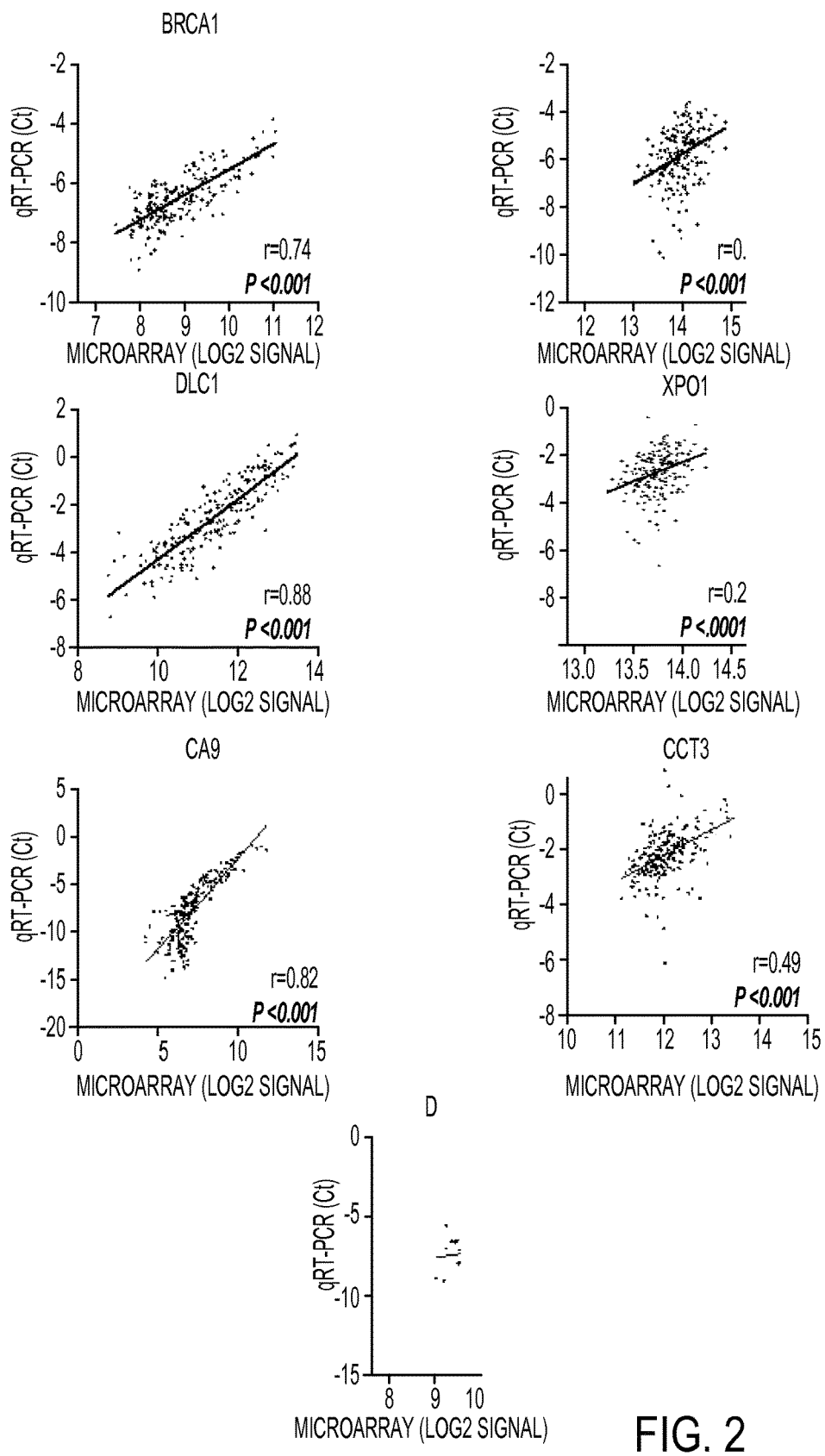
FIG. 2 includes graphs showing the validation of the microarray experiments. The graphs show the correlation between the microarray expression values and qRT-PCR expression values for each gene across all tumors that were examined.

Microarray data was analyzed on TNM stage I (AJCC 6th edition) lung cancer patients from the Japan cohort (n=148) and examined associations of those genes with relapse free-survival. Seven genes (DNMT1, XPO1, BRCA1, HIF1A, CA9, DLC1, and CCT3) were significantly associated with relapse-free survival (P<0.01) and selected for further analysis (see Table 2). qRT-PCR measurements significantly correlated with the microarray data (P<0.001) for six of the seven genes (FIG. 2). DNMT1 expression by qRT-PCR did not correlate with microarray data and was omitted from further analysis.

qRT-PCR expression for each gene was dichotomized as based on median expression for the Japan cohort (n=199). BRCA1 (hazard ratio [HR]=2.05, 95% confidence interval [CI], 1.17 to 3.58, P=0.012), HIF1A (HR=1.79, 95% CI, 1.03 to 3.11, P=0.038), CA9 (HR=3.25, 95% CI, 1.79 to 5.90, P=0.001), CCT3 (HR=2.14, 95% CI, 1.22 to 3.74, P=0.008), DLC1 (HR=0.44, 95% CI, 0.25 to 0.77, P=0.004), and XPO1 (HR=2.02, 95% CI, 1.15 to 3.53, P=0.014) were each significantly associated with relapse-free survival (RFS) (Table 3, below) further validating the microarray results.

TABLE 3

Univariate Cox Regression analysis of the expression of 6 genes

| | Japan cohort (stage I-II, n = 199) Relapse-Free Survival | | US/Norway cohort (stage I-II, n = 92) Cancer Specific Survival | |
|---|---|---|---|---|
| Gene* | HR (95% CI) | P | HR (95% CI) | P |
| BRCA1 (High vs Low) | 2.05 (1.17-3.58) | 0.012 | 3.21 (1.70-6.07) | <0.001 |
| HIF1A (High vs Low) | 1.79 (1.03-3.11) | 0.038 | 1.95 (1.07-3.57) | 0.029 |
| DLC1 (High vs Low) | 0.44 (0.25-0.77) | 0.004 | 0.45 (0.25-0.85) | 0.013 |
| XPO1 (High vs Low) | 2.02 (1.15-3.53) | 0.014 | 2.06 (0.12-3.76) | 0.019 |

TABLE 3-continued

Univariate Cox Regression analysis of the expression of 6 genes

| | Japan cohort (stage I-II, n = 199) Relapse-Free Survival | | US/Norway cohort (stage I-II, n = 92) Cancer Specific Survival | |
|---|---|---|---|---|
| Gene* | HR (95% CI) | P | HR (95% CI) | P |
| CCT3[†] (High vs Low) | 2.14 (1.22-3.74) | 0.008 | 1.72 (0.94-3.13) | 0.047 |
| CA9[†] (High vs Low) | 3.25 (1.79-5.90) | 0.001 | 1.03 (0.57-1.87) | 0.916 |

All cases were TNM stage I or II based on AJCC 6th staging.
Abbreviations:
AJCC, American Joint Committee on Cancer;
HR, hazard ratio;
CI, confidence interval.
*Cases were dichotomized based on the median expression value for each gene.
[†]One case was omitted in CA9 (Japan cohort, n = 198) and CCT3 (US/Norwey cohort, n = 91)

Example 2: BRCA1, HIF1A, DLC1, and XPO1 are Associated with Cancer-Specific Mortality in the Combined US/Norway Cohort All six genes were measured by qRT-PCR in the combined US/Norway cohort (stage I-II, n=92). The expression of BRCA1 (HR=3.21, 95% CI, 1.70 to 6.07, P<0.001), HIF1A (HR=2.01, 95% CI, 1.07 to 3.57, P=0.029), DLC1 (HR=0.45, 95% CI, 0.25 to 0.85, P=0.013), and XPO1 (HR=2.06, 95% CI, 1.12 to 3.76, P=0.019) were each significantly associated with cancer-specific mortality in the combined US/Norway cohort by Cox regression (Table 3, above).

Example 3: A Four Coding Gene Classifier is Associated with Prognosis in Five Independent Cohorts It was demonstrated that BRCA1, HIF1A, DLC1, and XPO1 are associated with prognosis in multiple cohorts from different regions of the world providing strong evidence that these can be useful prognostic biomarkers. In an attempt to make a robust prognostic classifier for lung cancer, a Cox regression model was developed using the expression of these four coding genes. Guidelines for prognostic factor studies in NSCLC recommends including the results in stage II patients with low risk of recurrence as well as stage I patients (Subramanian J, Simon R. Gene expression-based prognostic signatures in lung cancer: ready for clinical use? J Natl Cancer Inst. 2010; 102:464-74). Therefore, a gene classifier was built on all of the stage I and II patients in the Japan cohort (n=199) using multivariate Cox regression on linear expression values of each of the four genes. The resulting model was "classifier score=(0.104× BRCA1)+(0.133×HIF1A)+(−0.246×DLC1)+(0.378×XPO1)". This model was applied to the Japan and US/Norway cohorts using qRT-PCR expression data and to three publically available datasets (Director's cohort, n=378; Bhattacharjee cohort, n=100; Tomida cohort, n=92) using microarray expression data. Characteristics of these cohorts are found in Table 4, shown below

TABLE 4

Characteristics of study populations of patients from public database

| | Directors cohort (n = 371) | Tomida cohort (n = 92) | Bhattacharjee cohort (n = 100) |
|---|---|---|---|
| Age-years | | | |
| Mean (SD) | 64.4 (10.2) | 61.3 (10.0) | 64.1 (10.2) |
| Range | 33-87 | 35-84 | 33-88 |
| Gender (%) | | | |
| Male | 183 (49.3) | 50 (54.3) | 41 (41.0) |
| Female | 188 (50.7) | 42 (45.7) | 59 (59.0) |
| Histology (%) | | | |
| Adenocarcinoma | 371 (100.0) | 92 (100.0) | 100 (100.0) |
| AJCC TNM 6th Stage (%) | | | |
| IA | 114 (30.7) | 42 (45.7) | 35 (35.0) |
| IB | 162 (43.7) | 37 (40.2) | 40 (40.0) |
| IA or IB | 0 (0.0) | 0 (0.0) | 1 (1.0) |
| II | 95 (25.6) | 13 (14.1) | 24 (24.0) |
| Smoking history (%) | | | |
| Never | Data not available | 45 (53.2) | 10 (10.0) |
| <20 pack years | | 9 (5.4) | 11 (11.0) |
| ≥20 pack years | | 38 (8.7) | 78 (78.0) |
| Unknown | | 0 (0.0) | 1 (1.0) |
| Adjuvant therapy (%) | | | |
| None | 192 (51.8) | 92 (100.0) | Data not available |
| Chemotherapy | 40 (10.8) | 0 (0.0) | |
| Radiotherapy | 14 (3.8) | 0 (0.0) | |
| Chemo-radiotherapy | 26 (7.0) | 0 (0.0) | |
| Unknown | 99 (26.7) | 0 (0.0) | |

Abbreviations:
SD, standard deviation;
AJCC, American Joint Committee on Cancer.

Figure 3:
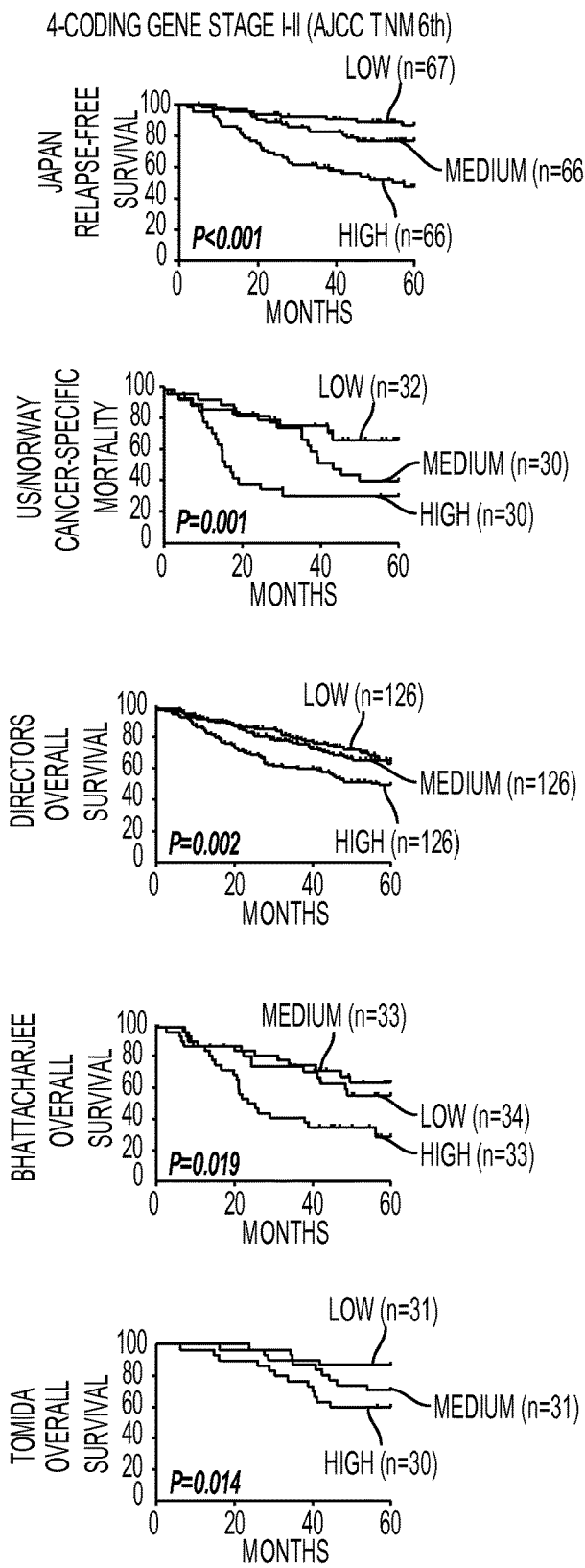
FIG. 3 includes Kaplan-Meier survival curves according to tertiles of the four coding gene signature in AJCC 6th edition stage I-II lung cancer from independent cohorts. Japan cohort (n=199) uses relapse-free survival as an endpoint. US/Norwegian cohort (n=95) uses cancer specific mortality as an endpoint. The Directors cohort (n=378), Bhattacharjee cohort (n=100), and Tomida cohorts (n=92), using overall survival as an endpoint.

The resulting classifier score was categorized as low, medium or high based on tertiles. The four coding gene classifier was significantly associated with prognosis in stage I-II patients in all five cohorts: Japan (P<0.001), US/Norway (P=0.001), Director's (P=0.002), Bhattacharjee (P=0.019) and Tomida (P=0.014) cohorts (FIG. 3). These results provide strong evidence that the four coding gene classifier is robust and will lead to reproducible predictions in ethnically and geographically-diverse populations.

Figure 4:
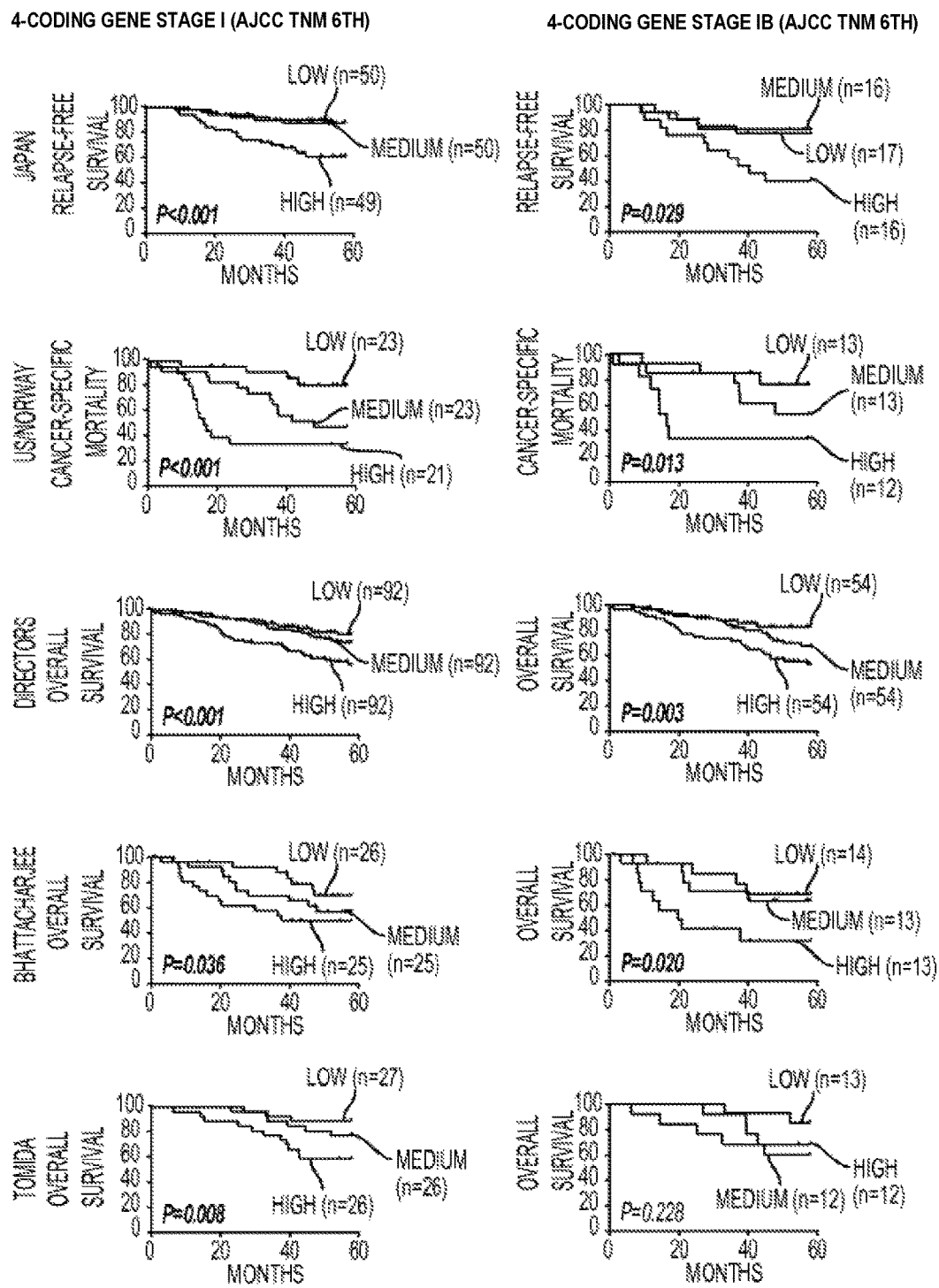
FIG. 4 includes Kaplan-Meier survival curves according to tertiles of four coding gene classifier in stage I lung cancer from independent cohorts. The four coding gene classifier was significantly associated with prognosis in stage I lung adenocarcinoma for all five cohorts including the Japan (P<0.001, n=149), US/Norway (P<0.001, n=67), Director's (P<0.001, n=276), Bhattacharjee (P=0.036, n=76) and Tomida (P=0.008, n=79) cohorts.

Example 4: A Four-Gene Classifier is Associated with Prognosis in Stage I Lung Cancer in Five Independent Cohorts In order to develop a prognostic gene classifier for early stage lung cancer, the study focused on stage I patients. The four coding gene classifier was significantly associated with prognosis in stage I lung adenocarcinoma for all five cohorts including the Japan (P<0.001, n=149), US/Norway (P<0.001, n=67), Director's (P<0.001, n=276), Bhattacharjee (P=0.036, n=76) and Tomida (P=0.008, n=79) cohorts (FIG. 4). In univariate Cox regression models, high risk group was associated with prognosis in the Japan (HR=3.84, 95% CI, 1.53 to 9.64, P=0.004), US/Norway (HR=8.03, 95% CI, 2.54 to 25.28, P<0.0005) cohorts, Director's (HR=2.68, 95% CI, 1.50 to 4.79, P=0.001), Bhattacharjee (HR=2.61, 95% CI, 1.04 to 6.56, P=0.042) and Tomida (HR=4.73, 95% CI, 1.32 to 16.96, P=0.017) cohorts. Multivariate Cox regression demonstrated that these associations were independent of other clinical characteristics (Table 5, below). These data suggest that the four coding gene classifier has potential to be used with other clinical characteristics to help identify stage I patients at high risk of cancer relapse.

The patients in this study were staged based on AJCC 6th edition at the time of diagnosis. The four gene classifier was developed and validated based on AJCC 6th edition staging

TABLE 5

Univariate and Multivariate Cox regression of the four gene classifier in five independent cohorts (AJCC TNF 6th edition, Stage I patients)

| Variable | | Univariate Analysis | | Multivariate Analysis‡ | |
|---|---|---|---|---|---|
| | | HR (95% CI) | P | HR (95% CI) | P |
| Japan cohort (n = 149) | | | | | |
| 4 gene classifier (qRT-PCR)* | Low | Reference | NA | Reference | NA |
| | Medium | 1.04 (0.34-3.23) | 0.940 | 1.30 (0.41-4.11) | 0.657 |
| | High | 3.84 (1.53-9.64) | 0.004 | 3.78 (1.51-9.51) | 0.005 |
| | | Trend P = 0.002 | | Trend P = 0.003 | |
| AJCC 6th Stage | IB/IA | 2.89 (1.43-5.87) | 0.003 | 2.57 (1.22-5.41) | 0.013 |
| Age | Continous | 1.00 (0.96-1.05) | 0.895 | 1.00 (0.95-1.05) | 0.991 |
| Gender | Male/Female | 0.95 (0.47-1.94) | 0.893 | 0.80 (0.93-1.65) | 0.551 |
| Pack years | ≥20/<20 | 1.51 (0.72-3.16) | 0.271 | | |
| US/Norway cohort (n = 67)† | | | | | |
| 4 gene classifier (qRT-PCR)* | Low | Reference | NA | | NA |
| | Medium | 3.46 (1.12-10.79) | 0.031 | 3.48 (1.11-10.90) | 0.032 |
| | High | 8.03 (2.54-25.28) | <0.0005 | 8.40 (2.65-26.67) | < 0.0005 |
| | | Trend P < 0.0005 | | Trend P < 0.0005 | |
| AJCC 6th Stage | IB/IA | 0.99 (0.46-2.12) | 0.971 | 0.78 (0.36-1.68) | 0.527 |
| Age | Continous | 1.01 (0.97-1.05) | 0.576 | 1.02 (0.97-1.06) | 0.485 |
| Gender | Male/Female | 0.88 (0.43-1.82) | 0.723 | 0.91 (0.44-1.91) | 0.807 |
| Pack years | ≥20/<20 | 0.97 (0.38-2.46) | 0.943 | | |
| Directors cohort (n = 276) | | | | | |
| 4 gene classifier (microarray)* | Low | Reference | NA | | NA |
| | Medium | 1.35 (0.71-2.55) | 0.362 | 1.37 (0.72-2.60) | 0.332 |
| | High | 2.66 (1.50-4.79) | 0.001 | 2.68 (1.49-4.80) | 0.001 |
| | | Trend P < 0.0005 | | Trend P < 0.0005 | |
| AJCC 6th Stage | IB/IA | 1.43 (0.90-2.27) | 0.134 | 1.42 (0.89-2.28) | 0.144 |
| Age | Continous | 1.03 (1.01-1.05) | 0.008 | 1.03 (1.01-1.06) | 0.006 |
| Gender | Male/Female | 1.20 (0.77-1.87) | 0.410 | 0.98 (0.63-1.55) | 0.960 |
| Pack years | ≥20/<20 | | | | |
| Bhattacharjee cohort (n = 76) | | | | | |
| 4 gene classifier (microarray)* | Low | Reference | NA | | NA |
| | Medium | 1.67 (0.65-4.31) | 0.290 | 1.35 (0.51-3.58) | 0.541 |
| | High | 2.61 (1.04-6.56) | 0.042 | 2.69 (1.05-6.94) | 0.040 |
| | | Trend P = 0.039 | | Trend P = 0.036 | |
| AJCC 6th Stage | IB/IA | 1.74 (0.84-3.61) | 0.138 | 2.43 (1.12-5.24) | 0.023 |
| Age | Continous | 1.01 (1.00-1.08) | 0.037 | 1.06 (1.01-1.10) | 0.009 |
| Gender | Male/Female | 1.29 (0.64-2.62) | 0.475 | 0.82 (0.38-1.78) | 0.624 |
| Pack years | ≥20/<20 | 1.77 (0.68-4.62) | 0.241 | | |
| Tomida cohort (n = 79) | | | | | |
| 4 gene classifier (microarray)* | Low | Reference | NA | | NA |
| | Medium | 2.14 (0.53-8.55) | 0.283 | 1.79 (1.44-7.32) | 0.418 |
| | High | 4.73 (1.32-16.96) | 0.017 | 3.92 (1.07-14.36) | 0.024 |
| | | Trend P = 0.011 | | Trend P = 0.024 | |
| AJCC 6th Stage | IB/IA | 1.45 (0.60-3.50) | 0.409 | 1.27 (0.47-3.46) | 0.639 |
| Age | Continous | 1.02 (0.97-1.06) | 0.449 | 1.01 (0.96-1.06) | 0.766 |
| Gender | Male/Female | 2.64 (1.02-6.89) | 0.046 | 2.43 (0.93-6.39) | 0.071 |
| Pack years | ≥20/<20 | 1.39 (0.58-3.36) | 0.462 | | |

Abbreviations:
AJCC, American Joint Committee on Cancer;
HR, hazard ratio;
CI, confidence interval;
NA, not applicable.
*The 4 coding gene classifer was categorized based on tertiles.
†All univariate and multivariate models were adjusted for cohort membership for the US/Norway analyses.
‡Multivariate models included all variables that were significant in univariate models in at least one cohort.

Subgroup analysis was performed on stage IB patients (FIG. 4). The four-gene classifier was significantly associated with prognosis stage IB patients in the Japan (P=0.029, n=49), US/Norway (P=0.013, n=38), Director's (P=0.003, n=162), and Bhattacharjee (P=0.020, n=40) cohorts further demonstrating the potential of this protein coding gene classifier as a prognostic biomarker for lung cancer.

information. In 2009, the AJCC 7th edition TNM staging was developed and published. To determine how the classifier performs with AJCC 7th edition staging, patients were restaged to AJCC 7th edition for cases with available data (Table 1, below) and found that the four gene classifier was significantly associated in AJCC 7th edition TNM stage I lung cancer patients in both the Japan (P<0.001, FIG. 5) and the US/Norway cohorts (P=0.003, FIG. 6).

TABLE 1

Charastistics of study populations of patients in the Japan, Norway, and US cohorts

|  | Japan cohort (n = 199) | Norway cohort (n = 25) | US cohort (n = 67) |
| --- | --- | --- | --- |
| Age-years |  |  |  |
| Mean (SD) | 59.4 (7.7) | 64.0 (11.8) | 64.9 (10.0) |
| Range | 30-76 | 37-82 | 40-90 |
| Gender (%) |  |  |  |
| Male | 97 (48.7) | 15 (60.0) | 37 (55.2) |
| Female | 102 (51.3) | 10 (40.0) | 30 (44.8) |
| Race (%) |  |  |  |
| Caucasian | 0 (0.0) | 25 (100.0) | 43 (64.2) |
| African-American | 0 (0.0) | 0 (0.0) | 24 (35.8) |
| Asian | 199 (100.0) | 0 (0.0) | 0 (0.0) |
| Histology (%) |  |  |  |
| Adenocarcinoma | 199 (100.0) | 25 (100.0) | 67 (100.0) |
| Tumor size-cm |  |  |  |
| Mean (SD) | 3.0 (1.6) | 3.8 (1.7) | 3.7 (2.1) |
| Range | 0.9-14.0 | 2.0-6.5 | 0.9-10.5 |
| Unknown | 0 | 13 | 2 |
| AJCC TNM 6th stage (%) |  |  |  |
| IA | 100 (50.3) | 6 (24.0) | 23 (34.3) |
| IB | 49 (24.6) | 14 (56.0) | 24 (35.6) |
| II | 50 (25.1) | 5 (20.0) | 20 (29.9) |
| AJCC TNM 7th stage (%)* |  |  |  |
| IA | 99 (49.7) | 6 (24.0) | 24 (36.4) |
| IB | 37 (18.6) | 5 (20.0) | 12 (18.2) |
| II | 63 (31.7) | 5 (20.0) | 30 (45.5) |
| IB or II | 0 (0.0) | 7 (28.0) | 0 (0.0) |
| Unknown | 0 (0.0) | 2 (8.0) | 0 (0.0) |
| Smoking history (%) |  |  |  |
| Never | 98 (49.2) | 1 (4.0) | 4 (6.0) |
| <20 pack years | 32 (16.1) | 11 (44.0) | 8 (11.9) |
| ≥20 pack years | 69 (34.7) | 12 (46.0) | 54 (80.6) |
| Unknown | 0 (0.0) | 1 (4.0) | 1 (1.5) |
| Adjuvant therapy (%) |  |  |  |
| Adjuvant chemotherapy | 8 (4.0) |  | 0 (0.0) |
| None | 191 (96.0) |  | 59 (86.1) |
| Unknown | 0 (0.0) | 25 (100.0) | 8 (11.9)† |

Abbrevations:
SD, standard deviation;
AJCC, American Joint Committee on Cancer.
*Cases were restaged to AJCC 7th edition based on tumor size and/or pathology reports where possible.
†No information on the timing of therapies (possibly either after surgery or after recurrence).

Example 5: The Four Coding Gene Classifier and Noncoding miR-21 are Independently Associated with Prognosis in Stage I Lung Adenocarcinoma It was previously reported that high miR-21 expression in tumors was associated with poor prognosis in stage I, lung adenocarcinoma (Saito M. et al. The Association of MicroRNA Expression with Prognosis and Progression in Early-Stage, Non-Small Cell Lung Adenocarcinoma: A Retrospective Analysis of Three Cohorts. Clin Cancer Res. 2011; 17:1875-82). That study utilized the same Japan and US/Norway cohorts as the current study and provides an opportunity to determine if the combination of miR-21 and four coding gene classifier improves prognostic utility.

Figure 10:
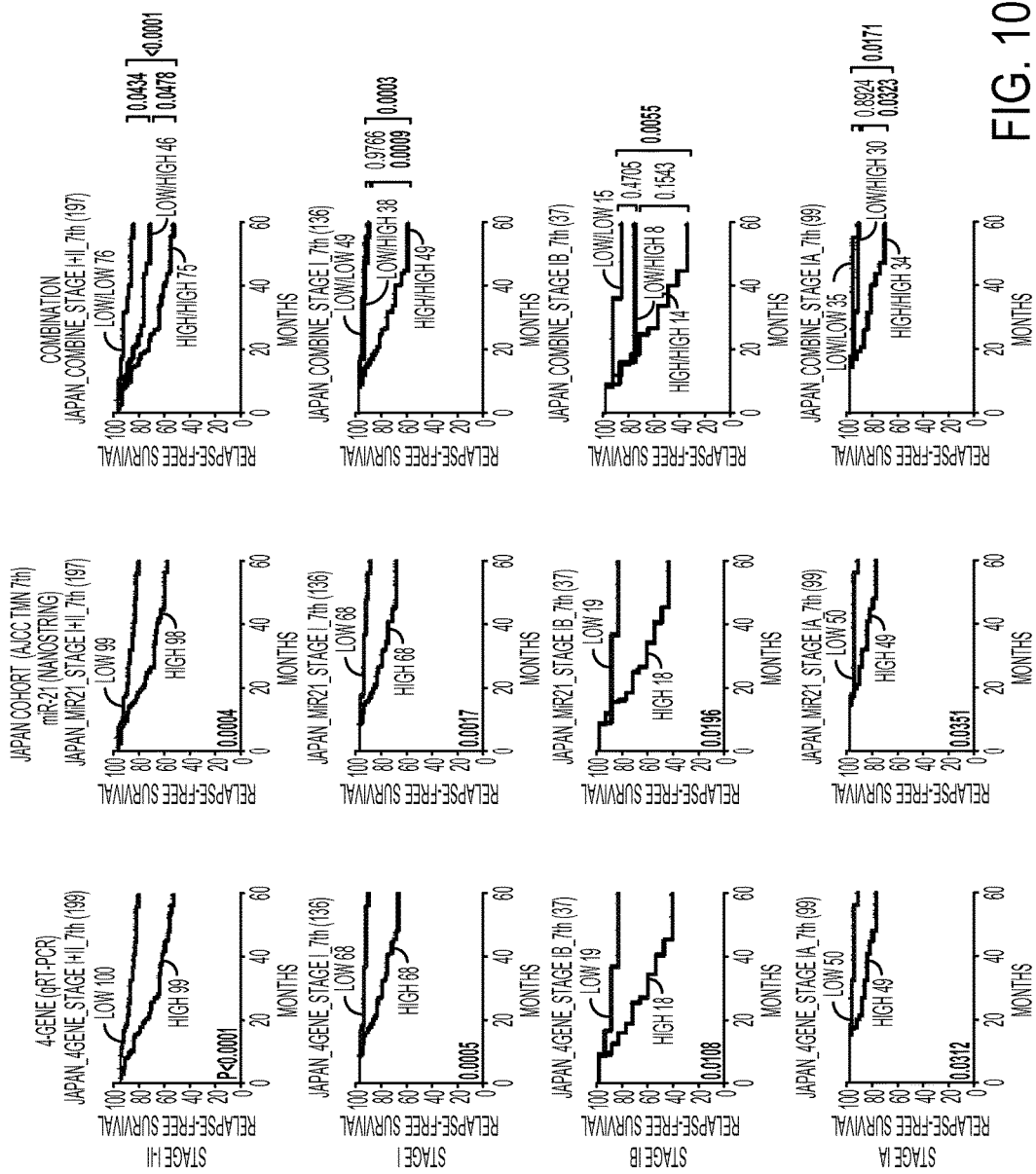
FIG. 10 includes Kaplan Meier analysis of the 4-gene classifier (using qRT-PCR) and miR-21 expression (using Nanostring human microRNA assays) in the Japanese cohort. These data show associations of the 4-gene classifier and miR-21 expression with progression free survival time, stratified by TNM stages. Each classifier is significantly associated with prognosis in each TNM stage subgroup and the combination of the two classifiers performs superior to each alone. Therefore, the 4 gene-classifier and miR-21 (alone or in combination) are prognostic biomarkers of early stage lung cancer. Additionally, using nanostring to measure miR-21 results in stronger associations with prognosis than qRT-PCR.

Previously, qRT-PCR was used to measure miR-21 in lung tumors. The patients in this study were staged based on AJCC 6th edition at the time of diagnosis. Therefore, the four gene classifier was developed and validated based on AJCC 6th edition staging information. In 2009, the AJCC 7th edition TNM staging was developed and published. To determine how this classifier performs with current AJCC 7th edition staging, patients were restaged to AJCC 7th edition for cases with available data (FIG. 10) and found that the four gene classifier was significantly associated in AJCC 7th edition TNM stage I lung cancer patients in both the Japanese (P=0.0005, FIG. 5) and the US/Norway cohorts (P=0.0026, FIG. 6).

Figure 7:
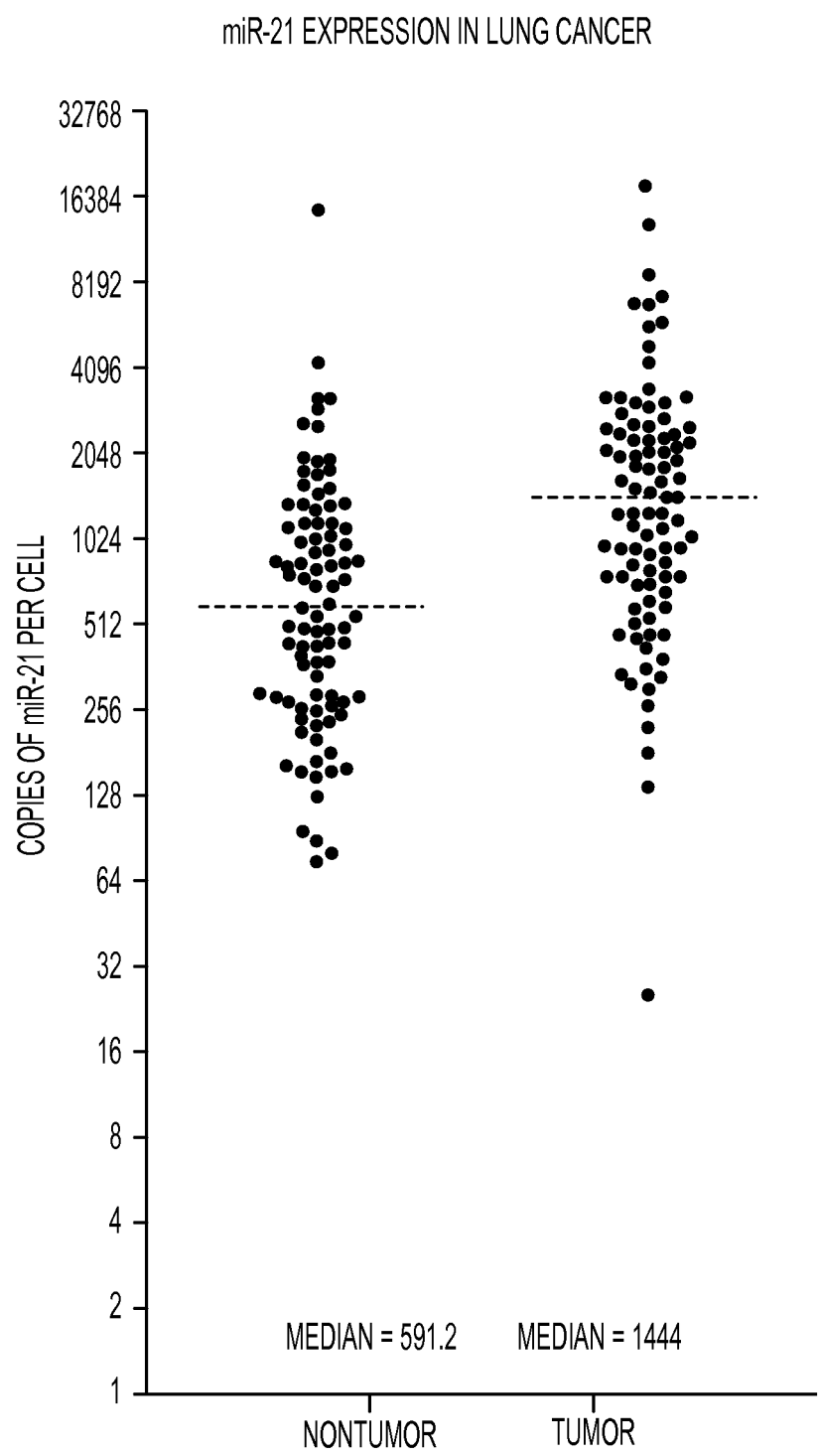
FIG. 7 is a graph showing the estimated copy number of miR-21 per cell in tumor and non tumor cells based on Nanostring Human microRNA assays.

This study estimated the copy number of miR-21 per cell in lung tumors and adjacent noncancerous tissues. For this, Nanostring Human microRNA assays were used to measure the global microRNA expression patterns of the US and Norway cohorts. Tumors had approximately 2.4 fold higher expression of miR-21 with an estimated median copy number of 1444 while noncancerous tissue had a median copy number of 591.2 (FIG. 7).

Figure 5:
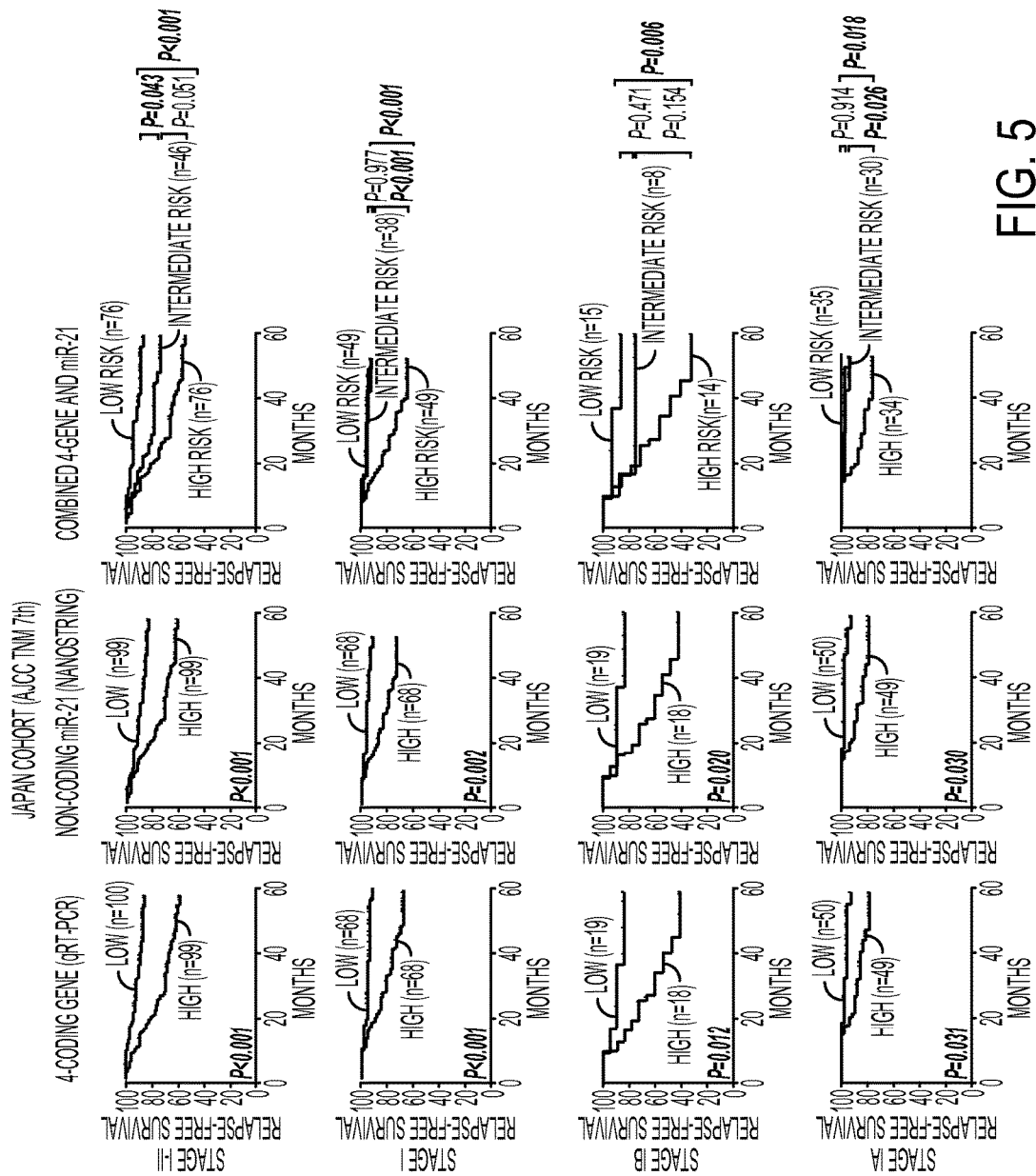
FIG. 5 includes graphs showing that in TNM stage I non-small cell lung cancer (NSCLC), the combined four coding gene classifier with miR-21 expression predicts relapse-free and cancer-specific mortality better than either alone. Included are Kaplan-Meier (KM) curves for four-gene classifier in the Japan cohort; KM curves for noncoding miR-21 in the Japan cohort; and KM curves for the combined four coding gene classifier and noncoding miR-21 in the Japan cohort. These analyses are stratified by AJCC 7th edition TNM staging. For this figure, miR-21 was measured by Nanostring human microRNA assays version 1.
Figure 6:
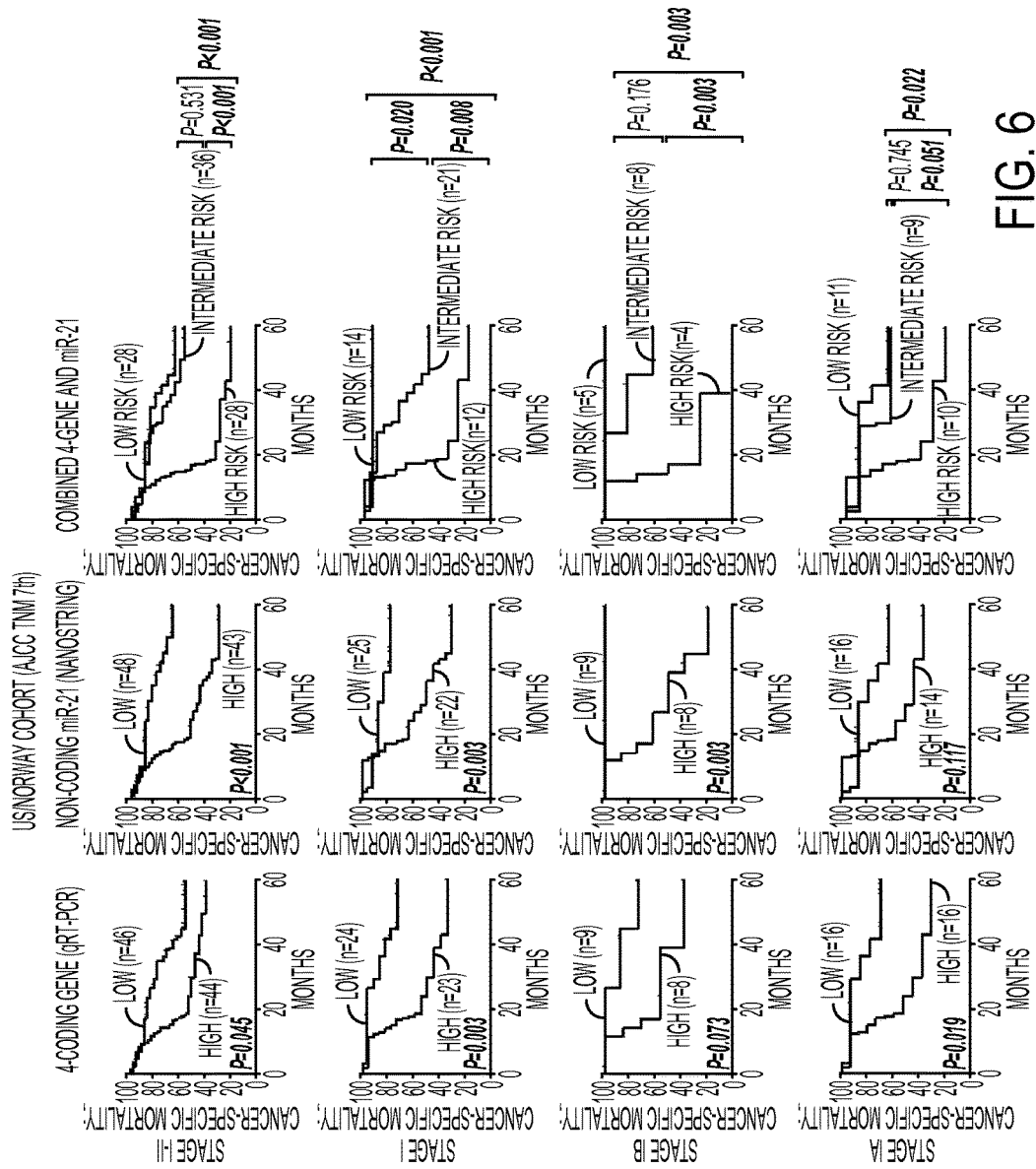
FIG. 6 includes graphs showing that in TNM stage I non-small cell lung cancer (NSCLC), the combined four coding gene classifier with miR-21 expression predicts relapse-free and cancer-specific mortality better than either alone. Included are Kaplan-Meier (KM) curves for four-gene classifier in the US/Norway cohort; KM curves for noncoding miR-21 in the US/Norway cohort; and KM curves for the combined four coding gene classifier and noncoding miR-21 in the US/Norway cohort. These analyses are stratified by AJCC 7th edition TNM staging. For this figure, miR-21 was measured by Nanostring human microRNA assays version 1.
Figure 8:
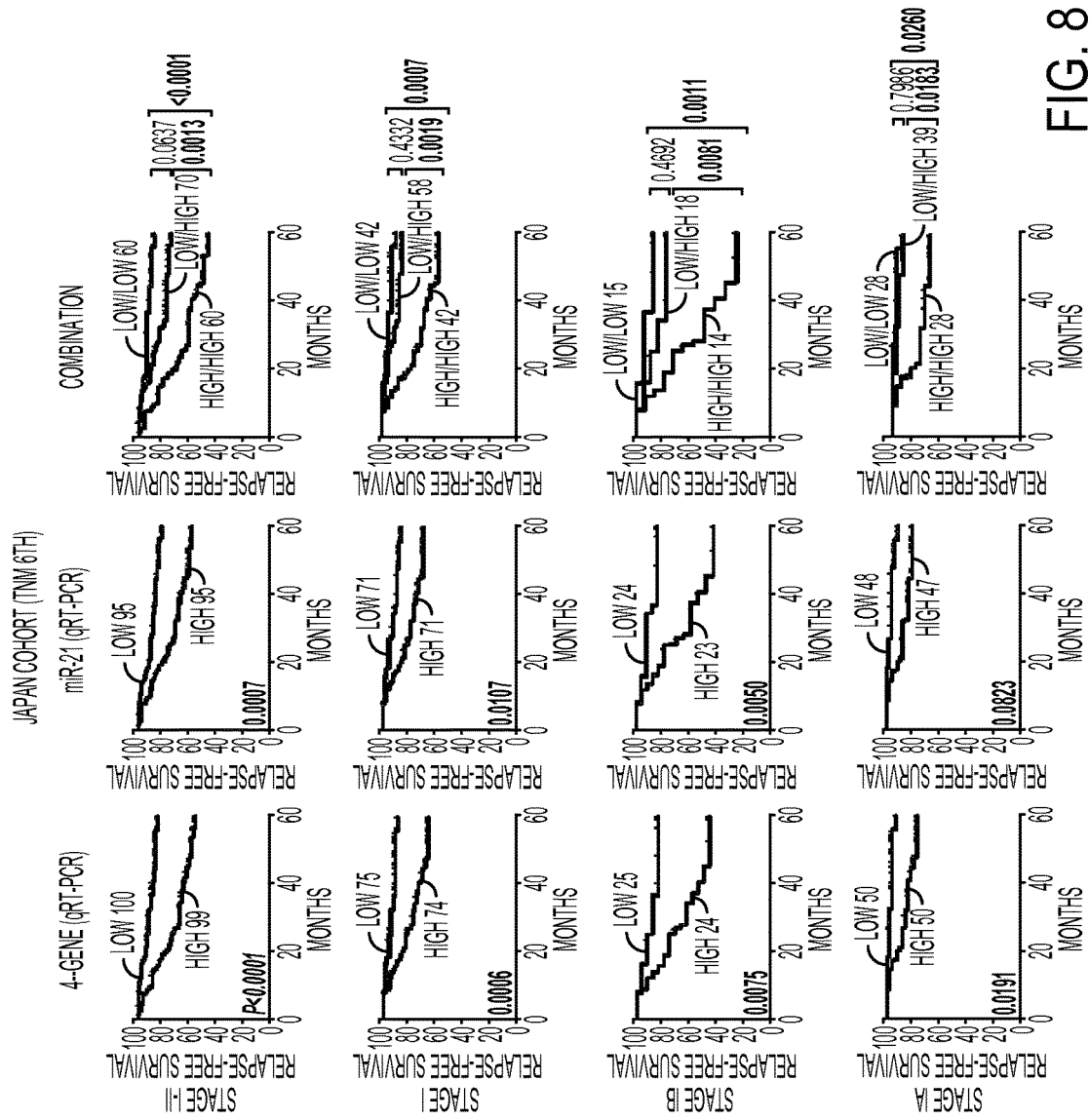
FIG. 8 includes Kaplan-Meier (KM) curves for the four coding gene classifier in the Japan cohort by TNM stage. The combined four coding gene classifier with noncoding miR-21 expression predicts relapse-free in the Japan cohort (using AJCC 6th edition staging) better than either alone.
Figure 9:
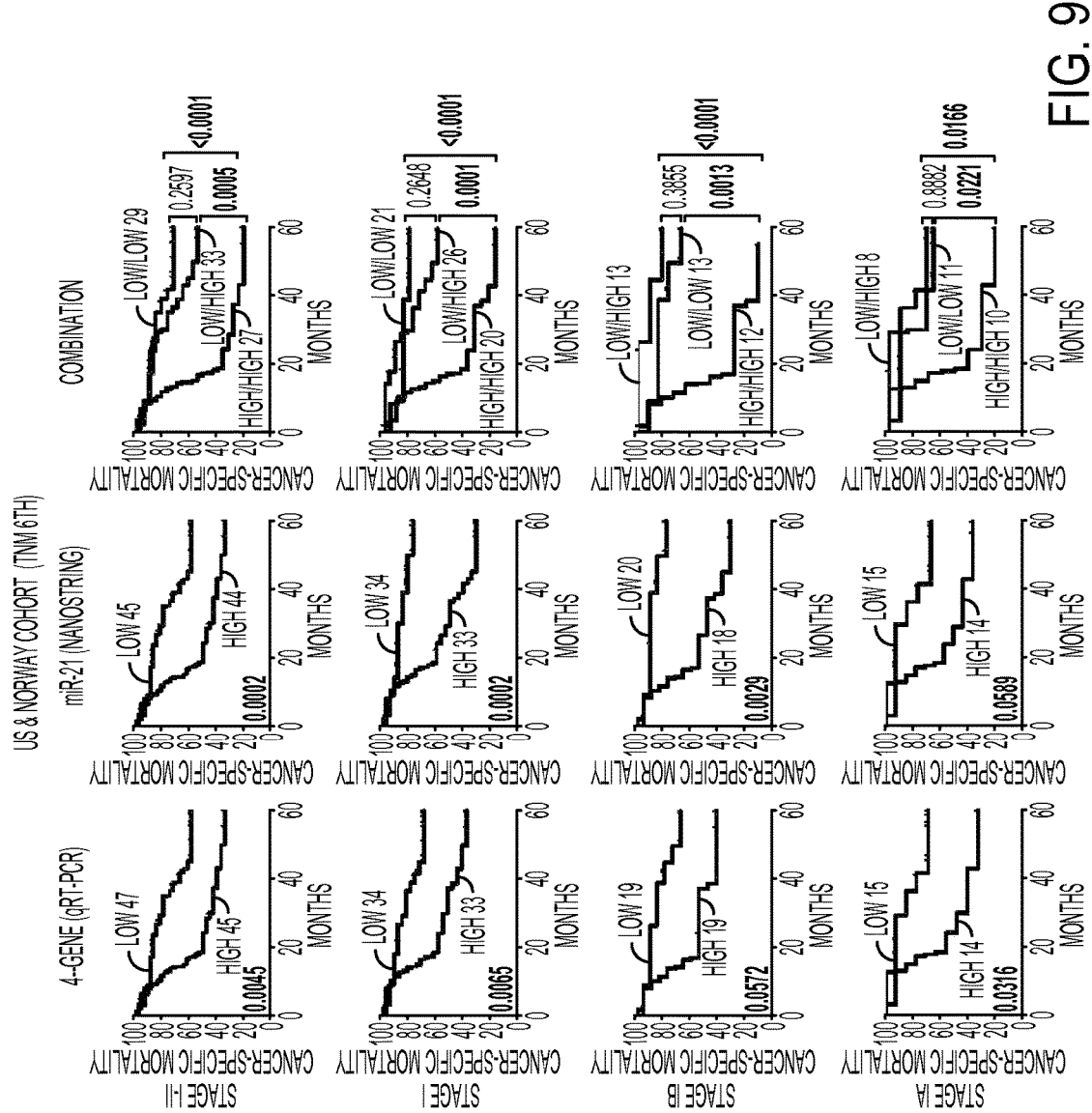
FIG. 9 includes Kaplan-Meier (KM) curves for the four coding gene classifier in the US/Norway cohort by TNM stage. The combined four coding gene classifier with noncoding miR-21 expression predicts cancer-specific mortality in the US/Norway cohort (using AJCC 6th edition staging) better than either alone.

To investigate the association of miR-21 with prognosis, patients were dichotomized as high or low based on median expression values based on either qRT-PCR data (Japan cohort) or Nanostring data (US and Norway cohorts). As previously reported, miR-21 is significantly associated with worse prognosis TNM stage I patients in both the Japan and US/Norway cohorts. Interestingly, associations of miR-21 with prognosis were stronger in the US/Norway cohorts when using Nanostring to measure miR-21 compared to previously reported qRT-PCR measurements of miR-21. These data were analyzed based on both AJCC 7th edition staging (FIGS. 5 and 6) and AJCC 6th edition staging (FIGS. 8 and 9). Nanostring was then used to measure microRNA expression in the Japan cohort and again, the associations between Nanostring data and qRT-PCR data showed that the Nanostring data gave stronger associations with prognosis (FIGS. 5 and 6 compared to FIGS. 10 and 11).

It was next determined if the combination of miR-21 and the four gene classifier was superior to either alone. For this purpose, patients were dichotomized based on median values of the four gene signature. Kaplan-Meier analysis (FIGS. 5 and 6) demonstrates that patients with a low four gene classifier score and low miR-21 (categorized as low risk) had the best prognosis. In general, patients categorized as high risk by only one of these markers had an intermediate prognosis and patients with high four-gene classifier/high miR-21 (categorized as high risk) had the worst prognosis, regardless of TNM stage groups. This was true for staging based on AJCC 7th edition (FIGS. 5 and 6) and AJCC 6th edition (FIGS. 8 and 9). Multivariate analysis showed that both high four-gene classifier (HR, 2.28; 95% CI, 1.15-4.51, P=0.018) and high miR-21 (HR, 2.06; 95% CI, 1.13-3.76, P=0.019) were independent of one another in the Japan cohort (Table 6, below). Multivariate analysis for US/Norway cohort indicated that high four-gene classifier (HR, 1.87; 95% CI, 0.96-3.63, P=0.065) and high miR-21 (HR, 3.26; 95% CI, 1.60-6.64, P=0.001) were each associated with prognosis (Table 6). Similar results were seen when restricting the analyses to TNM stage I patients. (Table 6) These results indicate that the four coding gene classifier and miR-21 expression can be used together as a prognostic biomarker for stage I lung adenocarcinoma. Similar results were observed in a combined analysis of TNM stage IB lung cancer (FIG. 9).

Figure 12:
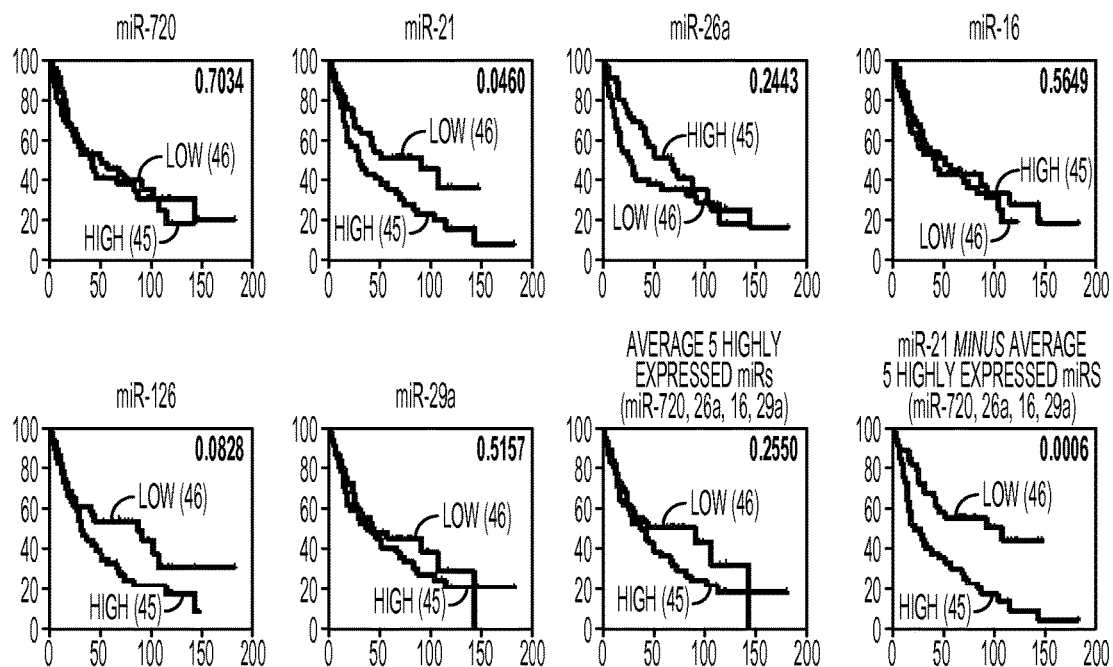
FIG. 12 shows the results of nCounter Human miRNA assays. miR-720, miR-26a, miR-16, miR-126 and miR-29 were the highest expressed microRNAs (excluding miR-21) and none of these microRNAs were associated with prognosis.
Figure 13:
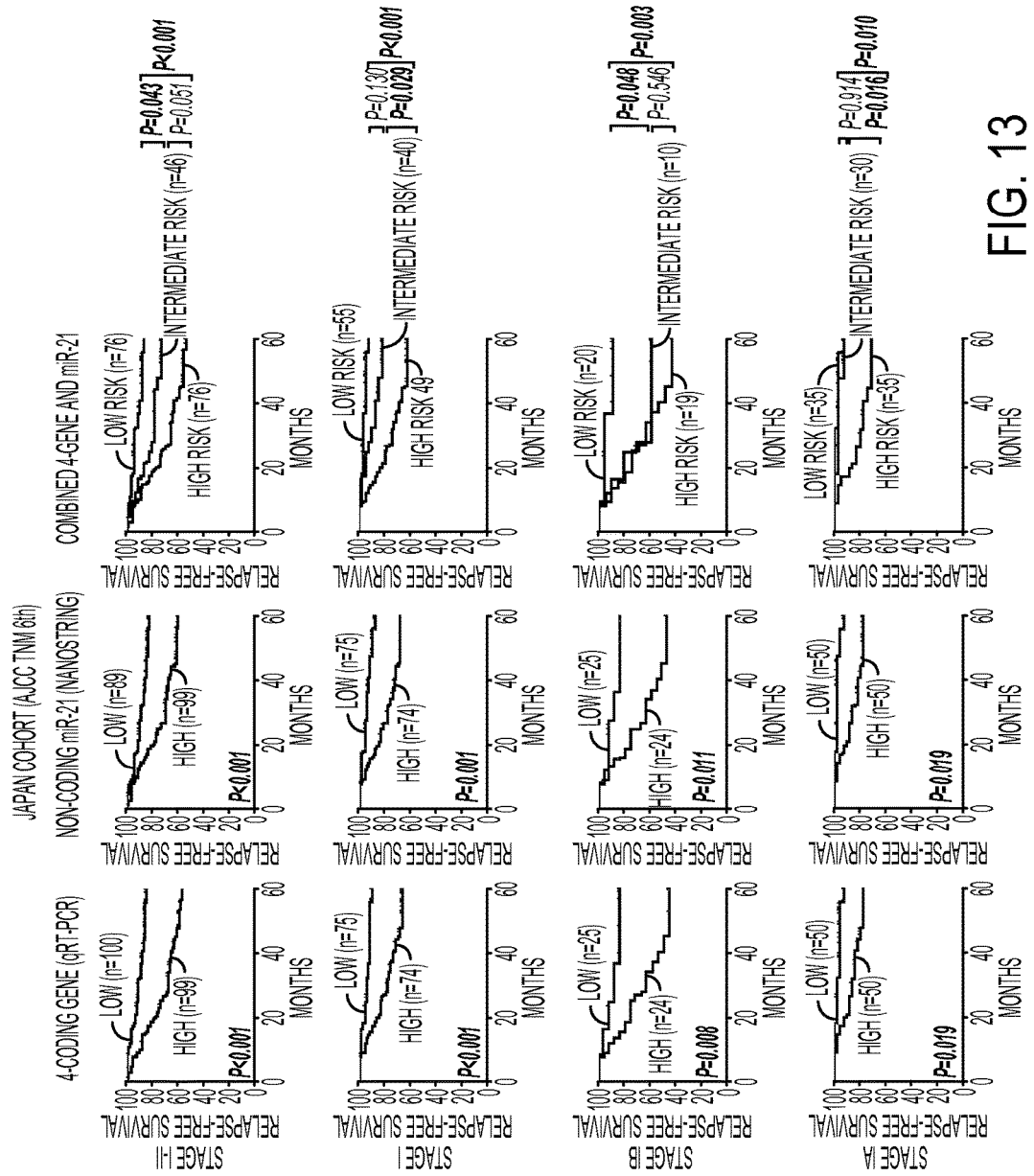
FIG. 13 includes Kaplan Meier analysis of the 4-gene classifier (using qRT-PCR) and miR-21 expression (using Nanostring human microRNA assays) in the Japanese cohort. These data show associations of the 4-gene classifier and miR-21 expression with progression free survival time, stratified by TNM stages. Each classifier is significantly associated with prognosis in each TNM stage subgroup and the combination of the two classifiers performs superior to each alone. Therefore, the 4 gene-classifier and miR-21 (alone or in combination) are prognostic biomarkers of early stage lung cancer. These analyses are stratified by AJCC 6th edition TNM staging. Additionally, using nanostring to measure miR-21 results in stronger associations with prognosis than qRT-PCR.
Figure 14:
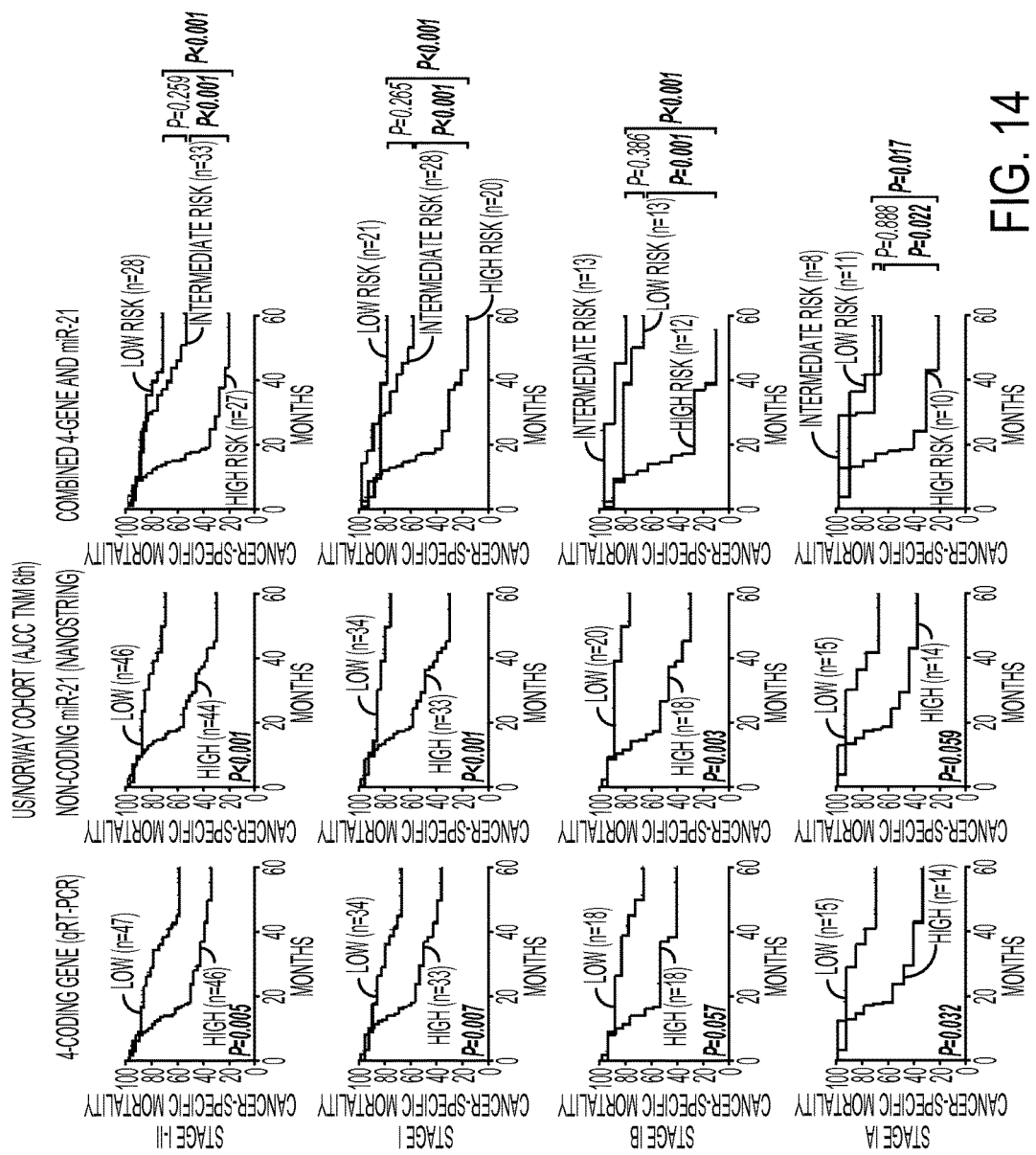
FIG. 14 includes Kaplan Meier analysis of the 4-gene classifier (using qRT-PCR) and miR-21 expression (using Nanostring human microRNA assays) in the US/Norway cohort. These data show associations of the 4-gene classifier and miR-21 expression with progression free survival time, stratified by TNM stages. Each classifier is significantly associated with prognosis in each TNM stage subgroup and the combination of the two classifiers performs superior to each alone. Therefore, the 4 gene-classifier and miR-21 (alone or in combination) are prognostic biomarkers of early stage lung cancer. These analyses are stratified by AJCC 6th edition TNM staging. Additionally, using nanostring to measure miR-21 results in stronger associations with prognosis than qRT-PCR.

It was next examined if another method of measuring miR-21 provided the same results in a way that may be easier to translate to the clinic. For this, nCounter Human miRNA assays were used, which provides a method for digital detection of hundreds of microRNAs with minimal sample preparation and no amplification. miR-720, miR-26a, miR-16, miR-126 and miR-29 were the highest expressed microRNAs (excluding miR-21) and none of these microRNAs were associated with prognosis (FIG. 12). Therefore, miR-21 expression was normalized to the geometric mean of these five microRNAs. Similar results were observed when comparing the nCounter Human miRNA assay measurement of miR-21 with previous reports using qRT-PCR. Using the nCounter assays, higher than median expression of miR-21 was significantly associated with worse prognosis in stage I patients in both the Japan and US/Norway cohorts. Interestingly, associations of miR-21 with prognosis were stronger when using nCounter assays to measure miR-21 compared to previously reported qRT-PCR measurements of miR-21. These data were analyzed based on both AJCC 7th edition staging (FIGS. 5, 6) and AJCC 6th edition staging (FIGS. 13 and 14).

Evaluation was carried out to determine if the combination of miR-21 and the four gene classifier was superior to either alone. Kaplan-Meier analysis (FIGS. 5 and 6) demonstrates that patients with a low four gene classifier score and low miR-21 (categorized as low risk) had the best prognosis. In general, patients categorized as high risk by only one of these markers had an intermediate prognosis and patients with high four-gene classifier/high miR-21 (categorized as high risk) had the worst prognosis, regardless of TNM stage groups. Multivariate analysis showed that both the four-gene classifier and miR-21 were statistically independent of one another in the Japan and the US/Norway cohort (Table 6). These results suggest that the four coding gene classifier and miR-21 expression can be used together as a prognostic biomarker for stage I lung adenocarcinoma.

TABLE 6

| Variable | | Univariate analysis | | Multivariate analysis | |
| --- | --- | --- | --- | --- | --- |
| | | HR (95% CI) | P | HR (95% CI) | P |
| Japan cohort (Stage I-II, n = 199) | | | | | |
| 4 gene classifier (qRT-PCR)* | High/Low | 3.56 (1.94-6.55) | 0.000 | 2.39 (1.16-4.90) | 0.018 |
| miR-21 (Nanostring)* | High/Low | 2.75 (1.53-4.94) | 0.001 | 1.34 (0.67-2.69) | 0.410 |
| AJCC 7th Stage | II/I | 3.19 (1.87-5.45) | 0.000 | 2.07 (1.15-3.71) | 0.015 |
| Age | Continous | 1.03 (0.99-1.07) | 0.132 | 1.03 (0.99-1.07) | 0.140 |
| Gender | Male/Female | 1.27 (0.74-2.16) | 0.382 | 1.21 (0.70-2.08) | 0.500 |
| Packyears | ≥20/<20 | 1.63 (0.94-2.79) | 0.064 | | |
| US/Norway cohort (Stage I-II, n = 39)† | | | | | |
| 4 gene classifier (qRT-PCR)* | High/Low | 1.95 (1.04-3.66) | 0.037 | 1.88 (0.96-3.65) | 0.064 |
| miR-21 (Nanostring)* | High/Low | 3.38 (1.72-6.65) | 0.000 | 3.42 (1.66-7.04) | 0.001 |
| AJCC 7th Stage | II/I | 1.60 (0.84-3.03) | 0.150 | 1.45 (0.76-2.75) | 0.262 |
| Age | Continous | 1.10 (0.98-1.04) | 0.556 | 1.01 (0.98-1.04) | 0.676 |
| Gender | Male/Female | 1.02 (0.55-1.90) | 0.938 | 0.79 (0.41-1.62) | 0.487 |
| Packyears | ≥20/<20 | 0.86 (0.42-1.78) | 0.665 | | |
| Japan cohort (Stage I, n = 136) | | | | | |
| 4 gene classifier (qRT-PCR)* | High/Low | 4.76 (1.79-12.64) | 0.002 | 4.14 (1.39-12.32) | 0.011 |
| miR-21 (Nanostring)* | High/Low | 3.89 (1.56-9.69) | 0.004 | 1.73 (0.60-4.98) | 0.312 |
| AJCC 7th Stage | IB/IA | 3.25 (1.50-7.01) | 0.003 | 3.36 (1.46-7.70) | 0.004 |
| Age | Continous | 1.00 (0.95-1.06) | 0.919 | 1.00 (0.95-1.05) | 0.967 |
| Gender | Male/Female | 0.98 (0.45-2.14) | 0.967 | 0.83 (0.38-1.84) | 0.654 |
| Packyears | ≥20/<20 | 1.54 (0.69-3.47) | 0.294 | | |
| US/Norway cohort (Stage I, n = 47)† | | | | | |
| 4 gene classifier (qRT-PCR)* | High/Low | 4.02 (1.53-10.59) | 0.005 | 4.68 (1.67-13.15) | 0.003 |
| miR-21 (Nanostring)* | High/Low | 4.11 (1.49-11.37) | 0.006 | 6.55 (1.97-21.78) | 0.002 |
| AJCC 7th Stage | IB/IA | 0.69 (0.26-1.86) | 0.467 | 1.17 (0.37-3.72) | 0.792 |
| Age | Continous | 0.99 (0.94-1.04) | 0.590 | 0.98 (0.93-1.03) | 0.450 |
| Gender | Male/Female | 0.91 (0.38-2.19) | 0.831 | 0.40 (0.13-1.24) | 0.112 |
| Packyears | ≥20/<20 | 1.29 (0.41-4.04) | 0.666 | | |

Abbreviations:
AJCC, American Joint Committee on Cancer;
HR, hazard ratio;
CI, confidence interval.
*The 4 coding gene classifer and non-coding miR-21 were each categorized based on median.
†All univariate and multivariate models were adjusted for cohort membership for the US/Norway analyses.
‡Upon restaging to AJCC 7th edition, there were 7 cases in the Norway cohort for which it could not be distinguished whether they were TNM stage IB or IA. These are included in univariate analyses and excluded in multivariate analyses.

Figure 15:
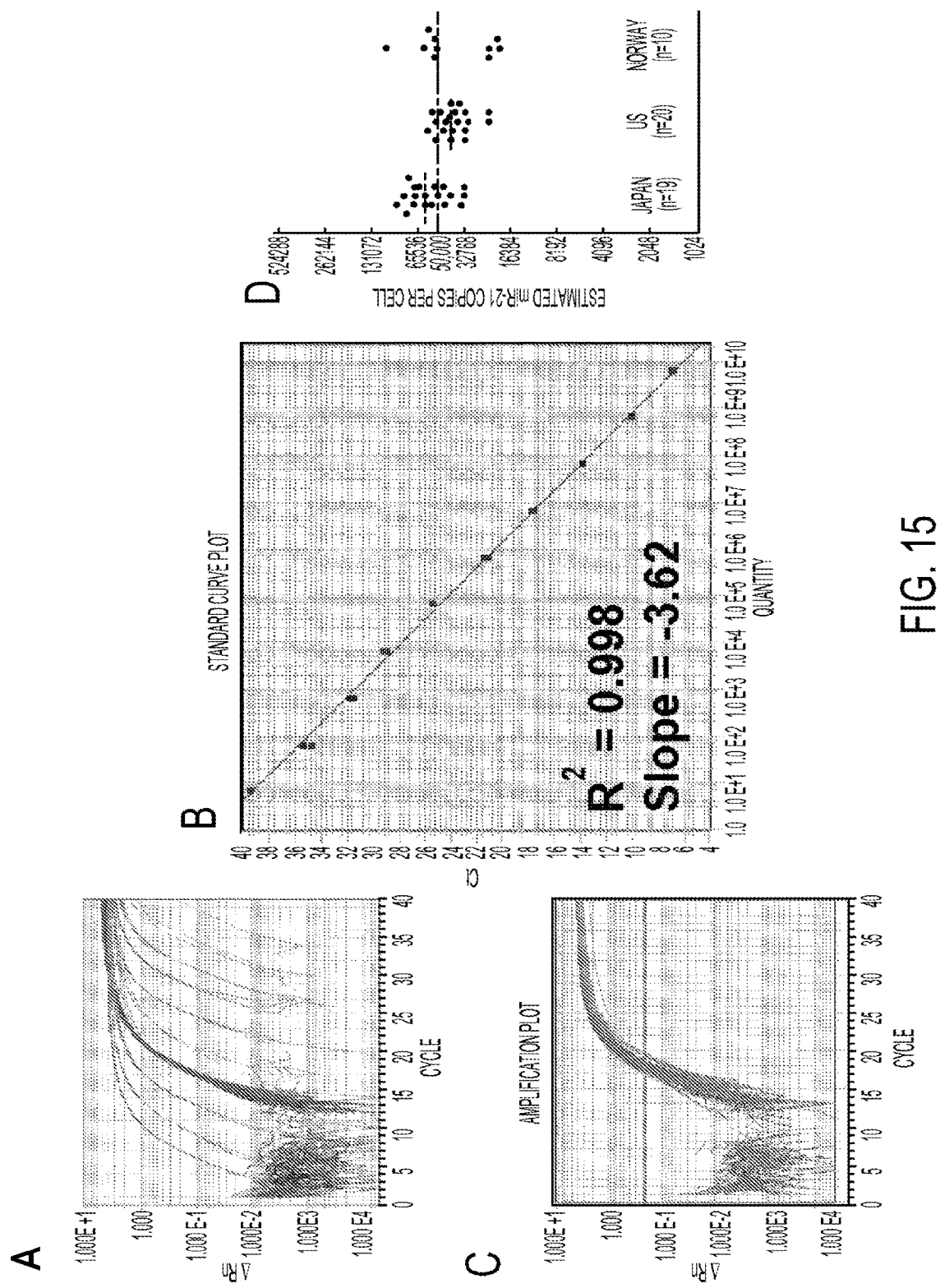
FIG. 15 (A-D) shows estimation of the number of copies of miR-21 per lung tumor cell. (D) shows that lung tumor cells has approximately 50,000 copies of miR-21 per cell on average. This was calculated using a standard curve of serially diluted, synthetic miR-21 and known amounts of tumor RNA. (A) Based on 10-fold dilutions of synthetic miR-21 quantified by qRT-PCR, amplification plot of miR-21 demonstrates a dynamic range of at least 9 logs, detecting as few as six copies of miR-21 per PCR reaction Amplification plot of spiked-in Cel-miR-54 was also shown and shows that all reactions had a similar efficiency of reverse transcription. (B) The resulting Ct values were used to construct a standard curve of miR-21 to calculate absolute copy numbers. (C, D) Using lung tumor RNA samples (n=49) from 3 independent cohorts, miR-21 copies were estimated to be approximately 50,000 per cell (assuming 20 pg total RNA per cell).
Figure 16:
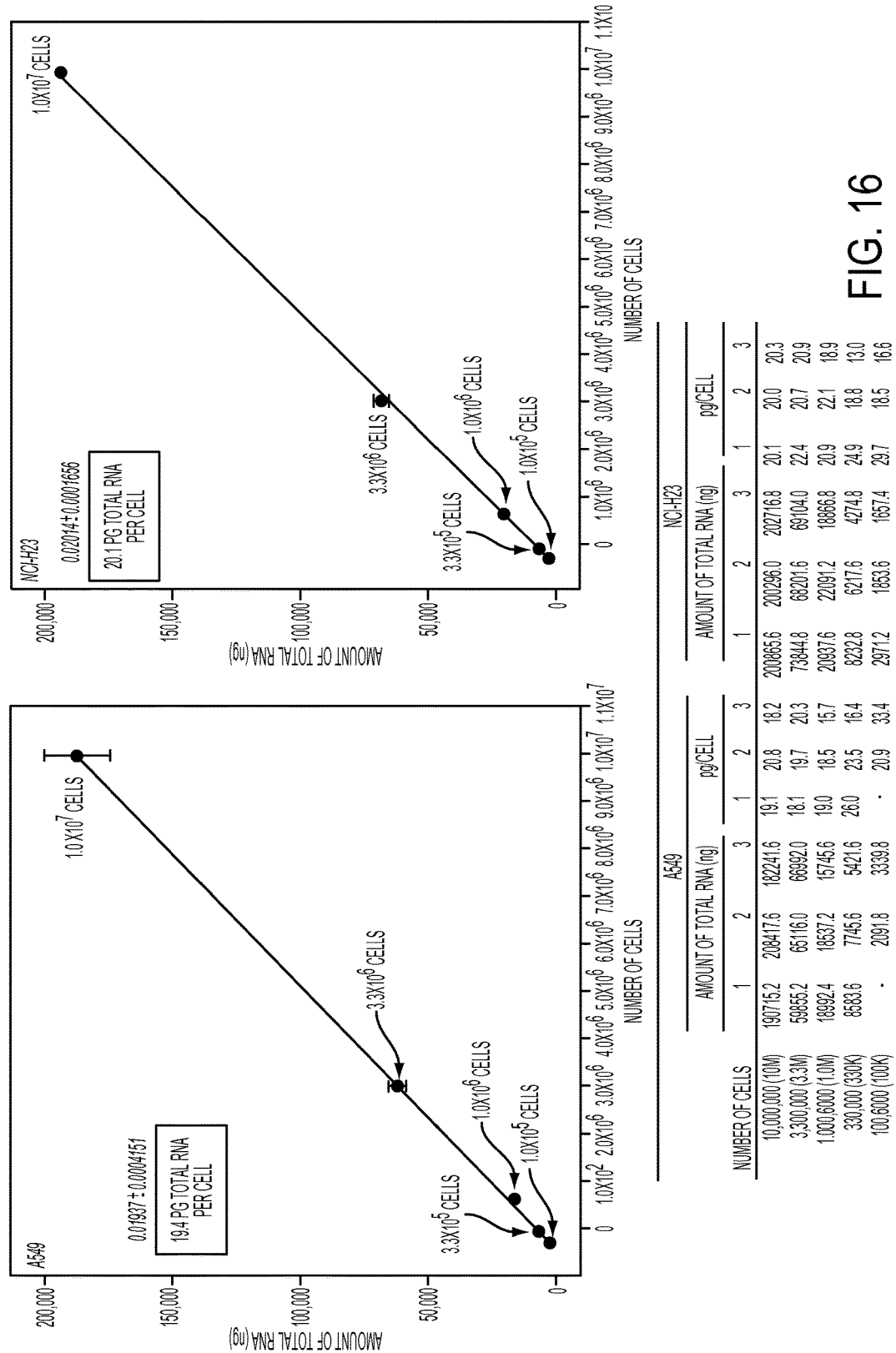
FIG. 16 includes graphs that show the total RNA per cell for the lung cancer cell lines A549 and NCI-H23 was estimated to be 19.4 pg/cell and 20.1 pg/cell respectively

While it is clear that increased miR-21 expression is associated with poor survival, it is unclear what this expression level is in terms of copies per cell. It was next estimated that lung tumor cells has approximately 50,000 copies of miR-21 per cell on average. This was calculated using a standard curve of serially diluted, synthetic miR-21 (FIG. 15) and known amounts of tumor RNA. The total RNA per cell for the lung cancer cell lines A549 and NCI-H23 was estimated to be 19.4 pg/cell and 20.1 pg/cell respectively (FIG. 16). Therefore, 20 pg of RNA per tumor cell was used to calculate copies of miR-21 per tumor cell. These copy number estimates are similar to other published estimates for lung tissue (Lee E J, Baek M, Gusev Y, Brackett D J, Nuovo G J, Schmittgen T D. Systematic evaluation of microRNA processing patterns in tissues, cell lines, and tumors. RNA. 2008; 14:35-42.).

Example 6: Effect of Tumor Heterogeneity on the Four Coding Gene Classifier and Noncoding miR-21

Figure 18:
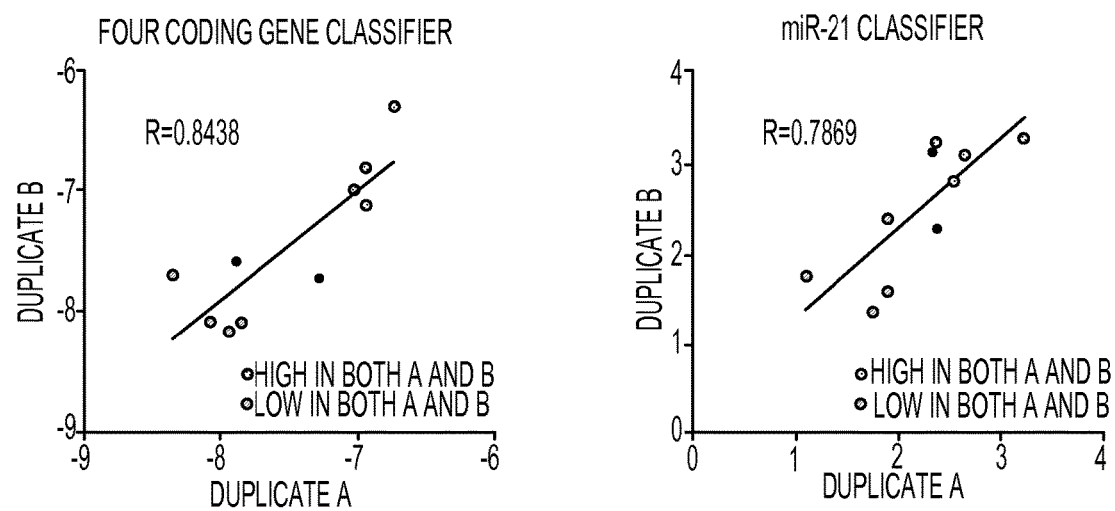
FIG. 18 are graphs that show that both miR-21 and the four coding gene classifiers are highly reproducible in different piece of tissue suggesting the measurements from a single biopsy are sufficient.

It was also tested in further experiments how tumor heterogeneity may affect both the protein coding gene classifier and miR-21 by examining two different pieces of the same tumor. It was found that both miR-21 and the four coding gene classifiers are highly reproducible in different piece of tissue from the same tumor suggesting the measurements from a single biopsy are sufficient (FIG. 18).

The objective of the studies described herein was to build a prognostic gene classifier for early stage lung cancer to help guide clinical decisions. As described in detail herein, a prognostic gene classifier was identified and validated in five independent patient cohorts. The robust associations of the four coding gene classifier with prognosis were significant in stage I patients across ethnically and geographically-diverse populations, indicating that the gene classifier can be used to identify high risk, early stage lung cancer patients who may benefit from adjuvant chemotherapy.

The associations of the four coding gene classifier with prognosis were significant in stage I patients across ethnically and geographically-diverse populations, suggesting that this classifier has potential to identify high risk, early stage lung cancer patients who may benefit from adjuvant chemotherapy.

The current standard of care for stage I NSCLC is lobectomy and mediastinal lymph node dissection, without adjuvant chemotherapy. There is a need for biomarkers to identify stage IA patients who might benefit from adjuvant therapy, and stage IB patients who could be spared from adjuvant chemotherapy. It is a finding of the present invention that this four coding gene classifier comprising HIF1A, DLC1, BRCA1, and XPO1 can be used to guide therapeutic decisions for stage I patients. Stage I patients defined as high risk may be suitable for earlier or more aggressive intervention. Some studies suggest that TNM stage IB patients should be given postoperative adjuvant chemotherapy (Kato H, et al. A randomized trial of adjuvant chemotherapy with uracil-tegafur for adenocarcinoma of the lung. N Engl J Med. 2004; 350:1713-21; Roselli M, et al. Postsurgical chemotherapy in stage IB nonsmall cell lung cancer: Long-term survival in a randomized study. Int J Cancer. 2006; 119:955-60), while others do not agree (Winton T, et al. Vinorelbine plus cisplatin vs. observation in resected non-small-cell lung cancer. N Engl J Med. 2005; 352:2589-97; Douillard J Y, et al. Adjuvant vinorelbine plus cisplatin versus observation in patients with completely resected stage IB-IIIA non-small-cell lung cancer (Adjuvant Navelbine International Trialist Association [ANITA]): a randomised controlled trial. Lancet Oncol. 2006; 7:719-27; Wakelee H, et al. Optimal adjuvant therapy for non-small cell lung cancer—how to handle stage I disease. Oncologist. 2007; 12:331-7.). NCCN guidelines indicate that recurrent NSCLC or metastases should be evaluated for the presence of EGFR mutations or EML4-ALK fusions to help determine appropriate therapies. Future studies should address if the four coding gene classifier presented here can be used alone or with EGFR and ALK status to help provide guidance on which therapies should be given to high risk, early stage patients.

Figure 17:
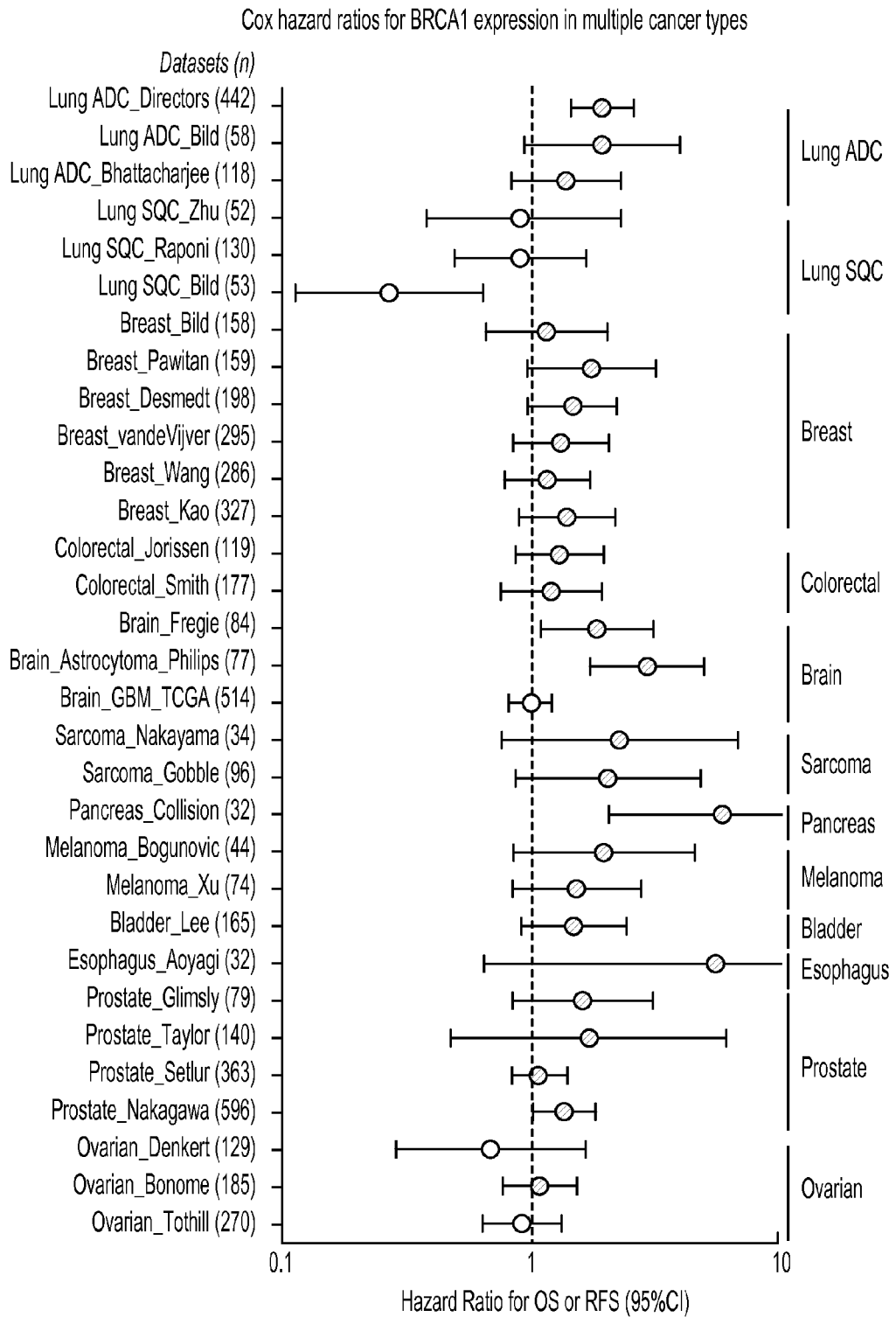
FIG. 17 shows that in addition to the lung cancer cohorts presented in this study, increased BRCA1 expression is associated with worse prognosis of other types of human cancer.

HIF1A, DLC1, XPO1, and BRCA1 have all been implicated in cancer biology and may be causally associated with aggressive disease. Therefore, the altered expression of any of these genes may alter tumor biology to create more aggressive tumors that are either more likely to metastasize or will rapidly develop resistance chemotherapies. HIF1A overexpression is a common event in multiple types of carcinomas and has been associated with aggressive tumor behavior and overall poor prognosis (Giatromanolaki A, et al. Br J Cancer. 2001; 85:881-90; Birner P, et al. Cancer Res. 2000; 60:4693-6; Zhong H, et al. Cancer Res. 1999; 59:5830-5; Aebersold D M, et al. Expression of hypoxia-inducible factor-1alpha: a novel predictive and prognostic parameter in the radiotherapy of oropharyngeal cancer. Cancer Res. 2001; 61:2911-6.). HIF1A was part of a lung cancer prognostic classifier reported by Lau et al. (J Clin Oncol. 2007; 25:5562-9) XPO1 can modulate both nuclear processing and nuclear-cytosolic transport of microRNAs (Bussing I, et al. EMBO J. 2010; 29:1830-9; Castanotto D, et al. Proc Natl Acad Sci USA. 2009; 106:21655-9.), BRCA1 (Brodie K M, et al. J Biol Chem. 2012; 287:7701-16.), and TP53 (Cai X, et al. Proc Natl Acad Sci USA. 2008; 105:16958-63; Freedman D A, et al. Mol Cell Biol. 1998; 18:7288-93.), XPO1 was also part of a lung cancer prognostic classifier reported by Wang et al. (Wan Y W, et al. PLoS One. 2010; 5:e12222) DLC1 is a tumor suppressor gene frequently deleted or silenced in many tumor types, including lung (Yuan B Z, et al. Oncogene. 2004; 23:1405-11; Durkin M E, et al. J Cell Mol Med. 2007; 11:1185-207). In particular, DLC1 methylation was significantly associated with the presence of lung metastatic disease (Castro M, et al. J Transl Med. 2010; 8:86). Germline mutation of BRCA1 is most notably associated with familial susceptibility to breast and ovarian cancers (Black D M, et al. Trends Genet. 1993; 9:22-6). However, BRCA1 overexpression leads to resistance to chemotherapeutic drugs, owing to its role in DNA repair and anti-apoptotic cellular pathways (Kennedy R D, et al. J Natl Cancer Inst. 2004; 96:1659-68). However, a recent study showed that high expression of BRCA1 mRNA was an indicator of poor prognosis lung cancer patients that did not receive adjuvant chemotherapy (Rosell R, et al. PLoS One. 2007; 2:e1129). The Japan cohort in this study is composed primarily of patients who did not receive adjuvant chemotherapy. Thus, the pro-survival role of BRCA1 may extend beyond enhanced chemotherapeutic resistance to encompass resistance to endogenous oxidative damage (Saha T, et al. J Biol Chem. 2010; 285:19092-105). In addition to the lung cancer cohorts presented in this study, increased BRCA1 expression is associated with worse prognosis of other types of human cancer (FIG. 17). BRCA1 has multiple functions including DNA repair and DNA recombination (Silver D P, et al. Cancer Discov. 2012; 2:679-84.). BRCA1 may enhance DNA repair of the endogenous DNA double strand breaks which are found at higher levels in tumors (Halazonetis T D, et al. Science. 2008; 319:1352-5.). Therefore, elevated BRCA1 may increase cancer cell survival and contribute to the poor prognosis of lung cancer cases and further studies are warranted. Several clinical studies are currently recruiting Stage II-IV NSCLC patients with the purpose of studying BRCA1 mRNA levels in association with chemotherapy (NCT00478699, NCT00617656, and NCT00705549 at the ClinicalTrials.gov registry).

In the studies described herein, the combination of the coding gene classifier and miR-21 proved superior at predicting prognosis than either alone. Overexpression of miR-21 has been described across solid tumors, including lung cancer (Saito M. et al. 2011, Volinia S, et al. Proc Natl Acad Sci USA. 2006; 103:2257-61). This is the first report estimating copy numbers per cell for miR-21 in lung tumors. Measurement of miR-21 by Nanostring Human microRNA assays may be a more robust prognostic classifier than measuring miR-21 by qRT-PCR. Without being limited as such, a possible reason for this is that the Nanostring assays used five highly expressed microRNAs as normalization controls and this may be more stable than using RNU66 as a normalization control, as described in Saito M., et al. 2011.

miR-21 has an oncogenic role in lung cancer. OncomiR addition to miR-21 has been demonstrated in an animal model (Medina P P, et al. Nature. 2010; 467:86-90.). In a mouse model of NSCLC, miR-21 overexpression enhanced tumorigenesis and its deletion reduced it, providing a direct link between miR-21 and lung carcinogenesis (Hatley M E, et al Cancer Cell. 2010; 18:282-93.). miR-21 targets many genes (Schetter A J, et al. Cancer J. 2012; 18:244-52.) involved in the cancer cell phenotypes associated with the Hallmarks of Cancer (Hanahan D, et al. Cell. 2011; 144: 646-74.). In addition, miR-21 decreases SOD3 (Zhang X, et al. Cancer Res. 2012; 72:4707-13.) and increases resistance to the induction apoptosis in lung cancer cells (Seike M, et al. Proc Natl Acad Sci USA. 2009; 106:12085-90). These and other studies identify miR-21 as a potential therapeutic target for lung cancer (Croce C M, et al. Nat Med. 2011; 17:935-6).

In conclusion, the results reported herein provide supporting evidence for the use of coding and non-coding gene expression analysis within a clinical setting to help guide therapeutic decisions in lung adenocarcinoma, particularly, stage I.

Example 7: Meta-Analysis of a Four-Gene Classifier as a Prognostic Classifier for Stage I Lung Adenocarcinoma Previously, a prognostic classifier based on the mRNA expression levels of four genes has been developed and validated. This four-gene classifier may help identify stage I lung adenocarcinoma patients at high risk of disease progression and guide therapeutic decisions for these patients. The initial studies evaluated patients from five independent cohorts from various regions of the world, suggesting that the four-gene classifier was robust and representative of most lung adenocarcinomas. In an attempt to further validate this classifier, it has been tested in every publically available dataset that could be identified through Gene Expression Omnibus or Oncomine. Described herein is a meta-analysis of 12 cohorts consisting of 1069 TNM stage I lung adenocarcinoma patients. The meta-analysis found consistent results across all cohorts with no evidence of heterogeneity (I2=0.0%, p=0.98). The four gene classifier was significantly associated with prognosis in ten of the twelve cohorts (p<0.05). The pooled estimate found the prognostic classifier associated with prognosis in all stage I (Hazard Ratio [HR], 2.66; 95% Confidence Interval [CI], 1.93-3.67; P<0.0001) patients and in stratified analyses of stage IA (HR, 2.69; 95% CI, 1.66-4.35; P<0.0001) and stage IB (HR, 2.69; 95% CI, 1.74-4.16; P<0.0001) patients. These results suggest that the four-gene classifier may have clinical utility to further stratify early stage patients into risk to guide therapeutic decisions. The four-gene classifier was not associated with prognosis in patients with squamous cell carcinoma histology indicating that it may only have utility in lung adenocarcinomas.

Selection of Studies

Figure 19:
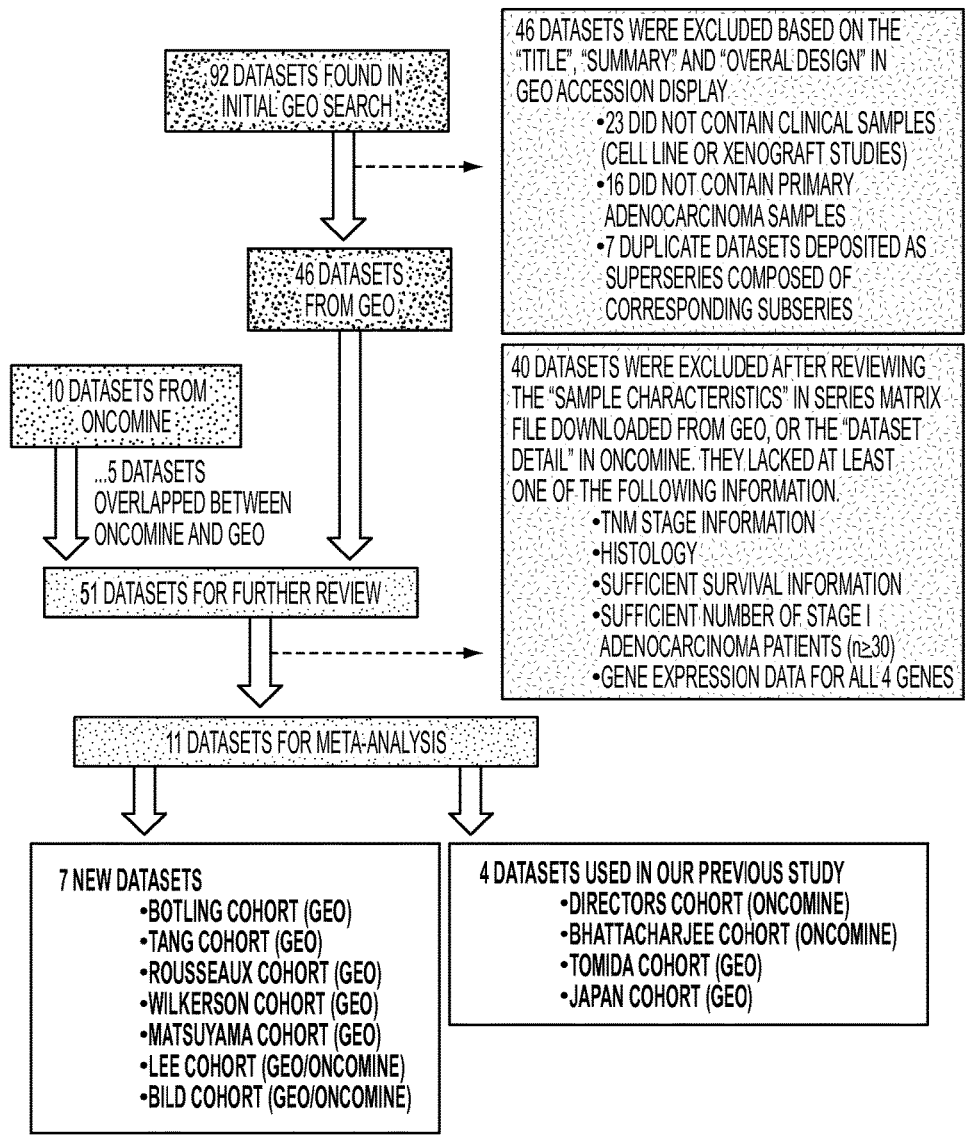
FIG. 19 is a schematic showing a data selection flowchart.

GEO (Gene Expression Omnibus; http://www.ncbi.nlm.nih.gov/geo/) was searched in June 2013 with the search terms "lung cancer", "non-small cell lung cancer", "lung adenocarcinoma", "lung adenocarcinomas" and "NSCLC". The retrieved GEO series were filtered by Organism (*Homo Sapiens*) and Series Type (Expression Profiling by Array) as well as sorted by the number of samples (series that have more than 30 samples). Ninety two GEO series identified by the initial GEO search were screened on the basis of their Title, Summary and Overall Design as described in GEO Accession Display. Datasets were excluded if they analyzed only cell lines/xenograft samples, only non-tumor specimens (e.g., bronchial epithelial cells, blood, fluid), or contained no primary ADC tumors. Also, several superseries that consisted one or more subseries were excluded (due to duplicate data) and the corresponding subseries with gene expression data were retrieved, leaving 46 GEO datasets of lung cancer-related clinical studies. In parallel with this search, ONCOMINE (Compendia Bioscience, Ann Arbor, Mich.; http://www.oncomine.com) was used to identify public microarray datasets that had ADC patients with survival status. ONCOMINE search identified 10 datasets, 5 of which were not deposited in GEO. The resulting 51 datasets containing primary ADC samples were further reviewed based on the Sample Characteristics in Series Matrix File, or the Dataset Detail in ONCOMINE. Selection criteria for all publicly available datasets required each dataset to include survival information for more than 30 TNM stage I patients of ADC and have expression data for BRCA1, HIF1A, DLC1 and XPO1. After removing 40 datasets that did not fit the criteria, 11 independent microarray datasets were found, including the Botling (GSE37745) (Botling, J. et al. Clin Cancer Res, 19: 194-204, 2013.), Tang (GSE42127) (Tang, H., et al. Clin Cancer Res, 19: 1577-86, 2013.), Rousseaux (GSE30219) (Rousseaux, S., et al. Sci Transl Med, 5: 186ra66, 2013.), Matsuyama (GSE11969) (Matsuyama, Y., et al. Mol Carcinog, 50: 301-9, 2011.), Wilkerson (GSE26939) (Wilkerson, M. D., et al. PLoS One, 7: e36530, 2012), Lee (GSE8894/ONCOMINE) (Lee, E. S., et al. Clin Cancer Res, 14: 7397-404, 2008), Bild (GSE3141/ONCOMINE) (Bild, A. H., et al. Nature, 439: 353-7, 2006.) cohorts as well as the Bhattacharjee (ONCOMINE) (Bhattacharjee, A., et al. Proc Natl Acad Sci USA, 98: 13790-5, 2001.), Directors (ONCOMINE) (Shedden, K., et al. Nat Med, 14: 822-7, 2008.), Japan (GSE31210) (Okayama, H., et al. Cancer Res, 2011.), Tomida (GSE13213) (Tomida, S., et al. J Clin Oncol, 27: 2793-9, 2009.) cohorts. Among them, the former 7 cohorts were newly obtained from GEO or ONCOMINE (if available) for this present study, whereas the latter 4 datasets were the original cohorts that were already analyzed in a previous study (Akagi, I., et al. Cancer Res, 73: 3821-3832, 2013.). The selection flowchart and the list of retrieved datasets are presented in FIG. 19 and in the Table in FIG. 20.

For the 4-coding gene analyses in SQC patients, multiple cohorts of stage I SQC were used. Six cohorts, including the Botling, Rousseaux, Tang, Matsuyama, Lee and Bild datasets among the ADC datasets mentioned above, were included, as these cohorts also contained expression data for squamous cell carcinoma (SQC) patients with survival information. One SQC dataset was obtained from GEO (GSE17710) deposited by Wilkerson et al. (Wilkerson, M. D., et al. Clin Cancer Res, 16: 4864-75, 2010.), separated from their ADC data (GSE26939, the Wilkerson ADC cohort) (Wilkerson, M. D., et al. PLoS One, 7: e36530, 2012.). Additionally, among 3 SQC datasets with survival information which were found in ONCOMINE, including the Raponi (SQC only) (Raponi, M., et al. Cancer Res, 66: 7466-72, 2006.), Larsen (SQC only) (Larsen, J. E., et al. Carcinogenesis, 28: 760-6, 2007.) and Zhu (ADC and SQC) (Zhu, C. Q., et al. J Clin Oncol, 28: 4417-24, 2010.) cohort, the Raponi and the Zhu cohorts were included in SQC analyses. For the Zhu cohort, only SQC patients were analyzed, while ADC patients (n=14, Stage I) were disregarded, since considerable number of ADC patients were already used as a part (CAN/DF) of the Directors cohort (Zhu, C. Q., et al. J Clin Oncol, 28: 4417-24, 2010.). The Larsen cohort was excluded because BRCA1 gene was not available in their platform.

Gene Expression Data Analysis

This study focused on stage I patients. The 4-coding gene analysis of five original cohorts used AJCC TNM 6th edition as described previously (Akagi, I., et al. Cancer Res, 73: 3821-3832, 2013). Concerning 7 new cohorts, although the TNM edition was not specified as either 6th or 7th in each of original papers, it was assumed that they were based on AJCC TNM 6th edition, since most tumors were collected before the development of TNM 7th edition in 2009. For the Rousseaux cohort, T1N0 tumors were defined as stage IA, while T2N0 tumors were defined as stage IB, according to the provided TNM classification for each patient. Among all available stage I cases obtained from the public datasets, 2 ADCs and 1 SQC in the Tang cohort, 3 ADCs and 4 SQCs in the Lee cohort were excluded from the analysis, since survival information was not provided for those cases.

For all analyses, the normalized expression values were obtained from each dataset and were not processed further. To build the 4-gene classifier using microarray expression data, criteria were generated to select the most reliable, informative probes. In brief, pairwise correlation of each probe of the same gene was analyzed using stage I ADC cases in each cohort, and then probes that are correlated with any other probe, otherwise the probe with the highest expression were selected for each platform (shown in Table 7, below).

If more than one probe was selected, they were averaged. The 4-coding gene classifier [(0.104×BRCA1)+(0.133×HIF1A)+(−0.246×DLC1)+(0.378×XPO1)] was applied to all newly-obtained cohorts using microarray expression data, and the resulting classifier score was categorized as low, medium, or high based on tertiles. The association between the 4-coding gene classifier and survival was assessed by the Kaplan-Meier log-rank test for trend using Graphpad Prism v5.0 (Graphpad Software Inc). Cox regression analyses were carried out using SPSS 11.0 (SPSS Inc), and all univariate and multivariate models were adjusted for cohort membership where appropriate. Forest plot analyses were performed using Stata 11.2 (Staga-Corp LP). Heterogeneity test for the combined HR was carried out using the I-squared statistics (Higgins, J. P., et al. BMJ, 327: 557-60, 2003.).

Eligible Studies

Since the purpose of this gene expression-based classifier is to identify high-risk, stage I ADC patients who may benefit from additional intervention after surgery, all the analyses in this study were limited to stage I primary ADC tumors. The systematic search identified 11 microarray datasets consisting of more than 30 cases of stage I ADC patients that had sufficient survival information with gene expression data for all 4 genes, including BRCA1, HIF1A, DLC1 and XPO1, as described in FIG. 19 and the Table in FIG. 20. Four of the 11 datasets were previously analyzed in a recent paper in which 5 independent cohorts of stage I ADCs were each analyzed by qRT-PCR and/or microarrays. Hence, 7 independent cohorts were newly obtained through this systematic search and a total of 12 cohorts were included in this study. The characteristics of the 12 cohorts are summarized in Table 8, below.

TABLE 7

Selected probes for each platform.

| Cohort | Platform | BRCA1 | HIF1A | DLC1 | XPO1 |
|---|---|---|---|---|---|
| Rousseaux, Botling, Lee, Bild | Affymetrix U133 + 2 | 204531_s_at 211851_x_at | 200989_at | 210762_s_at 220511_s_at 220512_at 221822_at 242031_x_at | 206775_at 235827_at 244012_x_at |
| Wilkerson | Agilent 44K Custom | 13978_NM_007295_1_6483 14269_NM_007296_1_7137 21991_A_23_P207400 32305_A_23_P207400 32788_NM_007295_1_7137 35600_NM_007395_1_6483 | 7818_A_24_P56388 37872_NM_001636_1 | 4258_A_23_P112016 349926141_A_23_P252721 36819_A_24_P940115 | 17386_A_P40078 |
| Matsuyama | Agilent 21.6K Custom | A_23_P207400 | A_23_P48637 | A_23_P112016 A_23_P252721 | A_23_P40070 |
| Tang | Illumina WG6 V3 | ILMN_1666652 ILMN_1771065 ILMN_1738027 ILMN_2311089 | ILMN_1681283 ILMN_1763260 ILMN_2379788 | ILMN_1638028 ILMN_1729409 | ILMN_1725121 |

Selected probes are highlighted in red.

TABLE 8

Twelve independent cohorts of stage I, lung adenocarcinoma patients

| Cohorts | Country | n | TNM Stage IA | TNM Stage IB | IA or IB | Age Mean | Gender M | Gender F | Smoker (%) | Postoperative Therapy CT/RT | Postoperative Therapy None | Un-known | Outcome | Platform | GEO ID |
|---|---|---|---|---|---|---|---|---|---|---|---|---|---|---|---|
| Five cohorts | | | | | | | | | | | | | | | |
| Japan | Japan | 149 | 100 | 49 | 0 | 59.7 | 66 | 83 | 45.6 | 0 | 149 | 0 | RFS | qRT-PCR | — |
| US/Norway | USA (UMD), Norway | 67 | 29 | 38 | 0 | 64.6 | 37 | 30 | 96.9 | 4 | 43 | 20 | CSS | qRT-PCR | — |
| Directors | USA (MSK, HLM, CAN/ DF, UM) | 276 | 114 | 162 | 0 | 64.4 | 131 | 145 | NA | 46 | 157 | 73 | OS[a] | Affymetrix U133A | NA[b] |
| Bhattacharjee | US (Harvard) | 76 | 35 | 40 | 1 | 64.2 | 32 | 44 | 90.8 | 0 | 0 | 76 | OS[a] | Affymetrix U95A | NA[b] |
| Tomida | Japan | 79 | 42 | 37 | 0 | 61.4 | 41 | 38 | 50.6 | 0 | 79 | 0 | OS[a] | Agilent 44K | GSE13213 |
| Seven new cohorts | | | | | | | | | | | | | | | |
| Tang | USA (MD Anderson) | 87 | 32 | 55 | 0 | 64.1 | 37 | 50 | NA | 22 | 65 | 0 | OS[a] | Illumina WG6 V3 | GSE42127 |
| Rousseaux | France | 81 | 73 | 8 | 0 | 61.8 | 65 | 16 | NA | 0 | 0 | 81 | OS[a] | Affymetrix U133 + 2 | GSE30219 |
| Botling | Sweden | 70 | 28 | 42 | 0 | 63.5 | 31 | 39 | NA | 5 | 31 | 34 | OS[a] | Affymetrix U133 + 2 | GSE37745 |
| Wilkerson | USA (UNC) | 62 | 31 | 31 | 0 | 65.6 | 26 | 36 | 58.0 | 0 | 0 | 62 | OS[a] | Agilent 44K custom | GSE26939 |
| Matsuyama | Japan | 52 | 28 | 24 | 0 | 62.3 | 28 | 24 | 46.2 | 0 | 0 | 52 | OS[a] | Agilent 21.6K custom | GSE11969 |
| Lee | Korea | 36 | 13 | 23 | 0 | 61.4 | 16 | 20 | 38.9 | 0 | 0 | 36 | RFS | Affymetrix U133 + 2 | GSE8894[b] |
| Bild | USA (Duke) | 34 | 21 | 9 | 4 | 64.8 | 17 | 17 | NA | 0 | 0 | 34 | OS[a] | Affymetrix U133 + 2 | GSE3141[b] |
| Total | | 1069 | 546 | 518 | 5 | 63.1 | 527 | 542 | | 77 | 524 | 468 | | | |

NOTE:
[a]Nine cohorts with overall survial information were used in the combined analysis (n = 817).
[b]Data were obtained from ONCOMINE.
Abbreviation: CT/RT, chemotherapy and/or radiotherapy; NA, not available; RFS, relapse-free survival; CSS, cancer-specific survival; OS, overall survival.

The analysis described herein includes 1069 patients in total, consisting of 546 stage IA and 518 stage IB cases (5 cases were not specified as stage IA or IB). These cohorts were derived from 6 different countries, including Japan, Norway, Sweden, France, South Korea, as well as at least 8 different institutions in the United States. Nine of 12 cohorts had overall survival information, while 2 cohorts used relapse-free survival and 1 cohort used cancer-specific survival. In each cohort, RNA samples were isolated from frozen tumor specimens and were subjected to gene expression analysis based on various platforms, including qRT-PCR and Affymetrix, Illumina, or Agilent microarrays.

The 4-Gene Classifier is Tested in 12 Independent Cohorts

Figure 21:
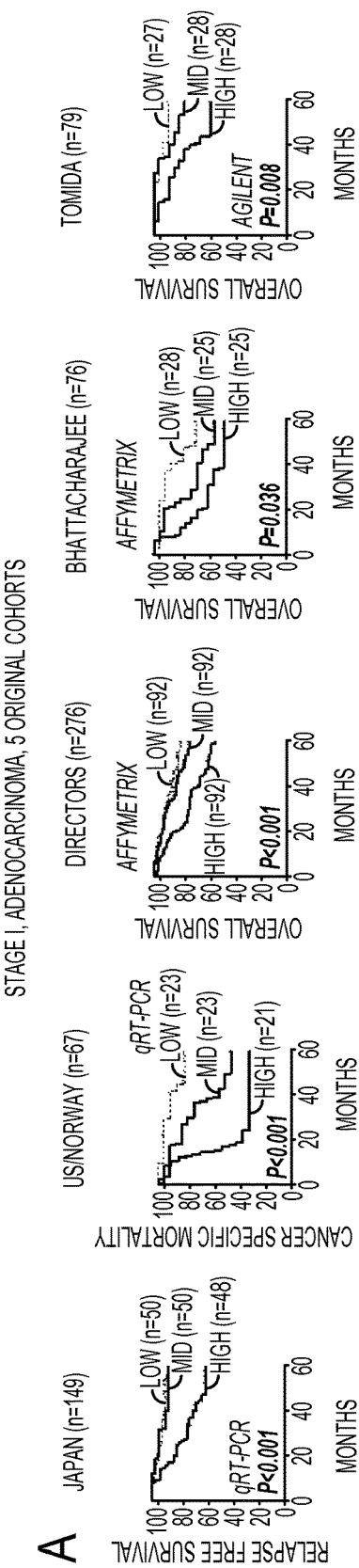
FIG. 21 (A & B) are graphs that show the performance of the 4-coding gene classifier in 12 independent cohorts of stage I lung adenocarcinoma patients (A, 5 original cohorts; B, 7 new cohorts). For each cohort, cases were categorized as high, medium or low based on tertiles. P-values were obtained by the log-rank test for trend.
Figure 21:
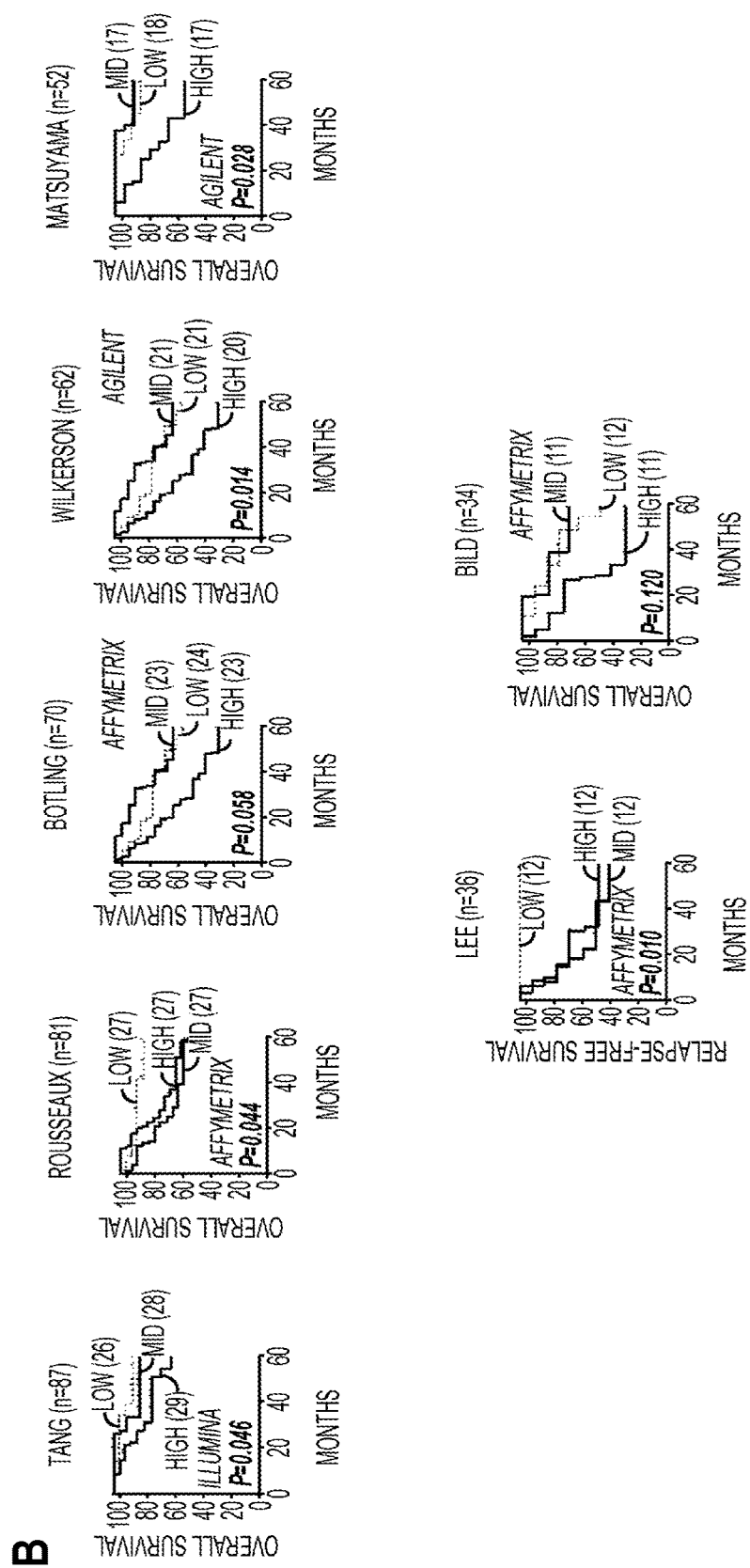

The 4-gene classifier was applied to each of these new cohorts using microarray expression data for 4 genes, and then cases were categorized as high, medium or low, based on tertiles of the classifier score in stage I patients in each cohort. Similar to previously reported results (FIG. 21A), highly concordant associations were found between the 4-gene classifier and prognosis in all 7 newly-obtained cohorts, including the Tang (p=0.046), Rousseaux (p=0.044), Wilkerson (p=0.014), Matsuyama (p=0.028), Lee (p=0.010), Boiling (p=0.058) and Bild (p=0.120) cohorts by the Kaplan-Meier analysis (FIG. 21B).

Meta-Analysis of the 4-Gene Classifier in the Combined Cohort

Figure 22:
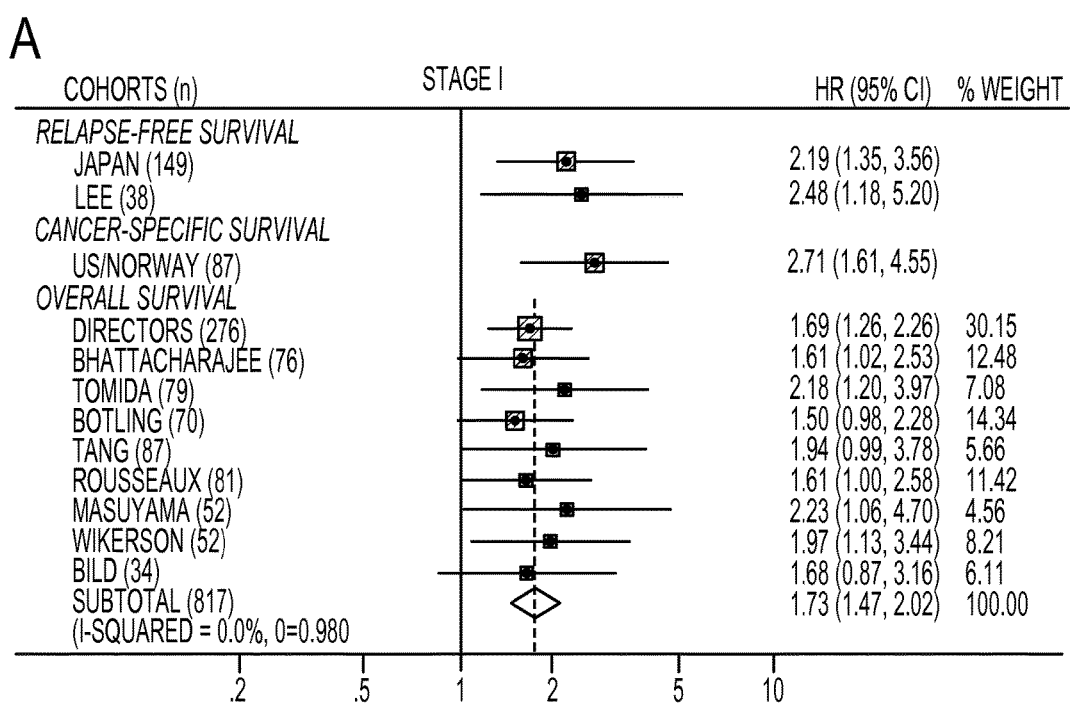
FIG. 22 (A-C) shows meta-analysis of the prognostic impact of the 4-coding gene classifier in 12 independent cohorts of stage I lung adenocarcinoma. The combined analyses included 9 cohorts with overall survival data.
Figure 22:
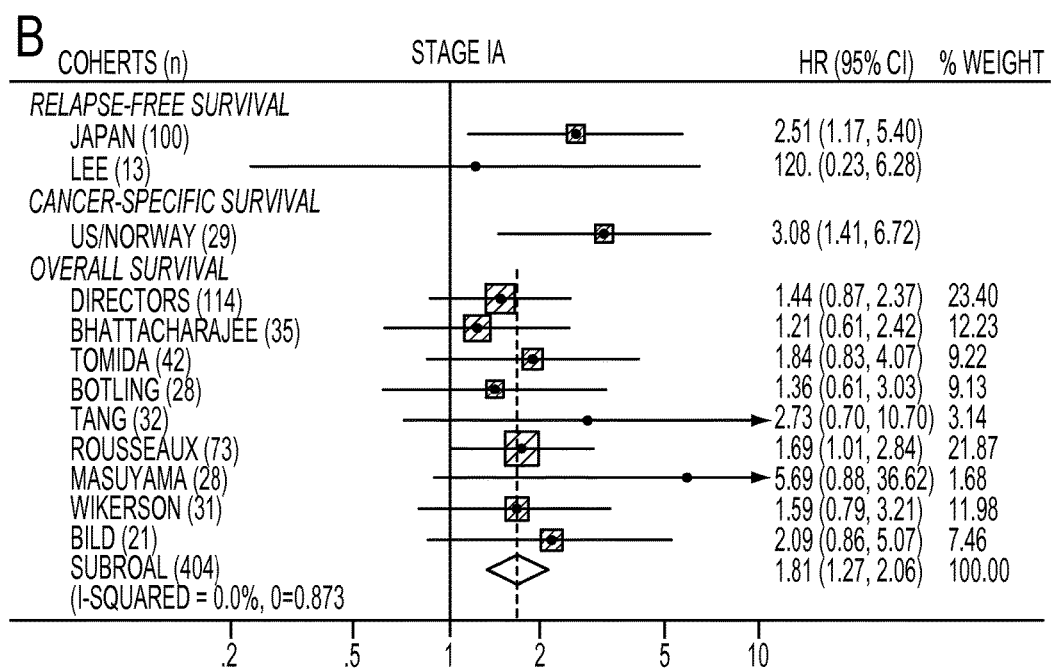
Figure 22:
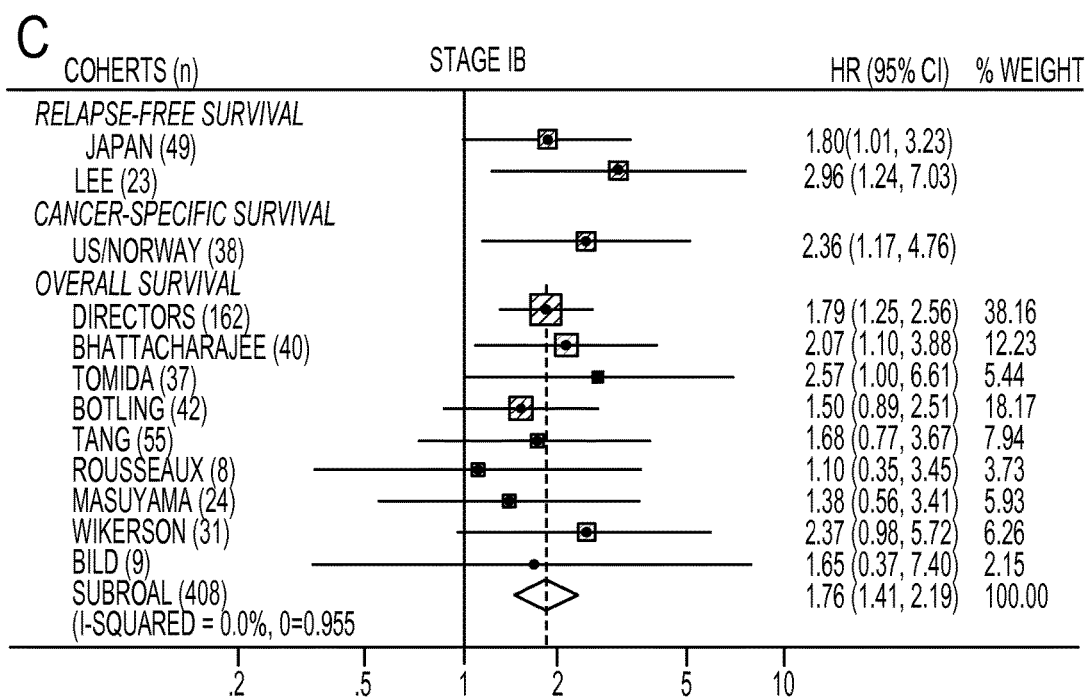

Among 12 cohorts, 9 cohorts with overall survival information were analyzed in the combined model, which included 817 stage I cases. Importantly, neither heterogeneity nor inconsistency across multiple cohorts was detected (I-squared=0.0%, p=0.980) suggesting that these results are representative of most lung adenocarcinomas and not a result of selection bias (FIG. 22). Higher risk patients defined by the classifier were significantly associated with poorer overall survival, with the combined overall trend HR being 1.73 (95% CI, 1.47-2.02) in stage I analysis (FIG. 22A). The corresponding Kaplan-Meier analysis for the combined stage I patients was shown in FIG. 3A. Furthermore, stratified analyses were performed for stage IA and IB separately, to address the prognostic impact of this classifier in these subgroups. Significant associations between the 4-gene classifier and overall survival were found in both stage IA (trend HR, 1.61; 95% CI, 1.27-2.06) and stage IB (trend HR, 1.76; 95% CI, 1.41-2.19) analyses, respectively (FIGS. 2B and C, FIGS. 3B and C).

The 4-Gene Classifier is an Independent Prognostic Biomarker for Stage IA as Well as Stage IB Patients Given that the classifier is significantly associated with survival even in stage IA as well as IB subgroups, Cox regression analysis was conducted using the combined cohort with respect to each stage (Table 9, shown below).

TABLE 9

Univariate and Multivariate Cox regression of the 4-coding gene classifier in the combined cohort[a] of Stage I, adenocarcinoma patients.

|  |  | Univariate analysis[b] | | Multivariate analysis[b] | |
|---|---|---|---|---|---|
| Variable (n) |  | HR (95% CI) | P | HR (95% CI) | P |
| TNM Stage I (n = 817) | | | | | |
| 4 gene classifer[c] | Low (276) | Reference | NA | Reference | NA |
|  | Medium (271) | 1.34 (0.95-1.89) | 0.101 | 1.27 (0.89-1.80) | 0.183 |
|  | High (270) | 2.83 (2.07-3.86) | <0.0001 | 2.66 (1.93-3.67) | <0.0001 |
|  |  | Trend P < 0.0001 | | Trend P < 0.0001 | |
| Stage[d] | IB (408)/IA (404) | 1.68 (1.29-2.19) | 0.0001 | 1.55 (1.09-2.03) | 0.001 |
| Age | Continous | 1.03 (1.02-1.05) | <0.0001 | 1.04 (1.02-1.05) | 0.001 |
| Gender | Female (409)/Male (408) | 0.67 (0.52-0.37) | 0.002 | 0.78 (0.60-1.10) | <0.0001 |
| TNM Stage IA (n = 404) | | | | | |
| 4 gene classifer[c] | Low (149) | Reference | NA | Reference | NA |
|  | Medium (137) | 1.47 (0.87-2.49) | 0.151 | 1.42 (0.84-2.40) | 0.191 |
|  | High (118) | 2.69 (1.67-4.34) | <0.0001 | 2.69 (1.66-4.35) | <0.0001 |
|  |  | Trend P < 0.0001 | | Trend P < 0.0001 | |
| Age | Continous | 1.03 (1.01-1.06) | 0.002 | 1.04 (1.02-1.06) | 0.0007 |
| Gender | Female (205)/Male (199) | 0.61 (0.40-0.91) | 0.016 | 0.65 (0.43-0.99) | 0.043 |
| TNM Stage IB (n = 408) | | | | | |
| 4 gene classifer[c] | Low (125) | Reference | NA | Reference | NA |
|  | Medium (132) | 1.20 (0.74-1.93) | 0.456 | 1.14 (0.71-1.84) | 0.586 |
|  | High (151) | 2.88 (1.88-4.43) | <0.0001 | 2.09 (1.74-4.16) | <0.0001 |
|  |  | Trend P < 0.0001 | | Trend P < 0.0001 | |
| Age | Continous | 1.04 (1.02-1.05) | <0.0001 | 1.03 (1.02-1.05) | <0.0001 |
| Gender | Female (203)/Male (206) | 0.75 (0.54-1.06) | 0.102 | 0.90 (0.64-1.26) | 0.553 |

[a]The combined cohort consists of 9 publicly available, independent microarray datasets of stage: patients with overall survival information, including the Directors (276), Bhattachrjee (76), Tomida (79), Botling (70), Tang (87), Rosseaux (61), Matsuyama (52), Wilkerson (62), and Bild (34) cohorts.
[b]All univariate and multivariate models were adjusted for cohort membership for all analyses.
[c]The 4-coding gene classifier was categorized based on tertiles of Stage I patients for each cohort.
[d]There were a total of 5 stage I cases in the Bhattachrjee (1) and Bild (4) cohorts for which stage IB/IA information is not available. These are included in univariate analyses and excluded in multivariate analyses.

All univariate and multivariate Cox analyses were adjusted for cohort membership, and multivariate models were adjusted for age, gender and TNM stage. Since most of the public datasets did not provide complete clinical information, other parameters, such as smoking status or adjuvant chemotherapy to the Cox analysis, were not applied. In univariate analysis, older age, male gender, TNM stage IB and high-risk patients defined by the classifier were each significantly associated with worse outcome. Multivariate models revealed that the high-risk group was significantly associated with poor overall survival, independent of other parameters, not only in stage I analysis (HR, 2.66; 95% CI, 1.93-3.67; P<0.0001) but stage IA (HR, 2.69; 95% CI, 1.66-4.35; P<0.0001) as well as stage IB (HR, 2.69; 95% CI, 1.74-4.16; P<0.0001) analyses.

The 4-Gene Classifier is Only Applied to Adenocarcinoma Patients

The significance of this classifier was addressed in squamous cell carcinoma (SQC), which is another major histological type of NSCLC. Nine independent cohorts, consisting of 337 stage I SQC patients, were obtained and the 4-gene classifier was applied to each cohort (Table 10, shown below).

TABLE 10

Nine cohorts of stage I, lung squamous cell carcinoma patients

|  |  |  | TNM Stage | | | | | | |
|---|---|---|---|---|---|---|---|---|---|
| Cohorts | Country | n | IA | IB | IA or IB | Outcome | Platform | GEO ID | References |
| Raponi | USA (UM) | 73 | 27 | 46 | 0 | OS[a] | Affymetrix U133A | GSE4573[b] | Cancer Res 2006 |
| Rousseaux | France | 48 | 46 | 2 | 0 | OS[a] | Affymetrix U133 + 2 | GSE30219 | Sci Transl Med 2013 |
| Botling | Sweden | 40 | 8 | 32 | 0 | OS[a] | Affymetrix U133 + 2 | GSE37745 | Clin Cancer Res 2013 |
| Wilkerson | USA (UNC) | 34 | 22 | 12 | 0 | OS[a] | Agilent 44K custom | GSE17710 | Clin Cancer Res 2010 |
| Lee | Korea | 45 | 2 | 43 | 0 | RFS | Affymetrix U133 + 2 | GSE8894[b] | Clin Cancer Res 2008 |
| Bild | USA (Duke) | 33 | 12 | 18 | 3 | OS[a] | Affymetrix U133 + 2 | GSE3141[b] | Nature 2006 |

TABLE 10-continued

Nine cohorts of stage I, lung squamous cell carcinoma patients

| Cohorts | Country | n | TNM Stage IA | TNM Stage IB | TNM Stage IA or IB | Outcome | Platform | GEO ID | References |
|---|---|---|---|---|---|---|---|---|---|
| Zhu | Canada | 25 | 0 | 0 | 25 | OS[a] | Affymetrix U133A | GSE14814[b] | J Clin Oncol 2010 |
| Tang | USA (MD Anderson) | 22 | 9 | 13 | 0 | OS[a] | Illumina WG6 V3 | GSE42127 | Clin Cancer Res 2013 |
| Matsuyama | Japan | 17 | 5 | 12 | 0 | OS[a] | Agilent 21.6K custom | GSE11969 | Mol Carcinog 2011 |
| Total | | 337 | 131 | 178 | 28 | | | | |

[a]Eight cohorts with overall survival information were used in the combined analysis (n = 292).
[b]Data were obtained from ONCOMINE2.0.
Abbreviation: NA, not available; RFS, relapse-free survival; OS, overall survival.

Figure 23:
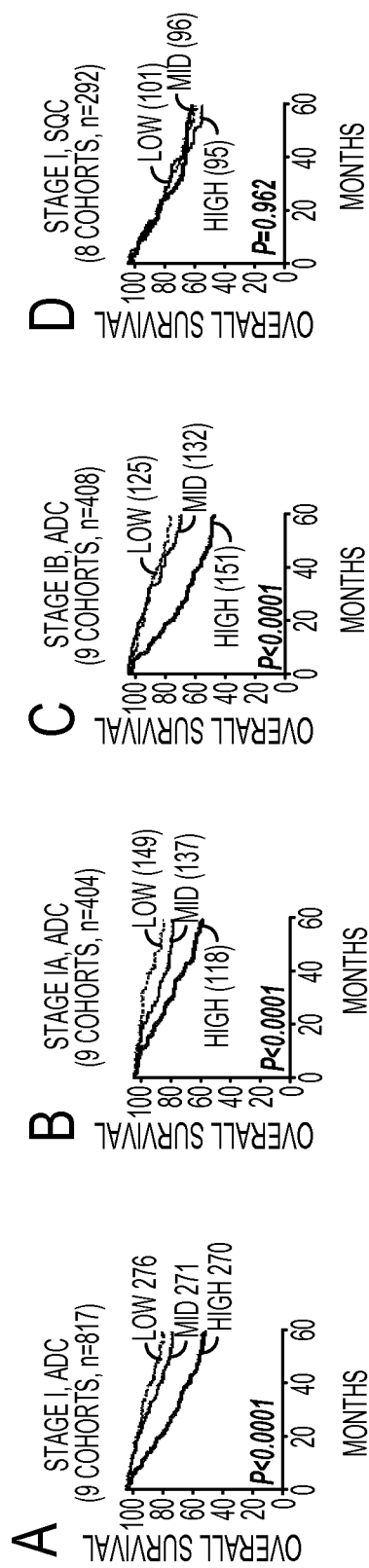
FIG. 23 (A-D) (A) Kaplan-Meier analysis of the 4-coding gene classifier in the combined cohort of stage I lung adenocarcinoma (ADC) patients from 9 independent datasets with overall survival. Cases were categorized as high, medium or low based on tertiles of stage I patients in each cohort. (B), (C) Subgroup analysis on stage IA and IB ADC tumors, respectively. (D) Combined analysis of the 4-coding gene classifier in stage I squamous cell carcinoma (SQC) patients from 8 independent datasets (see also Supplementary FIG. 2). P-values were obtained by the log-rank test for trend.
Figure 24:
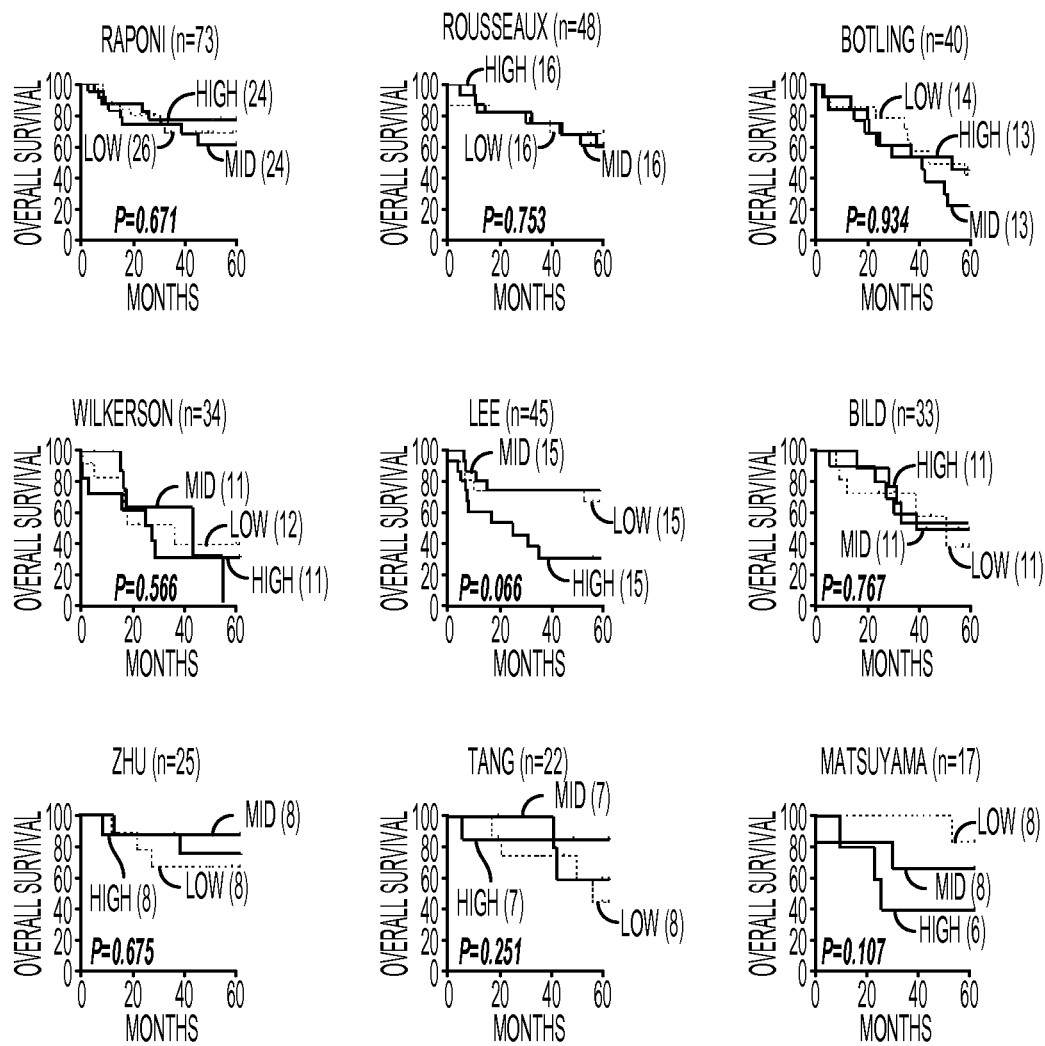
FIG. 24 is a panel of graphs showing the performance of the 4-coding gene classifier in 9 independent cohorts of stage I lung squamous cell carcinoma patients. For each cohort, cases were categorized as high, medium or low based on tertiles. P-values were obtained by the log-rank test for trend.

Also, 8 cohorts that had overall survival information were combined (n=292). However, no significant association was found in any of the SQC analyses (FIG. 23D, FIG. 24), indicating that the 4-gene classifier is specific to ADC. This is reasonable since this classifier was built based on ADC patients only. Also, it is suggested that SQC and ADC are molecularly distinct entities from each other (Herbst, R. S., Heymach, J. V., and Lippman, S. M. Lung cancer. N Engl J Med, 359: 1367-80, 2008).

The present studies were designed to test if the 4-gene classifier that was previously identified is a robust prognostic classifier for early stage lung adenocarcinoma. Every publically available dataset that was available was used in these studies. The 4-gene classifier was a robust classifier for over 1000 TNM Stage I lung adenocarcinoma cases from 12 cohorts. These results were significant when evaluating TNM stage IA or stage IB patients and all associations were independent of available clinical parameters. This is the first report of an RNA-based classifier in lung adenocarcinoma to be tested and validated this extensively. These results suggest that this classifier may help guide therapeutic decisions for early stage lung cancer.

Curative surgery without adjuvant chemotherapy is the standard of care for most TNM stage I patients because there is not clear evidence that adjuvant chemotherapy will benefit this patient population. However, many of these patients have undetectable micro-metastases that may benefit from earlier intervention. The 4-gene classifier has the potential to identify high risk patient populations that are suitable for therapeutic intervention, resulting in improved survival outcomes for this patient group.

The pooled estimate demonstrated that each of the 4 genes, BRCA1, HIF1A, DLC1 and XPO1, were significantly associated with survival in stage I ADC patients in an a pooled analysis of all 12 cohorts of lung adenocarcinoma patients, supporting each of these genes being included in the 4-gene classifier (Table 11)

TABLE 11

| Variable (n) | Univariate Analysis[b] | |
|---|---|---|
| | HR (95% CI) | P |
| TNM Stage I (n = 817) | | |
| BRCA1 | 1.85 (1.52-2.24) | <0.0001 |
| HIF1A | 1.32 (1.12-1.57) | 0.001 |
| DLC1 | 0.78 (0.70-0.87) | <0.0001 |
| XPO1 | 1.38 (1.17-1.64) | 0.0002 |
| TNM Stage IA (n = 404) | | |
| BRCA1 | 2.11 (1.57-2.83) | <0.0001 |
| HIF1A | 1.23 (0.93-1.63) | 0.139 |
| DLC1 | 0.76 (0.64-0.91) | 0.003 |
| XPO1 | 1.12 (0.82-1.15) | 0.486 |
| TNM Stage B (n = 408) | | |
| BRCA1 | 1.63 (1.24-2.14) | 0.0004 |
| HIF1A | 1.32 (1.06-1.65) | 0.014 |
| DLC1 | 0.76 (0.65-0.80) | 0.0006 |
| XPO1 | 1.47 (1.21-1.80) | 0.0001 |

[a]The combined cohort consists of 9 publicly available independent microarray datasets of stage I patients with overall survival information, including the Directors (276), Bhattacharjee (76), Tomida (79), Botling (70), Tang (67), Rousseaux (81), Matsuyama (52), Wilkerson (62), and Bild (34) cohorts.
[b]The expression of 4 genes were each treated as a continuous variable. All models were adjust for cohort membership.

The results reported herein were obtained using the following methods and materials.

Patients and Tissue Samples 291 tumor samples from three cohorts of patients with lung adenocarcinoma from National Cancer Center Hospital, Tokyo, Japan (Japan cohort, n=199), the Metropolitan Baltimore area of the United States (US cohort, n=67) and the Haukeland University Hospital, Bergen, Norway (Norway cohort, n=25) were analyzed. The Japan cohort was recruited from National Cancer Center Hospital between 1998 and 2008. The US cohort was recruited between 1987 and 2009. The Norway cohort (n=25) was recruited between 1988 to 2003. Further information about these cohorts has been described elsewhere (Saito M, et al. Clin Cancer Res. 2011; 17:1875-82).

Primary lung tumors and adjacent noncancerous tissues were procured from patients undergoing surgical resections without preoperative chemotherapy or radiation treatment. Tissues were snap-frozen immediately after surgery and stored at −80° C. Histopathology was classified according to the World Health Organization Classification of Tumor system. Only patients with the diagnosis of pure adenocarcinoma or adenocarcinoma with a bronchioloalveolar carcinoma (BAC) component were used, while those of adenocarcinoma in situ (formerly pure BAC) were excluded.

Patient demographics are listed in Table 1, above. Cases were originally staged based on American Joint Committee on Cancer (AJCC) 6th edition and were restaged to AJCC 7th edition where possible. The US and Norway cohorts showed similar 5-year survival rates, TNM staging, gender and age at diagnosis. Thus, to increase the statistical power for all further analyses, they were combined. All patients consented to tissue specimen collection. This study was performed under the approval of the Institutional Review Board (IRB) at the National Institutes of Health, Regional Committees for Medical and Health Research Ethics in Norway and the IRB for National Cancer Center at Japan.

RNA Isolation and mRNA Measurement

RNA was extracted from frozen tissue samples using TRIZOL (Invitrogen, Carlsbad, Calif.) and was assessed via the Bioanalyzer 2100 system (Agilent Technologies, Santa Clara, Calif.). Data collection was completed while blinded to clinical outcomes. Taqman Gene expression assays (Applied Biosystems, Foster City, Calif.) were loaded into 96.96 dynamic arrays (Fluidigm Corporation, South San Francisco, Calif.) in duplicate and qRT-PCR reactions were performed using BioMark Real-Time PCR System according to manufacturer's instructions (Fluidigm Corporation, South San Francisco, Calif.). Taqman assays included DNMT1 (Assay ID Hs00154749_m1), BRCA1 (ID Hs00173233_m1), HIF1A (ID Hs00936371_m1), CA9 (ID Hs00154208_m1), CCT3 (ID Hs00195623_m1), DLC1 (ID Hs00183436_m1), and XPO1 (ID Hs00418963_m1). 18S (ID Hs03003631_m1), was used as normalization control. Undetectable signals were treated as missing data. To examine the association between the expression of BRCA1 and BRCA1-IRIS, qRT-PCR for BRCA1-IRIS and GAPDH was performed in triplicate using POWER SYBR Green PCR Master Mix (Applied Biosystems), according to manufacturer's instructions with the 7900 HT Fast Real-Time PCR System (Applied Biosystems). Specific primers for BRCA1-IRIS were synthesized according to Chock et al. (Chock, K. L. et al., *Cancer Res.* 2010; 70:8782-91). Twenty cDNA samples in the highest or lowest tertile of BRCA1 expression in the US cohort by Taqman assays were subjected to this analysis. Expression levels of the non-coding microRNA miR-21 were previously measured in all of these patient samples and the methods are described in detail in Saito, M. et al., *Clin. Cancer Res.* 17:1875-82 (2011).

Gene Expression Arrays

Publicly Available Gene Expression Datasets

Microarray data generated using the Japanese cohort (Okayama, H. et al., *Cancer Res.* 72:100-11 (2012)) is available at Gene Expression Omnibus (accession number GSE31210). Additional publically available microarray data, including the Bhattacharjee cohort (Bhattacharjee, A. et al., *Proc. Natl. Acad. Sci. USA* 98:13790-5 (2001)), and National Cancer Institute Director's Challenge cohort (Shedden, K. et al., *Nat. Med.* 14:822-7 (2008)), was used for validation and obtained through ONCOMINE 2.0 (Compendia Bioscience, Ann Arbor, Mich.). The Tomida cohort (Tomida, S. et al., *J. Clin. Oncol.* 27:2793-9 (2009)) was obtained from Gene Expression Omnibus (accession number GSE13213). Selection criteria for all publicly available datasets required each dataset to include survival information for more than 50 TNM stage I patients and have expression data for BRCA1, HIF1A, DLC1 and XPO1. The normalized expression values were obtained from each dataset and were not processed further. To build the gene signature, the expression values for 2 probes corresponding to BRCA1 were averaged in the Oncomine 2.0 cohorts. There were 3 probes (A_23_P252721, A_24_P940115 and A_23_P252721) for DLC1 in the Tomida cohort. A_23_P252721 was excluded because of missing values and the other 2 were averaged.

Statistical Analysis and Gene Classifier Development

Patients were dichotomized based on the median expression value for each gene to evaluate the association between gene expression and survival by the Kaplan-Meier log-rank test using Graphpad Prism v5.0 (Graphpad Software Inc, San Diego, Calif.). Cox regression was performed using Stata 11.2 (StagaCorp LP, College Station, Tex.). Coefficients from multivariate Cox regression models on continuous expression values for BRCA1, HIF1A, DLC1, and XPO1 from the Japan cohort were used to build the four coding gene classifier scores for all cohorts. The association between the four coding gene classifier and survival was assessed for significance by P for trend and by the log-rank test where appropriate. For Cox regression analysis, age was treated as a continuous variable and smoking status was dichotomized into >20 pack years and <20 pack years. Gene expression data, clinical information and stata coding to generate the four coding gene classifier publically available for download (http://www3.cancer.gov/intra/lhc/Supplemental_Data_and_coding_CR.zip).

MicroRNA Measurements

Global microRNA expression patterns were measured with Nanostring Human microRNA assays using 100 ng of total RNA, according to manufacturer's instructions (Nanostring Technologies, Seattle, Wash.). miR-21 expression values were normalized based on the average expression of the 5 most highly expressed miRs that do not include miR-21 (miR-720, miR-26a, miR-126, miR-16 and miR-29a). Using the expression of the 5 highest microRNAs was thought to be more precise than using lower expressed microRNAs as normalization controls.

Absolute Quantification of miR-21 Copies Per Cell by qRT-PCR

To calculate the copies of miR-21 per tumor cell, the total RNA content per cell was first estimated using a series of total RNA extraction from two lung adenocarcinoma cell lines, A549 and NCI-H23. Briefly, trypsinized cells were counted and a series of cell suspension (100K, 330K, 1.0M, 3.3M, 10M cells in triplicate) was pelleted, washed and then subjected to total RNA extraction by Trizol. The total RNA quantity was determined by Nanodrop and this data was used to generate a standard curve to estimate amount of RNA per cell.

Copy numbers of miR-21 were calculated based on comparing levels of miR-21 in lung tumors to a standard curve of serial diluted, synthetic miR-21 (Integrated DNA Technologies, Inc, Coralville, Iowa). Synthetic *C. elegans* miR-54 was added to all samples as a quality control of both reverse transcription and PCR. For 49 tumors from the 3 independent cohorts, 40 ng of total RNA was used for reverse transcription. Real-time PCR was performed in triplicate (miR-21) or duplicate (cel-miR-54). qRT-PCR was performed using standard Taqman PCR protocol as described previously. (Saito M. et al. Clin Cancer Res. 2011; 17:1875-82) Absolute copy number of miR-21 was determined by generating a standard curve of synthetic miR-21.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents, publications, CAS numbers, and accession numbers mentioned in this specification are herein incorporated by reference to the same extent as if each independent patent and publication was specifically and individually indicated to be incorporated by reference.

The invention claimed is:

1. A method for detecting miR-21, BRCA1, HIFIA, DLC1, and XPO1 expression in a subject, the method comprising:
    (a) detecting the mRNA levels of BRCA1, HIFIA, DLC1, and XPO1 in an RNA sample obtained from the lung of the subject by contacting the RNA sample with probes for BRCA1, HIFIA, DLC1 and XPO1 and detecting binding of the probes and the mRNA of BRCA1, HIFIA, DLC1, and XPO1;
    (b) detecting the level of miR-21 in the sample by contacting the sample with a mi-R21 probe and detecting binding of the miR-21 probe and the miR-21.

2. The method of claim 1, wherein the mRNA levels of BRCA1, HIF1A, DLC1, and XPO1 are detected by microarray, RT-PCR, qRT-PCR, nanostring assay, or in situ hybridization.

* * * * *

SEQUENCE LISTING

```
<160> NUMBER OF SEQ ID NOS: 13

<210> SEQ ID NO 1
<211> LENGTH: 7224
<212> TYPE: DNA
<213> ORGANISM: Homo sapiens

<400> SEQUENCE: 1
gtaccttgat ttcgtattct gagaggctgc tgcttagcgg tagccccttg gtttccgtgg      60
caacggaaaa gcgcgggaat tacagataaa ttaaaactgc gactgcgcgg cgtgagctcg     120
ctgagacttc ctggacgggg gacaggctgt ggggtttctc agataactgg gcccctgcgc     180
tcaggaggcc ttcaccctct gctctgggta aagttcattg aacagaaag aaatggattt      240 atctgctctt cgcgttgaag aagtacaaaa tgtcattaat gctatgcaga aaatcttaga     300
gtgtcccatc tgtctggagt tgatcaagga acctgtctcc acaaagtgtg accacatatt     360
ttgcaaattt tgcatgctga aacttctcaa ccagaagaaa gggccttcac agtgtccttt     420
atgtaagaat gatataacca aaaggagcct acaagaaagt acgagattta gtcaacttgt     480
tgaagagcta ttgaaaatca tttgtgcttt tcagcttgac acaggtttgg agtatgcaaa     540
cagctataat tttgcaaaaa aggaaaataa ctctcctgaa catctaaaag atgaagtttc     600
tatcatccaa agtatgggct acagaaaccg tgccaaaaga cttctacaga gtgaacccga     660
aaatccttcc ttgcaggaaa ccagtctcag tgtccaactc tctaaccttg gaactgtgag     720
aactctgagg acaaagcagc ggatacaacc tcaaaagacg tctgtctaca ttgaattggg     780
atctgattct tctgaagata ccgttaataa ggcaacttat tgcagtgtgg gagatcaaga     840
attgttacaa atcacccctc aaggaaccag ggatgaaatc agtttggatt ctgcaaaaaa     900
ggctgcttgt gaatttctg agacggatgt aacaaatact gaacatcatc aacccagtaa      960
taatgatttg aacaccactg agaagcgtgc agctgagagg catccagaaa agtatcaggg    1020
tagttctgtt tcaaacttgc atgtggagcc atgtggcaca aatactcatg ccagctcatt    1080
acagcatgag aacagcagtt tattactcac taaagacaga atgaatgtag aaaaggctga    1140
attctgtaat aaaagcaaac agcctggctt agcaaggagc aacataaca gatgggctgg     1200 aagtaaggaa acatgtaatg ataggcggac tcccagcaca gaaaaaaagg tagatctgaa    1260
tgctgatccc ctgtgtgaga gaaagaatg gaataagcag aaactgccat gctcagagaa    1320
tcctagagat actgaagatg ttccttggat aacactaaat agcagcattc agaaagttaa    1380
tgagtggttt tccagaagtg atgaactgtt aggttctgat gactcacatg atgggagtc     1440 tgaatcaaat gccaaagtag ctgatgtatt ggacgttcta aatgaggtag atgaatattc    1500
tggttcttca gagaaaatag acttactggc cagtgatcct catgaggctt taatatgtaa    1560
aagtgaaaga gttcactcca atcagtaga gagtaatatt gaagacaaaa tatttgggaa    1620
aacctatcgg aagaaggcaa gcctccccaa cttaagccat gtaactgaaa atctaattat    1680
```

```
aggagcattt gttactgagc cacagataat acaagagcgt cccctcacaa ataaattaaa    1740
gcgtaaaagg agacctacat caggccttca tcctgaggat tttatcaaga aagcagattt    1800
ggcagttcaa aagactcctg aaatgataaa tcagggaact aaccaaacgg agcagaatgg    1860
tcaagtgatg aatattacta atagtggtca tgagaataaa acaaaaggtg attctattca    1920
gaatgagaaa atcctaacc caatagaatc actcgaaaaa gaatctgctt tcaaaacgaa     1980
agctgaacct ataagcagca gtaagcaa tatggaactc gaattaaata tccacaattc      2040
aaaagcacct aaaaagaata ggctgaggag gaagtcttct accaggcata ttcatgcgct    2100
tgaactagta gtcagtagaa atctaagccc acctaattgt actgaattgc aaattgatag    2160
ttgttctagc agtgaagaga taaagaaaaa aaagtacaac caaatgccag tcaggcacag    2220
cagaaaccta caactcatgg aaggtaaaga acctgcaact ggagccaaga agagtaacaa    2280
gccaaatgaa cagacaagta aaagacatga cagcgatact ttcccagagc tgaagttaac    2340
aaatgcacct ggttctttta ctaagtgttc aaataccagt gaacttaaag aatttgtcaa    2400
tcctagcctt ccaagagaag aaaaagaaga gaaactagaa acagttaaag tgtctaataa    2460
tgctgaagac cccaaagatc tcatgttaag tggagaaagg gttttgcaaa ctgaaagatc    2520
tgtagagagt agcagtattt cattggtacc tggtactgat tatggcactc aggaaagtat    2580
ctcgttactg gaagttagca ctctagggaa ggcaaaaaca gaaccaaata aatgtgtgag    2640
tcagtgtgca gcatttgaaa accccaaggg actaattcat ggttgttcca agataatag    2700 aaatgacaca gaaggcttta agtatccatt gggacatgaa gttaaccaca gtcgggaaac    2760
aagcatagaa atggaagaaa gtgaacttga tgctcagtat ttgcagaata cattcaaggt    2820
ttcaaagcgc cagtcatttg ctccgttttc aaatccagga aatgcagaag aggaatgtgc    2880
aacattctct gcccactctg ggtccttaaa gaaacaaagt ccaaaagtca cttttgaatg    2940
tgaacaaaag gaagaaaatc aaggaaagaa tgagtctaat atcaagcctg tacagacagt    3000
taatatcact gcaggctttc ctgtggttgg tcagaaagat aagccagttg ataatgccaa    3060
atgtagtatc aaaggaggct ctaggttttg tctatcatct cagttcagag gcaacgaaac    3120
tggactcatt actccaaata acatggact tttacaaaac ccatatcgta taccaccact    3180 tttcccatc aagtcatttg ttaaaactaa atgtaagaaa atctgctag aggaaaactt    3240 tgaggaacat tcaatgtcac ctgaaagaga atgggaaat gagaacattc caagtacagt    3300
gagcacaatt agccgtaata acattagaga aaatgttttt aaagaagcca gctcaagcaa    3360
tattaatgaa gtaggttcca gtactaatga agtgggctcc agtattaatg aaataggttc    3420
cagtgatgaa acattcaag cagaactagg tagaaacaga gggccaaaat tgaatgctat     3480
gcttagatta ggggttttgc aacctgaggt ctataaacaa agtcttcctg gaagtaattg    3540
taagcatcct gaaataaaaa agcaagaata tgaagaagta gttcagactg ttaatacaga    3600
tttctctcca tatctgattt cagataactt agaacagcct atgggaagta gtcatgcatc    3660
tcaggtttgt tctgagacac ctgatgacct gttagatgat ggtgaaataa aggaagatac    3720
tagttttgct gaaatgaca ttaaggaaag ttctgctgtt tttagcaaaa gcgtccagaa    3780
aggagagctt agcaggagtc ctagcccttt cacccataca catttggctc agggttaccg    3840
aagaggggcc aagaaattag agtcctcaga agagaactta tctagtgagg atgaagagct    3900
tccctgcttc caacacttgt tatttggtaa agtaaacaat ataccttctc agtctactag    3960
gcatagcacc gttgctaccg agtgtctgtc taagaacaca gaggagaatt tattatcatt    4020
```

```
gaagaatagc ttaaatgact gcagtaacca ggtaatattg gcaaaggcat ctcaggaaca      4080
tcaccttagt gaggaaacaa aatgttctgc tagcttgttt tcttcacagt gcagtgaatt      4140
ggaagacttg actgcaaata caaacaccca ggatcctttc ttgattggtt cttccaaaca      4200
aatgaggcat cagtctgaaa gccagggagt tggtctgagt gacaaggaat tggtttcaga      4260
tgatgaagaa agaggaacgg gcttggaaga aaataatcaa gaagagcaaa gcatggattc      4320
aaacttaggt gaagcagcat ctgggtgtga gagtgaaaca agcgtctctg aagactgctc      4380
agggctatcc tctcagagtg acattttaac cactcagcag agggatacca tgcaacataa      4440
cctgataaag ctccagcagg aaatggctga actagaagct gtgttagaac agcatgggag      4500
ccagccttct aacagctacc cttccatcat aagtgactct tctgcccttg aggacctgcg      4560
aaatccagaa caaagcacat cagaaaaagc agtattaact tcacagaaaa gtagtgaata      4620
ccctataagc cagaatccag aaggcctttc tgctgacaag tttgaggtgt ctgcagatag      4680
ttctaccagt aaaaataaag aaccaggagt ggaaaggtca tcccttcta aatgcccatc       4740 attagatgat aggtggtaca tgcacagttg ctctgggagt cttcagaata gaaactaccc      4800
atctcaagag gagctcatta aggttgttga tgtggaggag caacagctgg aagagtctgg      4860
gccacacgat ttgacggaaa catcttactt gccaaggcaa gatctagagg gaacccctta      4920
cctggaatct ggaatcagcc tcttctctga tgaccctgaa tctgatcctt ctgaagacag      4980
agccccagag tcagctcgtg ttggcaacat accatcttca acctctgcat gaaagttcc       5040 ccaattgaaa gttgcagaat ctgcccagag tccagctgct gctcatacta ctgatactgc      5100
tgggtataat gcaatggaag aaagtgtgag cagggagaag ccagaattga cagcttcaac      5160
agaaagggtc aacaaaagaa tgtccatggt ggtgtctggc ctgaccccag aagaatttat      5220
gctcgtgtac aagtttgcca gaaaacacca catcacttta actaatctaa ttactgaaga      5280
gactactcat gttgttatga aaacagatgc tgagtttgtg tgtgaacgga cactgaaata      5340
ttttctagga attgcgggag gaaaatgggt agttagctat ttctgggtga cccagtctat      5400
taaagaaaga aaaatgctga atgagcatga ttttgaagtc agaggagatg tggtcaatgg      5460
aagaaaccac caaggtccaa agcgagcaag agaatcccag acagaaaga tcttcagggg       5520 gctagaaatc tgttgctatg ggcccttcac caacatgccc acagatcaac tggaatggat      5580
ggtacagctg tgtggtgctt ctgtggtgaa ggagctttca tcattcaccc ttggcacagg      5640
tgtccaccca attgtggttg tgcagccaga tgcctggaca gaggacaatg cttccatgc       5700 aattgggcag atgtgtgagg cacctgtggt gaccccgagag tgggtgttgg acagtgtagc      5760
actctaccag tgccaggagc tggacaccta cctgataccc cagatccccc acagccacta      5820
ctgactgcag ccagccacag gtacagagcc acaggacccc aagaatgagc ttacaaagtg      5880
gcctttccag gccctgggag ctcctctcac tcttcagtcc ttctactgtc ctggctacta      5940 aatatttat gtacatcagc ctgaaaagga cttctggcta tgcaagggtc ccttaaagat       6000
tttctgcttg aagtctccct tggaaatctg ccatgagcac aaaattatgg taatttttca      6060
cctgagaaga tttaaaaacc atttaaacgc caccaattga gcaagatgct gattcattat      6120
ttatcagccc tattctttct attcaggctg ttgttggctt agggctggaa gcacagagtg      6180
gcttggcctc aagagaatag ctggtttccc taagtttact tctctaaaac cctgtgttca      6240
caaaggcaga gagtcagacc cttcaatgga aggagagtgc ttgggatcga ttatgtgact      6300
taaagtcaga atagtccttg ggcagttctc aaatgttgga gtggaacatt ggggaggaaa      6360
ttctgaggca ggtattagaa atgaaaagga aacttgaaac ctgggcatgg tggctcacgc      6420
```

-continued

```
ctgtaatccc agcactttgg gaggccaagg tgggcagatc actggaggtc aggagttcga    6480
aaccagcctg gccaacatgg tgaaacccca tctctactaa aaatacagaa attagccggt    6540
catggtggtg gacacctgta atcccagcta ctcaggtggc taaggcagga gaatcacttc    6600
agcccgggag gtggaggttg cagtgagcca agatcatacc acggcactcc agcctgggtg    6660
acagtgagac tgtggctcaa aaaaaaaaaa aaaaaaagga aaatgaaact agaagagatt    6720
tctaaaagtc tgagatatat ttgctagatt tctaaagaat gtgttctaaa acagcagaag    6780
attttcaaga accggtttcc aaagacagtc ttctaattcc tcattagtaa taagtaaaat    6840
gtttattgtt gtagctctgg tatataatcc attcctctta aaatataaga cctctggcat    6900
gaatatttca tatctataaa atgacagatc ccaccaggaa ggaagctgtt gctttctttg    6960
aggtgatttt tttcctttgc tccctgttgc tgaaaccata cagcttcata aataattttg    7020
cttgctgaag gaagaaaaag tgttttttcat aaacccatta tccaggactg tttatagctg    7080
ttggaaggac taggtcttcc ctagcccccc cagtgtgcaa gggcagtgaa gacttgattg    7140
tacaaaatac gttttgtaaa tgttgtgctg ttaacactgc aaataaactt ggtagcaaac    7200
acttccaaaa aaaaaaaaaa aaaa                                           7224
```

<210> SEQ ID NO 2
<211> LENGTH: 1863
<212> TYPE: PRT
<213> ORGANISM: Homo sapiens

<400> SEQUENCE: 2

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220
```

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
            245                 250                 255

His Pro Glu Lys Tyr Gln Gly Ser Ser Val Ser Asn Leu His Val Glu
        260                 265                 270

Pro Cys Gly Thr Asn Thr His Ala Ser Ser Leu Gln His Glu Asn Ser
    275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn

```
            645                 650                 655
Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
            995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065
```

```
Gln Ala Glu Leu Gly Arg Asn Arg Gly Pro Lys Leu Asn Ala Met
    1070            1075            1080

Leu Arg Leu Gly Val Leu Gln Pro Glu Val Tyr Lys Gln Ser Leu
    1085            1090            1095

Pro Gly Ser Asn Cys Lys His Pro Glu Ile Lys Lys Gln Glu Tyr
    1100            1105            1110

Glu Glu Val Val Gln Thr Val Asn Thr Asp Phe Ser Pro Tyr Leu
    1115            1120            1125

Ile Ser Asp Asn Leu Glu Gln Pro Met Gly Ser Ser His Ala Ser
    1130            1135            1140

Gln Val Cys Ser Glu Thr Pro Asp Asp Leu Leu Asp Asp Gly Glu
    1145            1150            1155

Ile Lys Glu Asp Thr Ser Phe Ala Glu Asn Asp Ile Lys Glu Ser
    1160            1165            1170

Ser Ala Val Phe Ser Lys Ser Val Gln Lys Gly Glu Leu Ser Arg
    1175            1180            1185

Ser Pro Ser Pro Phe Thr His Thr His Leu Ala Gln Gly Tyr Arg
    1190            1195            1200

Arg Gly Ala Lys Lys Leu Glu Ser Ser Glu Glu Asn Leu Ser Ser
    1205            1210            1215

Glu Asp Glu Glu Leu Pro Cys Phe Gln His Leu Leu Phe Gly Lys
    1220            1225            1230

Val Asn Asn Ile Pro Ser Gln Ser Thr Arg His Ser Thr Val Ala
    1235            1240            1245

Thr Glu Cys Leu Ser Lys Asn Thr Glu Glu Asn Leu Leu Ser Leu
    1250            1255            1260

Lys Asn Ser Leu Asn Asp Cys Ser Asn Gln Val Ile Leu Ala Lys
    1265            1270            1275

Ala Ser Gln Glu His His Leu Ser Glu Glu Thr Lys Cys Ser Ala
    1280            1285            1290

Ser Leu Phe Ser Ser Gln Cys Ser Glu Leu Glu Asp Leu Thr Ala
    1295            1300            1305

Asn Thr Asn Thr Gln Asp Pro Phe Leu Ile Gly Ser Ser Lys Gln
    1310            1315            1320

Met Arg His Gln Ser Glu Ser Gln Gly Val Gly Leu Ser Asp Lys
    1325            1330            1335

Glu Leu Val Ser Asp Asp Glu Glu Arg Gly Thr Gly Leu Glu Glu
    1340            1345            1350

Asn Asn Gln Glu Glu Gln Ser Met Asp Ser Asn Leu Gly Glu Ala
    1355            1360            1365

Ala Ser Gly Cys Glu Ser Glu Thr Ser Val Ser Glu Asp Cys Ser
    1370            1375            1380

Gly Leu Ser Ser Gln Ser Asp Ile Leu Thr Thr Gln Gln Arg Asp
    1385            1390            1395

Thr Met Gln His Asn Leu Ile Lys Leu Gln Gln Glu Met Ala Glu
    1400            1405            1410

Leu Glu Ala Val Leu Glu Gln His Gly Ser Gln Pro Ser Asn Ser
    1415            1420            1425

Tyr Pro Ser Ile Ile Ser Asp Ser Ser Ala Leu Glu Asp Leu Arg
    1430            1435            1440

Asn Pro Glu Gln Ser Thr Ser Glu Lys Ala Val Leu Thr Ser Gln
    1445            1450            1455
```

```
Lys Ser Ser Glu Tyr Pro Ile Ser Gln Asn Pro Glu Gly Leu Ser
1460                1465                1470

Ala Asp Lys Phe Glu Val Ser Ala Asp Ser Ser Thr Ser Lys Asn
1475                1480                1485

Lys Glu Pro Gly Val Glu Arg Ser Ser Pro Ser Lys Cys Pro Ser
1490                1495                1500

Leu Asp Asp Arg Trp Tyr Met His Ser Cys Ser Gly Ser Leu Gln
1505                1510                1515

Asn Arg Asn Tyr Pro Ser Gln Glu Glu Leu Ile Lys Val Val Asp
1520                1525                1530

Val Glu Glu Gln Gln Leu Glu Glu Ser Gly Pro His Asp Leu Thr
1535                1540                1545

Glu Thr Ser Tyr Leu Pro Arg Gln Asp Leu Glu Gly Thr Pro Tyr
1550                1555                1560

Leu Glu Ser Gly Ile Ser Leu Phe Ser Asp Asp Pro Glu Ser Asp
1565                1570                1575

Pro Ser Glu Asp Arg Ala Pro Glu Ser Ala Arg Val Gly Asn Ile
1580                1585                1590

Pro Ser Ser Thr Ser Ala Leu Lys Val Pro Gln Leu Lys Val Ala
1595                1600                1605

Glu Ser Ala Gln Ser Pro Ala Ala Ala His Thr Thr Asp Thr Ala
1610                1615                1620

Gly Tyr Asn Ala Met Glu Glu Ser Val Ser Arg Glu Lys Pro Glu
1625                1630                1635

Leu Thr Ala Ser Thr Glu Arg Val Asn Lys Arg Met Ser Met Val
1640                1645                1650

Val Ser Gly Leu Thr Pro Glu Glu Phe Met Leu Val Tyr Lys Phe
1655                1660                1665

Ala Arg Lys His His Ile Thr Leu Thr Asn Leu Ile Thr Glu Glu
1670                1675                1680

Thr Thr His Val Val Met Lys Thr Asp Ala Glu Phe Val Cys Glu
1685                1690                1695

Arg Thr Leu Lys Tyr Phe Leu Gly Ile Ala Gly Gly Lys Trp Val
1700                1705                1710

Val Ser Tyr Phe Trp Val Thr Gln Ser Ile Lys Glu Arg Lys Met
1715                1720                1725

Leu Asn Glu His Asp Phe Glu Val Arg Gly Asp Val Val Asn Gly
1730                1735                1740

Arg Asn His Gln Gly Pro Lys Arg Ala Arg Glu Ser Gln Asp Arg
1745                1750                1755

Lys Ile Phe Arg Gly Leu Glu Ile Cys Cys Tyr Gly Pro Phe Thr
1760                1765                1770

Asn Met Pro Thr Asp Gln Leu Glu Trp Met Val Gln Leu Cys Gly
1775                1780                1785

Ala Ser Val Val Lys Glu Leu Ser Ser Phe Thr Leu Gly Thr Gly
1790                1795                1800

Val His Pro Ile Val Val Gln Pro Asp Ala Trp Thr Glu Asp
1805                1810                1815

Asn Gly Phe His Ala Ile Gly Gln Met Cys Glu Ala Pro Val Val
1820                1825                1830

Thr Arg Glu Trp Val Leu Asp Ser Val Ala Leu Tyr Gln Cys Gln
1835                1840                1845

Glu Leu Asp Thr Tyr Leu Ile Pro Gln Ile Pro His Ser His Tyr
```

<210> SEQ ID NO 3
<211> LENGTH: 2451
<212> TYPE: DNA
<213> ORGANISM: Homo sapiens

<400> SEQUENCE: 3

| | | | | | |
|---|---|---|---|---|---|
| tgggcctggt | tgtggaggcc | ccttttgcaa | aacctcagtc | tgaatttagt | agacagaagt | 60 |
| cactaggaat | gccttgacag | gatcctgcct | tagctaaggc | tccctccagc | tgcagagggt | 120 |
| gtttttgtta | gactcacaca | ctgcgtgaaa | ctgctcagaa | tagagccatg | atctcaacca | 180 |
| cgaaatggga | acttagattt | tggagaaact | aacggggacg | gacttctttc | ctagcctgag | 240 |
| tgttgagcag | tgtcatgcct | tggcgtttca | gctcctcgtt | gtctaggtgg | tgaaatgaca | 300 |
| gaactcattc | gcttctttga | ttggtgattt | tgaaataatc | tttcatcaag | ttccatctcc | 360 |
| tttaccctca | tatggaatat | atctctctgt | ctgttgttaa | actacgatga | catgtctgta | 420 |
| gctatcagaa | agagaagctg | ggaagaacat | gtgacccact | ggatgggaca | gccttttaat | 480 |
| tctgatgatc | gtaacacagc | atgtcatcat | ggactagtag | ctgacagctt | gcaggcaagt | 540 |
| atggaaaaag | atgcaactct | aaatgtggac | cgcaaagaga | agtgtgtttc | actacctgac | 600 |
| tgctgtcatg | gatcagagct | gagagatttt | cctgggaggc | caatgggtca | tctttcaaag | 660 |
| gatgtggacg | aaaatgacag | ccatgaaggt | gaagatcagt | ttcttctct | ggaagccagc | 720 |
| acagaaacac | tagtgcatgt | ttctgatgag | gataacaatg | ctgatttatg | ccttacagat | 780 |
| gataaacagg | ttttaaatac | ccaagggcag | aaaacatcag | ccaacatat | gatccaagga | 840 |
| gcaggctcct | tagaaaaggc | actgcccatc | atacaaagta | accaagtttc | ttctaactcc | 900 |
| tggggaatag | ctggtgaaac | tgaattagca | ctggtaaaag | aaagtgggga | gagaaaagtt | 960 |
| actgactcta | taagtaaaag | cctggagctt | tgcaatgaaa | taagcttaag | tgaaataaaa | 1020 |
| gatgcaccca | agtaaatgc | agtggatact | ttgaacgtga | aagatattgc | acctgagaaa | 1080 |
| caattgctta | actctgctgt | aattgctcag | caacgaagga | aacctgaccc | ccctaaagat | 1140 |
| gaaaatgaaa | gaagcacctg | caatgtagta | caagatgagt | tcttggatac | tccttgcaca | 1200 |
| aacagaggac | tgccattatt | aaaaacagat | tttggaagct | gccttctgca | gcctccttcc | 1260 |
| tgccccaatg | gaatgtcagc | tgaaaatggc | ctggagaaga | gtggttttc | acaacatcaa | 1320 |
| aacaaaagtc | caccaaaggt | caaggcagaa | gatggcatgc | agtgtttaca | attaaaggag | 1380 |
| accctggcca | cccaggaacc | cacagataac | caagtcagac | ttcgtaagag | aaaggaaata | 1440 |
| agagaagatc | gagatagggc | gcggctggac | tccatggtgc | tgctgattat | gaaactggac | 1500 |
| cagcttgatc | aggacataga | aaatgccctc | agcaccagct | cctctccatc | aggcacacca | 1560 |
| acaaacctgc | ggcggcacgt | tcctgatctg | gaatcaggat | ctgaaagtgg | agcagatacc | 1620 |
| atttcagtaa | atcagacacg | agtaaatttg | tcttctgaca | ctgagtccac | ggacctccca | 1680 |
| tcttccactc | cagtagccaa | ttctggaacc | aaacccaaga | ctacggctat | tcaaggtatt | 1740 |
| tcagagaagg | aaaaggctgg | taagttgaca | ttttggttct | gttttctcgc | caatctattt | 1800 |
| tagaataaat | ttcaccttaa | aataggcatt | ttattaaata | tataaaatgt | atacatctca | 1860 |
| tgaatatatg | ggaaaatgtt | gtttaaattc | tgtaaaagaa | atttgttttg | ctcaatatgt | 1920 |
| aagaaaaata | tacgtggttt | tctgactaaa | tgacattgtg | ttagaataag | atatgtgttt | 1980 |
| cttgggtct | tccttgtaac | tgcaaccaca | atttttttt | cttaagcaaa | agaattaaat | 2040 |
| gttgatcaag | gttctgggga | atgaatttgg | aaattagttg | ttaataatta | ccaaggttta | 2100 |

-continued

```
tttttactct taatgactta gtagccacag aaaaagatgt aattgatgct taaagctgat      2160
gccatactat caaaaatata gtgatgaagc aatgtgaata attgtattga agaaaaaat       2220 tatagtattt ttctgtgttc tgtgctttaa ttataattat ttaacagtat tatgggaaat      2280
ggacaaggac tgatgagaaa tgaaaatatg aaaaattaga catggattgg tagatctatg      2340 tgttttaaa aaatcatact atcttatgtg ttctgtgtaa taaaaacgaa aacagattaa       2400
aggtatatta tctaacttga aaaaaaaaaa aaaaaaaaa aaaaaaaaa a                 2451
```

<210> SEQ ID NO 4
<211> LENGTH: 463
<212> TYPE: PRT
<213> ORGANISM: Homo sapiens

<400> SEQUENCE: 4

```
Met Ser Val Ala Ile Arg Lys Arg Ser Trp Glu Glu His Val Thr His
1               5                   10                  15

Trp Met Gly Gln Pro Phe Asn Ser Asp Asp Arg Asn Thr Ala Cys His
            20                  25                  30

His Gly Leu Val Ala Asp Ser Leu Gln Ala Ser Met Glu Lys Asp Ala
        35                  40                  45

Thr Leu Asn Val Asp Arg Lys Glu Lys Cys Val Ser Leu Pro Asp Cys
    50                  55                  60

Cys His Gly Ser Glu Leu Arg Asp Phe Pro Gly Arg Pro Met Gly His
65                  70                  75                  80

Leu Ser Lys Asp Val Asp Glu Asn Asp Ser His Glu Gly Glu Asp Gln
                85                  90                  95

Phe Leu Ser Leu Glu Ala Ser Thr Glu Thr Leu Val His Val Ser Asp
            100                 105                 110

Glu Asp Asn Asn Ala Asp Leu Cys Leu Thr Asp Asp Lys Gln Val Leu
        115                 120                 125

Asn Thr Gln Gly Gln Lys Thr Ser Gly Gln His Met Ile Gln Gly Ala
    130                 135                 140

Gly Ser Leu Glu Lys Ala Leu Pro Ile Ile Gln Ser Asn Gln Val Ser
145                 150                 155                 160

Ser Asn Ser Trp Gly Ile Ala Gly Glu Thr Glu Leu Ala Leu Val Lys
                165                 170                 175

Glu Ser Gly Glu Arg Lys Val Thr Asp Ser Ile Ser Lys Ser Leu Glu
            180                 185                 190

Leu Cys Asn Glu Ile Ser Leu Ser Glu Ile Lys Asp Ala Pro Lys Val
        195                 200                 205

Asn Ala Val Asp Thr Leu Asn Val Lys Asp Ile Ala Pro Glu Lys Gln
    210                 215                 220

Leu Leu Asn Ser Ala Val Ile Ala Gln Gln Arg Arg Lys Pro Asp Pro
225                 230                 235                 240

Pro Lys Asp Glu Asn Glu Arg Ser Thr Cys Asn Val Val Gln Asp Glu
                245                 250                 255

Phe Leu Asp Thr Pro Cys Thr Asn Arg Gly Leu Pro Leu Leu Lys Thr
            260                 265                 270

Asp Phe Gly Ser Cys Leu Leu Gln Pro Pro Ser Cys Pro Asn Gly Met
        275                 280                 285

Ser Ala Glu Asn Gly Leu Glu Lys Ser Gly Phe Ser Gln His Gln Asn
    290                 295                 300

Lys Ser Pro Pro Lys Val Lys Ala Glu Asp Gly Met Gln Cys Leu Gln
```

```
                305                 310                 315                 320
Leu Lys Glu Thr Leu Ala Thr Gln Glu Pro Thr Asp Asn Gln Val Arg
                    325                 330                 335

Leu Arg Lys Arg Lys Glu Ile Arg Glu Asp Arg Asp Arg Ala Arg Leu
                    340                 345                 350

Asp Ser Met Val Leu Leu Ile Met Lys Leu Asp Gln Leu Asp Gln Asp
                    355                 360                 365

Ile Glu Asn Ala Leu Ser Thr Ser Ser Pro Ser Gly Thr Pro Thr
    370                 375                 380

Asn Leu Arg Arg His Val Pro Asp Leu Glu Ser Gly Ser Glu Ser Gly
385                 390                 395                 400

Ala Asp Thr Ile Ser Val Asn Gln Thr Arg Val Asn Leu Ser Ser Asp
                    405                 410                 415

Thr Glu Ser Thr Asp Leu Pro Ser Ser Thr Pro Val Ala Asn Ser Gly
                    420                 425                 430

Thr Lys Pro Lys Thr Thr Ala Ile Gln Gly Ile Ser Glu Lys Glu Lys
                    435                 440                 445

Ala Gly Lys Leu Thr Phe Trp Phe Cys Phe Leu Ala Asn Leu Phe
    450                 455                 460
```

<210> SEQ ID NO 5
<211> LENGTH: 4082
<212> TYPE: DNA
<213> ORGANISM: Homo sapiens

<400> SEQUENCE: 5

| | | | | | |
|---|---|---|---|---|---|
| gcgcgcgccg | gcctgggcag | gcgagcgggc | gcgctcccgc | ccctctccc | ctccccgcgc | 60 |
| gcccgagcgc | gcctccgccc | ttgcccgccc | cctgacgctg | cctcagctcc | tcagtgcaca | 120 |
| gtgctgcctc | gtctgagggg | acaggaggat | caccctcttc | gtcgcttcgg | ccagtgtgtc | 180 |
| gggctgggcc | ctgacaagcc | acctgaggag | aggctcggag | ccgggcccgg | accccggcga | 240 |
| ttgccgcccg | cttctctcta | gtctcacgag | gggtttcccg | cctcgcaccc | ccacctctgg | 300 |
| acttgccttt | ccttctcttc | tccgcgtgtg | gagggagcca | gcgcttaggc | cggagcgagc | 360 |
| ctgggggccg | cccgccgtga | agacatcgcg | gggaccgatt | caccatggag | ggcgccggcg | 420 |
| gcgcgaacga | caagaaaaag | ataagttctg | aacgtcgaaa | agaaaagtct | cgagatgcag | 480 |
| ccagatctcg | gcgaagtaaa | gaatctgaag | tttttttatga | gcttgctcat | cagttgccac | 540 |
| ttccacataa | tgtgagttcg | catcttgata | aggcctctgt | gatgaggctt | accatcagct | 600 |
| atttgcgtgt | gaggaaactt | ctggatgctg | gtgatttgga | tattgaagat | gacatgaaag | 660 |
| cacagatgaa | ttgctttat | ttgaaagcct | tggatggttt | tgttatggtt | ctcacagatg | 720 |
| atggtgacat | gatttacatt | tctgataatg | tgaacaaata | catgggatta | actcagtttg | 780 |
| aactaactgg | acacagtgtg | tttgatttta | ctcatccatg | tgaccatgag | gaaatgagag | 840 |
| aaatgcttac | acacagaaat | ggccttgtga | aaaagggtaa | agaacaaaac | acacagcgaa | 900 |
| gcttttttct | cagaatgaag | tgtaccctaa | ctagccgagg | aagaactatg | aacataaagt | 960 |
| ctgcaacatg | gaaggtattg | cactgcacag | gccacattca | cgtatatgat | accaacagta | 1020 |
| accaacctca | gtgtgggtat | aagaaaccac | ctatgacctg | cttggtgctg | atttgtgaac | 1080 |
| ccattcctca | cccatcaaat | attgaaattc | ctttagatag | caagactttc | ctcagtcgac | 1140 |
| acagcctgga | tatgaaattt | tcttattgtg | atgaaagaat | taccgaattg | atgggatatg | 1200 |
| agccagaaga | actttaggc | cgctcaattt | atgaatatta | tcatgctttg | gactctgatc | 1260 |

```
atctgaccaa aactcatcat gatatgttta ctaaaggaca agtcaccaca ggacagtaca   1320
ggatgcttgc caaaagaggt ggatatgtct gggttgaaac tcaagcaact gtcatatata   1380
acaccaagaa ttctcaacca cagtgcattg tatgtgtgaa ttacgttgtg agtggtatta   1440
ttcagcacga cttgattttc tcccttcaac aaacagaatg tgtccttaaa ccggttgaat   1500
cttcagatat gaaatgact cagctattca ccaaagttga atcagaagat acaagtagcc   1560
tctttgacaa acttaagaag gaacctgatg ctttaacttt gctggcccca gccgctggag   1620
acacaatcat atctttagat tttggcagca acgacacaga aactgatgac cagcaacttg   1680
aggaagtacc attatataat gatgtaatgc tcccctcacc caacgaaaaa ttacagaata   1740
taaatttggc aatgtctcca ttacccaccg ctgaaacgcc aaagccactt cgaagtagtg   1800
ctgaccctgc actcaatcaa gaagttgcat taaaattaga accaaatcca gagtcactgg   1860
aactttcttt taccatgccc cagattcagg atcagacacc tagtccttcc gatggaagca   1920
ctagacaaag ttcacctgag cctaatagtc ccagtgaata ttgttttat gtggatagtg   1980 atatggtcaa tgaattcaag ttggaattgg tagaaaaact ttttgctgaa gacacagaag   2040
caaagaaccc attttctact caggacacag atttagactt ggagatgtta gctccctata   2100
tcccaatgga tgatgacttc cagttacgtt ccttcgatca gttgtcacca ttagaaagca   2160
gttccgcaag ccctgaaagc gcaagtcctc aaagcacagt tacagtattc cagcagactc   2220
aaatacaaga acctactgct aatgccacca ctaccactgc caccactgat gaattaaaaa   2280
cagtgacaaa agaccgtatg gaagacatta aatattgat tgcatctcca tctcctaccc   2340
acatacataa agaaactact agtgccacat catcaccata tagagatact caaagtcgga   2400
cagcctcacc aaacagagca ggaaaaggag tcatagaaca gacagaaaaa tctcatccaa   2460
gaagccctaa cgtgttatct gtcgctttga gtcaaagaac tacagttcct gaggaagaac   2520
taaatccaaa gatactagct ttgcagaatg ctcagagaaa gcgaaaaatg gaacatgatg   2580
gttcactttt tcaagcagta ggaattggaa cattattaca gcagccagac gatcatgcag   2640
ctactacatc actttcttgg aaacgtgtaa aaggatgcaa atctagtgaa cagaatggaa   2700
tggagcaaaa gacaattatt ttaataccct ctgatttagc atgtagactg ctggggcaat   2760
caatggatga agtggatta ccacagctga ccagttatga ttgtgaagtt aatgctccta   2820
tacaaggcag cagaaaccta ctgcagggtg aagaattact cagagctttg gatcaagtta   2880
actgagcttt ttcttaattt cattccttt tttggacact ggtggctcat tacctaaagc   2940
agtctattta tattttctac atctaatttt agaagcctgg ctacaatact gcacaaactt   3000
ggttagttca attttgatcc cctttctact taatttacat taatgctctt ttttagtatg   3060
ttctttaatg ctggatcaca gacagctcat tttctcagtt ttttggtatt taaaccattg   3120
cattgcagta gcatcatttt aaaaaatgca ccttttatt tatttatttt tggctaggga   3180
gtttatccct ttttcgaatt atttttaaga agatgccaat ataattttg taagaaggca   3240 gtaacctttc atcatgatca taggcagttg aaaaattttt acaccttttt tttcacattt   3300
tacataaata ataatgcttt gccagcagta cgtggtagcc acaattgcac aatatatttt   3360
cttaaaaaat accagcagtt actcatggaa tatattctgc gttataaaa ctagttttta   3420 agaagaaatt ttttttggcc tatgaaattg ttaaacctgg aacatgacat tgttaatcat   3480
ataataatga ttcttaaatg ctgtatggtt tattatttaa atgggtaaag ccatttacat   3540
aatatagaaa gatatgcata tatctagaag gtatgtggca tttatttgga taaaattctc   3600
aattcagaga aatcatctga tgtttctata gtcacttgc cagctcaaaa gaaaacaata   3660
```

| | |
|---|---|
| ccctatgtag ttgtggaagt ttatgctaat attgtgtaac tgatattaaa cctaaatgtt | 3720 |
| ctgcctaccc tgttggtata aagatatttt gagcagactg taaacaagaa aaaaaaaatc | 3780 |
| atgcattctt agcaaaattg cctagtatgt taatttgctc aaaatacaat gtttgatttt | 3840 |
| atgcactttg tcgctattaa catccttttt ttcatgtaga tttcaataat tgagtaattt | 3900 |
| tagaagcatt attttaggaa tatatagttg tcacagtaaa tatcttgttt tttctatgta | 3960 |
| cattgtacaa attttcatt cctttgctc tttgtggttg gatctaacac taactgtatt | 4020 |
| gttttgttac atcaaataaa catcttctgt ggaccaggca aaaaaaaaaa aaaaaaaaa | 4080 |
| aa | 4082 |

<210> SEQ ID NO 6
<211> LENGTH: 3955
<212> TYPE: DNA
<213> ORGANISM: Homo sapiens

<400> SEQUENCE: 6

| | |
|---|---|
| gcgcgcgccg gcctgggcag gcgagcgggc gcgctcccgc cccctctccc ctcccgcgc | 60 |
| gcccgagcgc gcctccgccc ttgcccgccc cctgacgctg cctcagctcc tcagtgcaca | 120 |
| gtgctgcctc gtctgagggg acaggaggat caccctcttc gtcgcttcgg ccagtgtgtc | 180 |
| gggctgggcc ctgacaagcc acctgaggag aggctcggag ccgggcccgg accccggcga | 240 |
| ttgccgcccg cttctctcta gtctcacgag gggtttcccg cctcgcaccc ccacctctgg | 300 |
| acttgccttt ccttctcttc tccgcgtgtg gagggagcca gcgcttaggc cggagcgagc | 360 |
| ctgggggccg cccgccgtga agacatcgcg gggaccgatt caccatggag ggcgccggcg | 420 |
| gcgcgaacga caagaaaaag ataagttctg aacgtcgaaa agaaaagtct cgagatgcag | 480 |
| ccagatctcg gcgaagtaaa gaatctgaag tttttttatga gcttgctcat cagttgccac | 540 |
| ttccacataa tgtgagttcg catcttgata aggcctctgt gatgaggctt accatcagct | 600 |
| atttgcgtgt gaggaaactt ctggatgctg gtgatttgga tattgaagat gacatgaaag | 660 |
| cacagatgaa ttgcttttat ttgaaagcct tggatggttt tgttatggtt ctcacagatg | 720 |
| atggtgacat gatttacatt tctgataatg tgaacaaata catgggatta actcagtttg | 780 |
| aactaactgg acacagtgtg tttgatttta ctcatccatg tgaccatgag gaaatgagag | 840 |
| aaatgcttac acacagaaat ggccttgtga aaagggtaa agaacaaaac acacagcgaa | 900 |
| gctttttct cagaatgaag tgtaccctaa ctagccgagg aagaactatg aacataaagt | 960 |
| ctgcaacatg gaaggtattg cactgcacag gccacattca cgtatatgat accaacagta | 1020 |
| accaacctca gtgtgggtat aagaaaccac ctatgacctg cttggtgctg atttgtgaac | 1080 |
| ccattcctca cccatcaaat attgaaattc ctttagatag caagactttc tcagtcgac | 1140 |
| acagcctgga tatgaaattt tcttattgtg atgaaagaat taccgaattg atgggatatg | 1200 |
| agccagaaga acttttaggc cgctcaattt atgaatatta tcatgctttg gactctgatc | 1260 |
| atctgaccaa aactcatcat gatatgttta ctaaaggaca agtcaccaca ggacagtaca | 1320 |
| ggatgcttgc caaagaggt ggatatgtct gggttgaaac tcaagcaact gtcatatata | 1380 |
| acaccaagaa ttctcaacca cagtgcattg tatgtgtgaa ttacgttgtg agtggtatta | 1440 |
| ttcagcacga cttgattttc tcccttcaac aaacagaatg tgtccttaaa ccggttgaat | 1500 |
| cttcagatat gaaatgact cagctattca ccaaagttga atcagaagat acaagtagcc | 1560 |
| tctttgacaa acttaagaag gaacctgatg cttttaacttt gctggcccca gccgctggag | 1620 |

```
acacaatcat atctttagat tttggcagca acgacacaga aactgatgac cagcaacttg   1680
aggaagtacc attatataat gatgtaatgc tcccctcacc caacgaaaaa ttacagaata   1740
taaatttggc aatgtctcca ttacccaccg ctgaaacgcc aaagccactt cgaagtagtg   1800
ctgaccctgc actcaatcaa gaagttgcat taaaattaga accaaatcca gagtcactgg   1860
aactttcttt taccatgccc cagattcagg atcagacacc tagtccttcc gatggaagca   1920
ctagacaaag ttcacctgag cctaatagtc ccagtgaata ttgttttat gtggatagtg     1980
atatggtcaa tgaattcaag ttggaattgg tagaaaaact ttttgctgaa gacacagaag   2040
caaagaaccc attttctact caggacacag atttagactt ggagatgtta gctccctata   2100
tcccaatgga tgatgacttc cagttacgtt ccttcgatca gttgtcacca ttagaaagca   2160
gttccgcaag ccctgaaagc gcaagtcctc aaagcacagt tacagtattc cagcagactc   2220
aaatacaaga acctactgct aatgccacca ctaccactgc caccactgat gaattaaaaa   2280
cagtgacaaa agaccgtatg gaagacatta aaatattgat tgcatctcca tctcctaccc   2340
acatacataa agaaactact agtgccacat catcaccata tagagatact caaagtcgga   2400
cagcctcacc aaaacagagca ggaaaaggag tcatagaaca gacagaaaaa tctcatccaa   2460
gaagccctaa cgtgttatct gtcgctttga gtcaaagaac tacagttcct gaggaagaac   2520
taaatccaaa gatactagct ttgcagaatg ctcagagaaa gcgaaaaatg aacatgatg    2580
gttcactttt tcaagcagta ggaattattt agcatgtaga ctgctggggc aatcaatgga   2640
tgaaagtgga ttaccacagc tgaccagtta tgattgtgaa gttaatgctc ctatacaagg   2700
cagcagaaac ctactgcagg gtgaagaatt actcagagct ttggatcaag ttaactgagc   2760
ttttcttaa tttcattcct ttttttggac actggtggct cattacctaa agcagtctat    2820
ttatattttc tacatctaat tttagaagcc tggctacaat actgcacaaa cttggttagt   2880
tcaattttga tcccctttct acttaattta cattaatgct cttttttagt atgttcttta   2940
atgctggatc acagacagct cattttctca gttttttggt atttaaacca ttgcattgca   3000
gtagcatcat tttaaaaaat gcacctttt attttattat ttttggctag ggagtttatc    3060
cctttttcga attattttta agaagatgcc aatataattt ttgtaagaag gcagtaacct   3120
ttcatcatga tcataggcag ttgaaaaatt tttacacctt ttttttcaca ttttacataa   3180
ataataatgc tttgccagca gtacgtggta gccacaattg cacaatatat tttcttaaaa   3240
aataccagca gttactcatg gaatatattc tgcgtttata aaactagttt ttaagaagaa   3300
attttttttg gcctatgaaa ttgttaaacc tggaacatga cattgttaat catataataa   3360
tgattcttaa atgctgtatg gtttattatt taaatgggta aagccattta cataatatag   3420
aaagatatgc atatatctag aaggtatgtg gcatttattt ggataaaatt ctcaattcag   3480
agaaatcatc tgatgtttct atagtcactt tgccagctca aaagaaaaca atacccctatg  3540
tagttgtgga agtttatgct aatattgtgt aactgatatt aaacctaaat gttctgccta   3600
ccctgttggt ataagagatat tttgagcaga ctgtaaacaa gaaaaaaaaa atcatgcatt   3660
cttagcaaaa ttgcctagta tgttaatttg ctcaaaatac aatgtttgat tttatgcact   3720
ttgtcgctat taacatcctt tttttcatgt agatttcaat aattgagtaa ttttagaagc   3780
attattttag gaatatatag ttgtcacagt aaatatcttg tttttctat gtacattgta    3840
caaattttc attcctttg ctctttgtgg ttggatctaa cactaactgt attgttttgt      3900
tacatcaaat aaacatcttc tgtggaccag gcaaaaaaaa aaaaaaaaaa aaaaa         3955
```

```
<210> SEQ ID NO 7
<211> LENGTH: 3979
<212> TYPE: DNA
<213> ORGANISM: Homo sapiens

<400> SEQUENCE: 7
atttgaaaac ttggcaacct tggattggat ggattcatat ttcttagtat agaagttctt      60
gatataactg aaaaattaag ttaaacactt aataagtggt ggttactcag cacttttaga     120
tgctgtttat aatagatgac cttttctaac taatttacag ttttttgaaa gataactgag     180
aggttgaggg acggagattt tcttcaagca attttttttt tcattttaaa tgagctccca     240
atgtcggagt ttgaaaaaca aatttgtctt tttaaaagaa ggtctaggaa actcaaaacc     300
tgaagaattg aagaaatca gaatagaaaa tggtaggata agttctgaac gtcgaaaaga     360
aaagtctcga gatgcagcca gatctcggcg aagtaaagaa tctgaagttt tttatgagct     420
tgctcatcag ttgccacttc cacataatgt gagttcgcat cttgataagg cctctgtgat     480
gaggcttacc atcagctatt tgcgtgtgag gaaacttctg gatgctggtg atttggatat     540
tgaagatgac atgaaagcac agatgaattg cttttatttg aaagccttgg atggttttgt     600
tatggttctc acagatgatg gtgacatgat ttacattct gataatgtga acaaatacat     660
gggattaact cagtttgaac taactggaca cagtgtgttt gattttactc atccatgtga     720
ccatgaggaa atgagagaaa tgcttacaca cagaaatggc cttgtgaaaa agggtaaaga     780
acaaaacaca cagcgaagct tttttctcag aatgaagtgt accctaacta gccgaggaag     840
aactatgaac ataaagtctg caacatggaa ggtattgcac tgcacaggcc acattcacgt     900
atatgatacc aacagtaacc aacctcagtg tgggtataag aaaccaccta tgacctgctt     960
ggtgctgatt tgtgaaccca ttcctcaccc atcaaatatt gaaattcctt tagatagcaa    1020
gactttcctc agtcgacaca gcctggatat gaaattttct tattgtgatg aaagaattac    1080
cgaattgatg ggatatgagc cagaagaact tttaggccgc tcaatttatg aatattatca    1140
tgctttggac tctgatcatc tgaccaaaac tcatcatgat atgtttacta aggacaagt    1200 caccacagga cagtacagga tgcttgccaa aagaggtgga tatgtctggg ttgaaactca    1260
agcaactgtc atatataaca ccaagaattc tcaaccacag tgcattgtat gtgtgaatta    1320
cgttgtgagt ggtattattc agcacgactt gattttctcc cttcaacaaa cagaatgtgt    1380
ccttaaaccg gttaatcttt cagatatgaa atgactcag ctattcacca agttgaatc      1440 agaagataca agtagcctct ttgacaaact taagaaggaa cctgatgctt taactttgct    1500
ggccccagcc gctggagaca caatcatatc tttagatttt ggcagcaacg acacagaaac    1560
tgatgaccag caacttgagg aagtaccatt ataatgat gtaatgctcc cctcacccaa       1620
cgaaaaatta cagaatataa atttggcaat gtctccatta cccaccgctg aaacgccaaa    1680
gccacttcga agtagtgctg accctgcact caatcaagaa gttgcattaa aattagaacc    1740
aaatccagag tcactggaac tttcttttac catgccccag attcaggatc agacacctag    1800
tccttccgat ggaagcacta gacaaagttc acctgagcct aatagtccca gtgaatattg    1860 ttttttatgtg gatagtgata tggtcaatga attcaagttg gaattggtag aaaaactttt    1920
tgctgaagac acagaagcaa agaacccatt ttctactcag gacacagatt tagacttgga    1980
gatgttagct ccctatatcc caatggatga tgacttccag ttacgttcct tcgatcagtt    2040
gtcaccatta gaaagcagtt ccgcaagccc tgaaagcgca agtcctcaaa gcacagttac    2100
agtattccag cagactcaaa tacaagaacc tactgctaat gccaccacta ccactgccac    2160
```

```
cactgatgaa ttaaaaacag tgacaaaaga ccgtatggaa gacattaaaa tattgattgc    2220
atctccatct cctacccaca tacataaaga aactactagt gccacatcat caccatatag    2280
agatactcaa agtcggacag cctcaccaaa cagagcagga aaaggagtca tagaacagac    2340
agaaaaatct catccaagaa gccctaacgt gttatctgtc gctttgagtc aaagaactac    2400
agttcctgag gaagaactaa atccaaagat actagctttg cagaatgctc agagaaagcg    2460
aaaaatggaa catgatggtt cacttttca agcagtagga attggaacat tattacagca    2520
gccagacgat catgcagcta ctacatcact ttcttggaaa cgtgtaaaag gatgcaaatc    2580
tagtgaacag aatggaatgg agcaaaagac aattatttta ataccctctg atttagcatg    2640
tagactgctg gggcaatcaa tggatgaaag tggattacca cagctgacca gttatgattg    2700
tgaagttaat gctcctatac aaggcagcag aaacctactg cagggtgaag aattactcag    2760
agctttggat caagttaact gagcttttc ttaatttcat tcctttttt ggacactggt    2820 ggctcattac ctaaagcagt ctatttatat tttctacatc taattttaga agcctggcta    2880
caatactgca caaacttggt tagttcaatt ttgatcccct ttctacttaa tttacattaa    2940
tgctcttttt tagtatgttc tttaatgctg gatcacagac agctcatttt ctcagttttt    3000
tggtatttaa accattgcat tgcagtagca tcattttaaa aaatgcacct tttatttat    3060 ttattttgg ctagggagtt tatccctttt tcgaattatt tttaagaaga tgccaatata    3120 attttgtaa gaaggcagta acctttcatc atgatcatag gcagttgaaa aatttttaca    3180 ccttttttt cacattttac ataaataata atgctttgcc agcagtacgt ggtagccaca    3240
attgcacaat atatttcctt aaaaaatacc agcagttact catggaatat attctgcgtt    3300
tataaaacta gttttaaga agaaattttt tttggcctat gaaattgtta aacctggaac    3360 atgcacattgt taatcatata ataatgattc ttaaatgctg tatggtttat tatttaaatg    3420
ggtaaagcca tttacataat atagaaagat atgcatatat ctagaaggta tgtggcattt    3480
atttggataa aattctcaat tcagagaaat catctgatgt ttctatagtc actttgccag    3540
ctcaaaagaa aacaataccc tatgtagttg tggaagtta tgctaatatt gtgtaactga    3600
tattaaacct aaatgttctg cctacccctgt tggtataaag atatttgag cagactgtaa    3660 acaagaaaaa aaaaatcatg cattcttagc aaaattgcct agtatgttaa tttgctcaaa    3720
atacaatgtt tgattttatg cactttgtcg ctattaacat cctttttc atgtagattt    3780 caataattga gtaattttag aagcattatt ttaggaatat atagttgtca cagtaaatat    3840
cttgtttttt ctatgtacat tgtacaaatt tttcattcct tttgctcttt gtggttggat    3900
ctaacactaa ctgtattgtt ttgttacatc aaataaacat cttctgtgga ccaggcaaaa    3960
aaaaaaaaaa aaaaaaaa                                                   3979
```

<210> SEQ ID NO 8
<211> LENGTH: 826
<212> TYPE: PRT
<213> ORGANISM: Homo sapiens

<400> SEQUENCE: 8

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

```
Asn Val Ser Ser His Leu Asp Lys Ala Ser Val Met Arg Leu Thr Ile
 50                  55                  60

Ser Tyr Leu Arg Val Arg Lys Leu Leu Asp Ala Gly Asp Leu Asp Ile
 65                  70                  75                  80

Glu Asp Asp Met Lys Ala Gln Met Asn Cys Phe Tyr Leu Lys Ala Leu
                 85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
```

Asn Pro Glu Ser Leu Glu Leu Ser Phe Thr Met Pro Gln Ile Gln Asp
            465                 470                 475                 480

Gln Thr Pro Ser Pro Ser Asp Gly Ser Thr Arg Gln Ser Ser Pro Glu
            485                 490                 495

Pro Asn Ser Pro Ser Glu Tyr Cys Phe Tyr Val Asp Ser Asp Met Val
            500                 505                 510

Asn Glu Phe Lys Leu Glu Leu Val Glu Lys Leu Phe Ala Glu Asp Thr
            515                 520                 525

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                        565                 570                 575

Phe Asp Gln Leu Ser Pro Leu Glu Ser Ser Ser Ala Ser Pro Glu Ser
                    580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                        645                 650                 655

Ser Pro Tyr Arg Asp Thr Gln Ser Arg Thr Ala Ser Pro Asn Arg Ala
                    660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                        725                 730                 735

Leu Leu Gln Gln Pro Asp Asp His Ala Ala Thr Thr Ser Leu Ser Trp
                    740                 745                 750

Lys Arg Val Lys Gly Cys Lys Ser Ser Glu Gln Asn Gly Met Glu Gln
                755                 760                 765

Lys Thr Ile Ile Leu Ile Pro Ser Asp Leu Ala Cys Arg Leu Leu Gly
            770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                        805                 810                 815

Glu Leu Leu Arg Ala Leu Asp Gln Val Asn
                    820                 825

<210> SEQ ID NO 9
<211> LENGTH: 826
<212> TYPE: PRT
<213> ORGANISM: Homo sapiens

<400> SEQUENCE: 9

Met Glu Gly Ala Gly Gly Ala Asn Asp Lys Lys Lys Ile Ser Ser Glu
1               5                   10                  15

-continued

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu

```
            435                 440                 445
Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
                515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
                740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
            770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 10
<211> LENGTH: 826
<212> TYPE: PRT
<213> ORGANISM: Homo sapiens
```

<400> SEQUENCE: 10

Met Glu Gly Ala Gly Gly Ala Asn Asp Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65              70                  75                  80

Glu Asp Asp Met Lys Ala Gln Met Asn Cys Phe Tyr Leu Lys Ala Leu
            85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
        130                 135                 140

Arg Glu Met Leu Thr His Arg Asn Gly Leu Val Lys Gly Lys Glu
145             150                 155                 160

Gln Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225             230                 235                 240

Thr Phe Leu Ser Arg His Ser Leu Asp Met Lys Phe Ser Tyr Cys Asp
            245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser His Leu Thr
            275                 280                 285

Lys Thr His His Asp Met Phe Thr Lys Gly Gln Val Thr Thr Gly Gln
            290                 295                 300

Tyr Arg Met Leu Ala Lys Arg Gly Gly Tyr Val Trp Val Glu Thr Gln
305             310                 315                 320

Ala Thr Val Ile Tyr Asn Thr Lys Asn Ser Gln Pro Gln Cys Ile Val
            325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
            370                 375                 380

Ser Leu Phe Asp Lys Leu Lys Lys Glu Pro Asp Ala Leu Thr Leu Leu
385             390                 395                 400

Ala Pro Ala Ala Gly Asp Thr Ile Ile Ser Leu Asp Phe Gly Ser Asn

```
                405                 410                 415
Asp Thr Glu Thr Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
                435                 440                 445

Ala Met Ser Pro Leu Pro Thr Ala Glu Thr Pro Lys Pro Leu Arg Ser
            450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825
```

<210> SEQ ID NO 11
<211> LENGTH: 72
<212> TYPE: DNA
<213> ORGANISM: Homo sapiens

<400> SEQUENCE: 11

| | | |
|---|---|---|
| tgtcgggtag cttatcagac tgatgttgac tgttgaatct catggcaaca ccagtcgatg | 60 |
| ggctgtctga ca | 72 |

<210> SEQ ID NO 12
<211> LENGTH: 4148
<212> TYPE: DNA
<213> ORGANISM: Homo sapiens

<400> SEQUENCE: 12

| | |
|---|---|
| aggaaggaag gagcagttgg ttcaatctct ggtaatctat gccagcaatt atgacaatgt | 60 |
| tagcagacca tgcagctcgt cagctgcttg atttcagcca aaaactggat atcaacttat | 120 |
| tagataatgt ggtgaattgc ttataccatg agaaggagc ccagcaaaga atggctcaag | 180 |
| aagtactgac acatttaaag gagcatcctg atgcttggac aagagtcgac acaattttgg | 240 |
| aattttctca gaatatgaat acgaaatact atggactaca aattttggaa atgtgataa | 300 |
| aaacaaggtg gaagattctt ccaaggaacc agtgcgaagg aataaaaaaa tacgttgttg | 360 |
| gcctcattat caagacgtca tctgacccaa cttgtgtaga gaaagaaaag gtgtatatcg | 420 |
| gaaaattaaa tatgatcctt gttcagatac tgaaacaaga atggcccaaa cattggccaa | 480 |
| cttttatcag tgatattgtt ggagcaagta ggaccagcga agtctctgt caaaataata | 540 |
| tggtgattct taaactcttg agtgaagaag tatttgattt ctctagtgga cagataaccc | 600 |
| aagtcaaatc taagcattta aaagacagca tgtgcaatga attctcacag atatttcaac | 660 |
| tgtgtcagtt tgtaatggaa aattctcaaa atgctccact tgtacatgca accttggaaa | 720 |
| cattgctcag atttctgaac tggattcccc tgggatatat ttttgagacc aaattaatca | 780 |
| gcacattgat ttataagttc ctgaatgttc aatgtttcg aaatgtctct ctgaagtgcc | 840 |
| tcactgagat tgctggtgtg agtgtaagcc aatatgaaga acaatttgta acactattta | 900 |
| ctctgacaat gatgcaacta aagcagatgc ttccttaaa taccaatatt cgacttgcgt | 960 |
| actcaaatgg aaaagatgat gaacagaact tcattcaaaa tctcagtttg tttctctgca | 1020 |
| cctttcttaa ggaacatgat caacttatag aaaaaagatt aaatctcagg gaaactctta | 1080 |
| tggaggccct tcattatatg ttgttggtat ctgaagtaga agaaactgaa atctttaaaa | 1140 |
| tttgtcttga atactggaat catttggctg ctgaactcta tagagagagt ccattctcta | 1200 |
| catctgcctc tccgttgctt tctggaagtc aacattttga tgttcctccc aggagacagc | 1260 |
| tatatttgcc catgttattc aaggtccgtt tattaatggt tagtcgaatg gctaaaccag | 1320 |
| aggaagtatt ggttgtagag aatgatcaag gagaagttgt gagagaattc atgaaggata | 1380 |
| cagattccat aaatttgtat aagaatatga gggaaacatt ggtttatctt actcatctgg | 1440 |
| attatgtaga tacagaaaga ataatgacag agaagcttca caatcaagtg aatggtacag | 1500 |
| agtggtcatg gaaaaatttg aatacattgt gttgggcaat aggctccatt agtggagcaa | 1560 |
| tgcatgaaga ggacgaaaaa cgatttcttg ttactgttat aaaggatcta ttaggattat | 1620 |
| gtgaacagaa aagaggcaaa gataataaag ctattattgc atcaaatatc atgtacatag | 1680 |
| taggtcaata cccacgttt ttgagagctc actggaaatt tctgaagact gtagttaaca | 1740 |

```
agctgttcga attcatgcat gagacccatg atggagtcca ggatatggct tgtgatactt    1800
tcattaaaat agcccaaaaa tgccgcaggc atttcgttca ggttcaggtt ggagaagtga    1860
tgccatttat tgatgaaatt ttgaacaaca ttaacactat tatttgtgat cttcagcctc    1920
aacaggttca tacgttttat gaagctgtgg ggtacatgat tggtgcacaa acagatcaaa    1980
cagtacaaga gcacttgata gaaaagtaca tgttactccc taatcaagtg tgggatagta    2040
taatccagcg ggcaaccaaa aatgtggata tactgaaaga tcctgaaaca gtcaagcagc    2100
ttggtagcat tttgaaaaca aatgtgagag cctgcaaagc tgttggacac cccttttgtaa   2160 ttcagcttgg aagaatttat ttagatatgc ttaatgtata caagtgcctc agtgaaaata    2220
tttctgcagc tatccaagct aatggtgaaa tggttacaaa gcaaccattg attagaagta    2280
tgcgaactgt aaaaagggaa actttaaagt taatatctgg ttgggtgagc cgatccaatg    2340
atccacagat ggtcgctgaa aattttgttc cccctctgtt ggatgcagtt ctcattgatt    2400
atcagagaaa tgtcccagct gctagagaac cagaagtgct tagtactatg gccataattg    2460
tcaacaagtt agggggacat ataacagctg aaatacctca aatatttgat gctgtttttg    2520
aatgcacatt gaatatgata aataaggact tgaagaata tcctgaacat agaacgaact     2580
ttttcttact acttcaggct gtcaattctc attgttccc agcattcctt gctattccac      2640
ctacacagtt taaacttgtt ttggattcca tcatttgggc tttcaaacat actatgagga    2700
atgtcgcaga tacgggctta cagatacttt ttacactctt acaaaatgtt gcacaagaag    2760
aagctgcagc tcagagtttt tatcaaactt attttttgtga tattctccag catatctttt    2820
ctgttgtgac agacacttca catactgctg gtttaacaat gcatgcatca attcttgcat    2880
atatgtttaa tttggttgaa gaaggaaaaa taagtacatc attaaatcct ggaaatccag    2940
ttaacaacca aatctttctt caggaatatg tggctaatct ccttaagtcg gccttccctc    3000
acctacaaga tgctcaagta aagctctttg tgacagggct tttcagctta aatcaagata    3060
ttcctgcttt caaggaacat ttaagagatt tcctagttca aataaggaa tttgcaggtg     3120 aagacacttc tgatttgttt ttggaagaga gagaaatagc cctacggcag gctgatgaag    3180
agaaacataa acgtcaaatg tctgtccctg gcatctttaa tccacatgag attccagaag    3240
aaatgtgtga ttaaaatcca aattcatgct gtttttttc tctgcaactc cgttagcaga    3300
ggaaaacagc atgtgggtat ttgtcgacca aatgatgcc aatttgtaaa ttaaaatgtc     3360
acctagtggc ccttttctt atgtgttttt ttgtataaga aattttctgt gaaatatcct     3420
tccattgttt aagcttttgt tttggtcatc tttatttagt ttgcatgaag ttgaaaatta    3480 aggcatttt aaaaatttta cttcatgccc attttttgtgg ctgggctggg gggaggaggc    3540
aaattcaatt tgaacatata cttgtaattc taatgcaaaa ttatacaatt tttcctgtaa    3600
acaataccaa tttttaatta gggagcattt tccttctagt ctatttcagc ctagaagaaa    3660
agataatgag taaaacaaat tgcgttgttt aaaggattat agtgctgcat tgtctgaagt    3720
tagcacctct tggactgaat cgtttgtcta gactacatgt attacaaagt ctctttggca    3780
agattgcagc aagatcatgt gcatatcatc ccattgtaaa gcgacttcaa aaatatggga    3840
acacagttag ttattttac acagttcttt ttgtttttgt gtgtgtgtgc tgtcgcttgt     3900
cgacaacagc ttttttgtttt cctcaatgag gagtgttgct catttgtgag ccttcattaa    3960
ctcgaagtga aatggttaaa aatatttatc ctgttagaat aggctgcatc ttttttaacaa   4020 ctcattaaaa aacaaaacaa ctctggcttt tgagatgact tatactaatt tacattgttt    4080
accaagctgt agtgctttaa gaacactact taaaaagcaa aataaacttg gtttacattt    4140
``` aaaaaaaa                                                                4148

<210> SEQ ID NO 13
<211> LENGTH: 1071
<212> TYPE: PRT
<213> ORGANISM: Homo sapiens

<400> SEQUENCE: 13

Met Pro Ala Ile Met Thr Met Leu Ala Asp His Ala Ala Arg Gln Leu
1               5                   10                  15

Leu Asp Phe Ser Gln Lys Leu Asp Ile Asn Leu Leu Asp Asn Val Val
            20                  25                  30

Asn Cys Leu Tyr His Gly Glu Gly Ala Gln Gln Arg Met Ala Gln Glu
        35                  40                  45

Val Leu Thr His Leu Lys Glu His Pro Asp Ala Trp Thr Arg Val Asp
    50                  55                  60

Thr Ile Leu Glu Phe Ser Gln Asn Met Asn Thr Lys Tyr Tyr Gly Leu
65                  70                  75                  80

Gln Ile Leu Glu Asn Val Ile Lys Thr Arg Trp Lys Ile Leu Pro Arg
                85                  90                  95

Asn Gln Cys Glu Gly Ile Lys Lys Tyr Val Val Gly Leu Ile Ile Lys
            100                 105                 110

Thr Ser Ser Asp Pro Thr Cys Val Glu Lys Glu Lys Val Tyr Ile Gly
        115                 120                 125

Lys Leu Asn Met Ile Leu Val Gln Ile Leu Lys Gln Glu Trp Pro Lys
130                 135                 140

His Trp Pro Thr Phe Ile Ser Asp Ile Val Gly Ala Ser Arg Thr Ser
145                 150                 155                 160

Glu Ser Leu Cys Gln Asn Asn Met Val Ile Leu Lys Leu Leu Ser Glu
                165                 170                 175

Glu Val Phe Asp Phe Ser Ser Gly Gln Ile Thr Gln Val Lys Ser Lys
            180                 185                 190

His Leu Lys Asp Ser Met Cys Asn Glu Phe Ser Gln Ile Phe Gln Leu
        195                 200                 205

Cys Gln Phe Val Met Glu Asn Ser Gln Asn Ala Pro Leu Val His Ala
    210                 215                 220

Thr Leu Glu Thr Leu Leu Arg Phe Leu Asn Trp Ile Pro Leu Gly Tyr
225                 230                 235                 240

Ile Phe Glu Thr Lys Leu Ile Ser Thr Leu Ile Tyr Lys Phe Leu Asn
                245                 250                 255

Val Pro Met Phe Arg Asn Val Ser Leu Lys Cys Leu Thr Glu Ile Ala
            260                 265                 270

Gly Val Ser Val Ser Gln Tyr Glu Glu Gln Phe Val Thr Leu Phe Thr
        275                 280                 285

Leu Thr Met Met Gln Leu Lys Gln Met Leu Pro Leu Asn Thr Asn Ile
    290                 295                 300

Arg Leu Ala Tyr Ser Asn Gly Lys Asp Asp Glu Gln Asn Phe Ile Gln
305                 310                 315                 320

Asn Leu Ser Leu Phe Leu Cys Thr Phe Leu Lys Glu His Asp Gln Leu
                325                 330                 335

Ile Glu Lys Arg Leu Asn Leu Arg Glu Thr Leu Met Glu Ala Leu His
            340                 345                 350

Tyr Met Leu Leu Val Ser Glu Val Glu Glu Thr Glu Ile Phe Lys Ile
        355                 360                 365

```
Cys Leu Glu Tyr Trp Asn His Leu Ala Ala Glu Leu Tyr Arg Glu Ser
    370                 375                 380

Pro Phe Ser Thr Ser Ala Ser Pro Leu Leu Ser Gly Ser Gln His Phe
385                 390                 395                 400

Asp Val Pro Pro Arg Arg Gln Leu Tyr Leu Pro Met Leu Phe Lys Val
                405                 410                 415

Arg Leu Leu Met Val Ser Arg Met Ala Lys Pro Glu Glu Val Leu Val
            420                 425                 430

Val Glu Asn Asp Gln Gly Glu Val Val Arg Glu Phe Met Lys Asp Thr
        435                 440                 445

Asp Ser Ile Asn Leu Tyr Lys Asn Met Arg Glu Thr Leu Val Tyr Leu
450                 455                 460

Thr His Leu Asp Tyr Val Asp Thr Glu Arg Ile Met Thr Glu Lys Leu
465                 470                 475                 480

His Asn Gln Val Asn Gly Thr Glu Trp Ser Trp Lys Asn Leu Asn Thr
                485                 490                 495

Leu Cys Trp Ala Ile Gly Ser Ile Ser Gly Ala Met His Glu Glu Asp
                500                 505                 510

Glu Lys Arg Phe Leu Val Thr Val Ile Lys Asp Leu Leu Gly Leu Cys
            515                 520                 525

Glu Gln Lys Arg Gly Lys Asp Asn Lys Ala Ile Ile Ala Ser Asn Ile
        530                 535                 540

Met Tyr Ile Val Gly Gln Tyr Pro Arg Phe Leu Arg Ala His Trp Lys
545                 550                 555                 560

Phe Leu Lys Thr Val Val Asn Lys Leu Phe Glu Phe Met His Glu Thr
                565                 570                 575

His Asp Gly Val Gln Asp Met Ala Cys Asp Thr Phe Ile Lys Ile Ala
            580                 585                 590

Gln Lys Cys Arg Arg His Phe Val Gln Val Gln Val Gly Glu Val Met
        595                 600                 605

Pro Phe Ile Asp Glu Ile Leu Asn Asn Ile Asn Thr Ile Ile Cys Asp
610                 615                 620

Leu Gln Pro Gln Gln Val His Thr Phe Tyr Glu Ala Val Gly Tyr Met
625                 630                 635                 640

Ile Gly Ala Gln Thr Asp Gln Thr Val Gln Glu His Leu Ile Glu Lys
                645                 650                 655

Tyr Met Leu Leu Pro Asn Gln Val Trp Asp Ser Ile Ile Gln Gln Ala
            660                 665                 670

Thr Lys Asn Val Asp Ile Leu Lys Asp Pro Glu Thr Val Lys Gln Leu
        675                 680                 685

Gly Ser Ile Leu Lys Thr Asn Val Arg Ala Cys Lys Ala Val Gly His
690                 695                 700

Pro Phe Val Ile Gln Leu Gly Arg Ile Tyr Leu Asp Met Leu Asn Val
705                 710                 715                 720

Tyr Lys Cys Leu Ser Glu Asn Ile Ser Ala Ile Gln Ala Asn Gly
                725                 730                 735

Glu Met Val Thr Lys Gln Pro Leu Ile Arg Ser Met Arg Thr Val Lys
            740                 745                 750

Arg Glu Thr Leu Lys Leu Ile Ser Gly Trp Val Ser Arg Ser Asn Asp
        755                 760                 765

Pro Gln Met Val Ala Glu Asn Phe Val Pro Pro Leu Leu Asp Ala Val
770                 775                 780
```

-continued

```
Leu Ile Asp Tyr Gln Arg Asn Val Pro Ala Ala Arg Glu Pro Glu Val
785                 790                 795                 800

Leu Ser Thr Met Ala Ile Ile Val Asn Lys Leu Gly Gly His Ile Thr
                805                 810                 815

Ala Glu Ile Pro Gln Ile Phe Asp Ala Val Phe Glu Cys Thr Leu Asn
                820                 825                 830

Met Ile Asn Lys Asp Phe Glu Glu Tyr Pro Glu His Arg Thr Asn Phe
                835                 840                 845

Phe Leu Leu Leu Gln Ala Val Asn Ser His Cys Phe Pro Ala Phe Leu
                850                 855                 860

Ala Ile Pro Pro Thr Gln Phe Lys Leu Val Leu Asp Ser Ile Ile Trp
865                 870                 875                 880

Ala Phe Lys His Thr Met Arg Asn Val Ala Asp Thr Gly Leu Gln Ile
                885                 890                 895

Leu Phe Thr Leu Leu Gln Asn Val Ala Gln Glu Glu Ala Ala Ala Gln
                900                 905                 910

Ser Phe Tyr Gln Thr Tyr Phe Cys Asp Ile Leu Gln His Ile Phe Ser
                915                 920                 925

Val Val Thr Asp Thr Ser His Thr Ala Gly Leu Thr Met His Ala Ser
930                 935                 940

Ile Leu Ala Tyr Met Phe Asn Leu Val Glu Glu Gly Lys Ile Ser Thr
945                 950                 955                 960

Ser Leu Asn Pro Gly Asn Pro Val Asn Asn Gln Ile Phe Leu Gln Glu
                965                 970                 975

Tyr Val Ala Asn Leu Leu Lys Ser Ala Phe Pro His Leu Gln Asp Ala
                980                 985                 990

Gln Val Lys Leu Phe Val Thr Gly Leu Phe Ser Leu Asn Gln Asp Ile
                995                 1000                1005

Pro Ala Phe Lys Glu His Leu Arg Asp Phe Leu Val Gln Ile Lys
    1010                1015                1020

Glu Phe Ala Gly Glu Asp Thr Ser Asp Leu Phe Leu Glu Glu Arg
    1025                1030                1035

Glu Ile Ala Leu Arg Gln Ala Asp Glu Glu Lys His Lys Arg Gln
    1040                1045                1050

Met Ser Val Pro Gly Ile Phe Asn Pro His Glu Ile Pro Glu Glu
    1055                1060                1065

Met Cys Asp
    1070
```